(12) United States Patent
Schafer et al.

(10) Patent No.: US 11,795,315 B2
(45) Date of Patent: Oct. 24, 2023

(54) GROUP 5 METAL COMPLEXES FOR PRODUCING AMINE-FUNCTIONALIZED POLYOLEFINS

(71) Applicant: The University of British Columbia, Vancouver (CA)

(72) Inventors: Laurel L. Schafer, Vancouver (CA); Sorin-Claudiu Rosca, Vancouver (CA); Sabrina Scott, Vancouver (CA)

(*) Notice: Subject to any disclaimer, the term of this patent is extended or adjusted under 35 U.S.C. 154(b) by 279 days.

(21) Appl. No.: 17/056,903

(22) PCT Filed: Jan. 11, 2019

(86) PCT No.: PCT/CA2019/050046
§ 371 (c)(1),
(2) Date: Nov. 19, 2020

(87) PCT Pub. No.: WO2019/222834
PCT Pub. Date: Nov. 28, 2019

(65) Prior Publication Data
US 2022/0363786 A1  Nov. 17, 2022

Related U.S. Application Data

(60) Provisional application No. 62/675,465, filed on May 23, 2018.

(51) Int. Cl.
*C08L 23/36* (2006.01)
*C08F 8/32* (2006.01)
(Continued)

(52) U.S. Cl.
CPC ......... *C08L 23/36* (2013.01); *B01J 31/1616* (2013.01); *C08F 8/32* (2013.01); *C08F 210/16* (2013.01);
(Continued)

(58) Field of Classification Search
CPC . C07C 209/60; B01J 31/2243; B01J 2531/56; B01J 2531/57; B01J 2531/58
(Continued)

(56) References Cited

U.S. PATENT DOCUMENTS 5,444,125 A * 8/1995 Tomita .................. C08F 8/32
                                                     525/379
8,669,326 B2   3/2014 Hagadorn et al.
(Continued)

FOREIGN PATENT DOCUMENTS

WO    2012040853 A1   4/2012
WO    2018213938 A1   11/2018

OTHER PUBLICATIONS

International Search Report and Written Opinion of the International Searching Authority for International Patent Application No. PCT/CA2019/050046, dated Mar. 29, 2019, 11 pages.
(Continued)

*Primary Examiner* — Fred M Teskin
(74) *Attorney, Agent, or Firm* — Todd Lorenz; Todd A. Ostomel

(57) ABSTRACT

This application pertains to group 5 metal complexes having the structure of Formula I:

(Formula I)

(Continued)

and their potential utility in catalyzing amination of polyolefins having alkene groups.

20 Claims, 35 Drawing Sheets

(51) Int. Cl.
    B01J 31/16         (2006.01)
    B01J 31/18         (2006.01)
    C08F 210/16        (2006.01)
(52) U.S. Cl.
    CPC ....... *B01J 2531/58* (2013.01); *C08F 2810/40* (2013.01)
(58) Field of Classification Search
    USPC .............................................. 525/333.7, 379
    See application file for complete search history.

(56) References Cited

U.S. PATENT DOCUMENTS

| | | |
|---|---|---|
| 10,738,008 B2 | 8/2020 | Anthis et al. |
| 2006/0102895 A1 | 5/2006 | Hendrix et al. |
| 2020/0283459 A1 | 9/2020 | Schafer et al. |

OTHER PUBLICATIONS

Ackermann Lutz (Jun. 8, 2010) "Metal-Catalyzed Direct Alkylations of (Hetero)arenes Via C—H Bond Cleavages with Unactivated Alkyl Halides", Chemical Communications, 46:4866-4877.

Aresta et al. (Aug. 14, 2010) "The Solid State Structure and Reactivity of NbCl(5) X (N,N'-Dicyclohexylurea) In Solution: Evidence for Co-ordinated Urea Dehydration to the Relevant Carbodiimide", Dalton Transactions, 39(30):6985-6992.

Brandt et al. (Aug. 22, 2017) "Ligand Effects and Kinetic Investigations of Sterically Accessible 2-Pyridonate Tantalum Complexes for Hydroaminoalkylation", ACS Catalysis, 7(9):6323-6330.

Chen et al. (Jun. 29, 2009) "Palladium(II)-Catalyzed C—H Activation/C—C Cross-Coupling Reactions: Versatility and Practicality", Angewandte Chemie International Edition, 48(28):5094-5115.

Chisholm et al. (Jun. 1, 1981) "Chloro(dimethylamido) Compounds of Tantalum(V): Preparations, Properties, and Structures of [Ta(NMe2)3Cl2]2, TaCl3(NMe2)2(HNMe2), Ta(NMe2)3Cl2(HNMe2), and [TaCl2(NMe2)2(HNMe2)]2O", Inorganic Chemistry, 20(6):1859-1866.

Chong et al. (Jul. 20, 2014) "2-Pyridonate Tantalum Complexes for the Intermolecular Hydroaminoalkylation of Sterically Demanding Alkenes", Journal of the American Chemical Society, 136(31):10898-10901.

Chong et al. (2014) "Hydroaminoalkylation: Early-Transition-Metal-Catalyzed α-Alkylation of Amines", Synthesis, 46(21):2884-2896.

Clarkson et al. (Apr. 26, 2017) "Bis(tert-butylimido)bis(N,O-chelate)tungsten(VI) Complexes: Probing Amidate and Pyridonate Hemilability", Inorganic Chemistry, 56(10):5553-5566.

Clerici et al. (Apr. 1980) "Catalytic C-Alkylation of Secondary Amines with Alkenes", Synthesis, 305-306.

Colby et al. (2012) "Rhodium Catalyzed Chelation-Assisted C—H Bond Functionalization Reactions", Accounts of Chemical Research, 45(6):814-825.

Dipucchio et al. (Mar. 19, 2018) "Catalytic and Atom-Economic Csp3-Csp3 Bond Formation: Alkyl Tantalum Ureates for Hydroaminoalkylation", Angewandte Chemie International Edition England, 57(13):3469-3472.

Dorfler et al. (May 2014) "A Commercially Available Tantalum Catalyst for the Highly Regioselective Intermolecular Hydroaminoalkylation of Styrenes", European Journal of Organic Chemistry, 2014(13): 2790-2797.

Drew et al. (May 9, 1975) "Crystal and Molecular Structure of Two Seven-co-ordinate Distorted Pentagonal Bipyramidal Complexes of Tantalum(V)", Journal of the Chemical Society, Dalton Transactions, 2611-2617.

Edwards et al. (Oct. 18, 2017) "In Situ Generation of a Regio- and Diastereoselective Hydroaminoalkylation Catalyst Using Commercially Available Starting Materials", Organic Letters, 19(21):5720-5723.

Eisenberger et al. (May 30, 2010) "Catalytic Synthesis of Amines and N-containing Heterocycles: Amidate Complexes for Selective C—N and C—C Bond-Forming Reactions", Pure and Applied Chemistry, 82(7):1503-1515.

Eisenberger et al. (2009) "Tantalum-Amidate Complexes for the Hydroaminoalkylation of Secondary Amines Enhanced Substrate Scope and Enantioselective Chiral Amine Synthesis", Angewandte Chemie International Edition, 48:8361-8365.

Franssen et al. (2013) "Synthesis of Functional 'Polyolefins': State of the Art and Remaining Challenges", Chemical Society Reviews, 42:5809-5832.

Garcia et al. (Apr. 18, 2013) "Easily Assembled, Modular N,O-chelating Ligands For TA(V) Complexation: A Comparative Study of Ligand Effects in Hydroaminoalkylation with N-methylaniline and 4-Methoxy-N-Methylaniline", Tetrahedron, 69(27-28):5737-5743.

Garcia et al. (Aug. 26, 2013) "Phosphoramidate Tantalum Complexes for Room-Temperature C—H Functionalization: Hydroaminoalkylation Catalysis", Angewandte Chemie International Edition, 52(35):9144-9148.

Goldmann et al. (May 27, 2013) "Post-Functionalization of Polymers via Orthogonal Ligation Chemistry", Macromolecular Rapid Communications, 34(10):810-849.

Hamzaoui et al. (Feb. 24, 2016) "Solid-State NMR and DFT Studies on the Formation of Well-Defined Silica-Supported Tantallaaziridines: From Synthesis to Catalytic Application", Chemistry European Journal, 22(9):3000-3008.

Herzon et al. (May 3, 2007) "Direct, Catalytic Hydroaminoalkylation of Unactivated Olefins with N-Alkyl Arylamines", Journal of the American Chemical Society, 129(21):6690-6691.

Herzon et al. (Nov. 12, 2008) "Hydroaminoalkylation of Unactivated Olefins with Dialkylamines", Journal of the American Chemical Society, 130(45):14940-14941.

Lau Yingy. (Dec. 2016) "Catalytic Synthesis of N-heterocycles and Alpha-Alkylated Amines by Hydroamination and Hydroaminoalkylation", The University of British Columbia, 319 pages.

Lauzon et al. (Aug. 9, 2017) "Amidate Complexes of Tantalum and Niobium for the Hydroaminoalkylation of Unactivated Alkenes", ACS Catalysis, 7(9):5921-5931.

Lauzon Jeanm. (May 2013) "Development of Group 4 and 5 Complexes with N,O Chelating Supporting Ligands as Catalysts for the A-alkylation of Amines", The University of British Columbia, 316 pages.

Le et al. (Jul. 6, 2017) "Selective sp3 C—H Alkylation via Polarity-Match-Based Cross-Coupling", Nature, , 547:79-83.

Lyons et al. (2010) "Palladium-Catalyzed Ligand-Directed C—H Functionalization Reactions", Chemical Reviews, 110(2):1147-1169.

Moorhouse et al. (Apr. 8, 1974) "Bis[(trimethylsilyl)methyl]- and bis(neopentyl)-zinc, and tris[(trimethylsilyl)methyl] aluminiumdiethyl ether (1/1); their use as alkylating agents in forming niobium and tantalum alkyls", Journal of the Chemical Society, Dalton Transactions, 2187-2190.

Nugent et al. (Jan. 1, 1983) "Catalytic C—H Activation in Early Transition-Metal Dialkylamides and Alkoxides", Organometallics, 2(1):161-162.

Oda et al. (2016) "Diene Hydroaminomethylation via Ruthenium-Catalyzed C—C Bond Forming Transfer Hydrogenation: Beyond Carbonylation", Chemical Science, 7:136-141.

Payne et al. (Apr. 19, 2013) "Tantalum Catalyzed Hydroaminoalkylation for the Synthesis of α- and β-Substituted N-Heterocycles", Organic Letters, 15(9):2182-2185.

(56) References Cited

OTHER PUBLICATIONS

Pelletier et al. (Mar. 9, 2016) "Catalysis by Design: Well-Defined Single-Site Heterogeneous Catalysts", Accounts of Chemical Research, 49(4):664-677.
Perez et al. (Jun. 2016) "Ruthenium-Catalyzed Transfer Hydrogenation for C—C Bond Formation Hydrohydroxyalkylation and Hydroaminoalkylation via Reactant Redox Pairs", Topics in Current Chemistry, 374(3): 34 pages.
Perry Mitchellr. (Sep. 2017) "Catalytic Synthesis of Amines : From Small Molecules to Nitrogen-Containing Polymers", The University of British Columbia, 373 pages.
Perry et al. (Jun. 13, 2016) "Catalytic Synthesis of Secondary Amine-Containing Polymers: Variable Hydrogen Bonding for Tunable Rheological Properties", Macromolecules, 49(12):4423-4430.
Reznichenko et al. (Jan. 12, 2011) "Group 5 Metal Binaphtholate Complexes for Catalytic Asymmetric Hydroaminoalkylation and Hydroamination/Cyclization", Organometallics, 30(5):921-924.
Reznichenko et al. (Jan. 19, 2012) "The Mechanism of Hydroaminoalkylation Catalyzed by Group 5 Metal Binaphtholate Complexes", Journal of the American Chemical Society, 134(6):3300-3311.
Roesky W.P. (2009) "Catalytic Hydroaminoalkylation", Angewandte Chemie International Edition, 48:4892-4894.
RYKEN et al. (Auguste, 2015) "N,O -Chelating Four-Membered Metallacyclic Titanium(IV) Complexes for Atom-Economic Catalytic Reactions", Accounts of Chemical Research, 48(9):2576-2586.
Ryken et al. (2016) "Tight Bite Angle N,0-Chelates. Amidates, Ureates and BeyondLigand Design in Metal Chemistry: Reactivity and Catalysis", Chapter 13, Ligand Design in Metal Chemistry: Reactivity and Catalysis, 364-405.
Sarkar et al. (2000) "Insulin Mimetic Peroxo Complexes of Vanadium Containing Uracil or Cytosine as Ligand", Metal-Based Drugs, 7(3):157-164.
Sattler et al. (Aug. 14, 2011) "Structural Characterization of TaMe3Cl2 and Ta(PMe3)2Me3Cl2, a Pair of five and Seven-Coordinate d0 Tantalum Methyl Compounds", Dalton Transactions, 40(30):7777-7782.
Schrock et al. (1978) "Multiple Metal-Carbon Bonds. 7. Preparation and characterization of Ta(.eta.5-C5H5)2(CH2)(CH3), a study of its decomposition, and some simple reactions", Journal of the American Chemical Society, 100(8):2389-2399.
Schrock et al. (May 24, 1978) "Multiple Metal-Carbon Bonds. 8. Preparation, Characterization, and Mechanism of Formation of the Tantalum and Niobium Neopentylidene Complexes, M(CH2CMe3)3(CHCMe3)", Journal of the American Chemical Society, 100(11):3359-3370.
Thullen et al. (2017) "A Mild Hydroaminoalkylation of Conjugated Dienes Using a Unified Cobalt and Photoredox Catalytic System", Journal of the American Chemical Society, 139(43):15504-15508.
Tran et al. (Aug. 21, 2017) "Practical Alkoxythiocarbonyl Auxiliaries for Iridium(I)-Catalyzed C—H Alkylation of Azacycles", Angewandte Chemie International Edition, 56(35):10530-10534.
Yamauchi et al. (May 11, 2017) "Hydroxoiridium-Catalyzed Hydroalkylation of Terminal Alkenes with Ureas by C (sp3)-H Bond Activation", Angewandte Chemie International Edition, 56(25):7200-7204.
Zhang et al. (Jan. 10, 2011) "Synthesis and Catalytic Activity of Group 5 Metal Amides with Chiral Biaryldiamine-Based Ligands", Dalton Transactions, 40:1547-1566.
Zhang et al. (Jul. 1, 2013) "TaMe3Cl2-Catalyzed Intermolecular Hydroaminoalkylation: A Simple Complex for Enhanced Reactivity and Expanded Substrate Scope", Chemistry—A European Journal, 19(27):8751-8754.
Zi et al. (2010) "Highly Enantioselective Hydroaminoalkylation of Secondary Amines Catalyzed by Group 5 Metal Amides with Chiral Biarylamidate Ligands", Chemical Communications, 46:6296-6298.

\* cited by examiner

*Acyclic Achiral Ureates (AAUs)*

*Achiral Ureates (AUs)*

GROUP 5 METAL COMPLEXES FOR PRODUCING AMINE-FUNCTIONALIZED POLYOLEFINS

RELATED APPLICATIONS

This application is a national phase application entry of PCT/CA2019/050046 filed on Jan. 11, 2019 which claims priority to U.S. patent application no. 62/675,465 filed on May 23, 2018, the contents of each of which are incorporated herein by reference in their entirety.

FIELD OF THE INVENTION

This disclosure relates to the use of group 5 metal complexes for amine functionalization and synthetic process for manufacture thereof. In particular, this disclosure relates to the use of such complexes for the amine functionalization of polyolefins comprising alkene groups.

BACKGROUND

The catalytic functionalization of alkenes represents a sustainable and efficient method for the synthesis of molecules that are relevant for the chemical, pharmaceutical, and agrochemical industry. Such organic transformations are attractive as valuable building blocks, which are obtained economically from relatively inexpensive starting materials. Notably, the direct C—H functionalization of amines with alkenes, or hydroaminoalkylation, has gained notoriety due to the fact that polysubstituted amines can now be easily obtained in the absence of any protecting/directing groups or photoinitiators. Post polymerization modification of polyethylenes with amines represents an attractive route towards the formation of valuable materials with a variety of potential applications.

It is known in the art that group 3 (Sc), 4 (Ti, Zr), and 5 (Nb, Ta) metal complexes may serve as powerful precatalysts in hydroaminoalkylation reactions. For example, N, O-chelated pyridonate tantalum based complexes were shown capable of reacting with sterically demanding internal alkenes and facilitate their reaction with secondary anilines. These reactions occurred in a 100% regioselective manner to give the branched products.

Despite the high demand of simple and economical methods for synthesis of amine building blocks in the chemical, pharmaceutical, and agrochemical industry, there are known issues with the catalytic systems presently in use. For instance, hydroaminoalkylation often requires high reaction temperatures (>110° C.) and quite long reaction times (>20 h), which many catalysts are not robust enough to tolerate. Moreover, substrate compatibility of these catalysts is known to be problematic, especially for internal alkenes such as cyclohexene and cyclooctene. The fact that excess alkene (at least 1.5 equivalents excess) is needed to achieve full substrate conversion remains a challenge as well. With respect to polyolefins, even though polyolefins can be aminated with secondary amines, the described processes in the literature suffer from long reaction times (>10 h), very high temperatures (180° C.) and narrow substrate scope (e.g. only N-methylaniline could be employed as an amine substrate).

In the case of the catalytic systems, where the active species have a Ta—NMe$_2$ moiety, the excess alkene is often justified by the deleterious side reactions between the released HNMe$_2$ and the alkene reagents, thereby affecting the stoichiometry of the reaction. The use of TaMe$_3$Cl$_2$ proved to be successful, as hydroaminoalkylations of amine and alkene substrates was achieved using this catalyst in stoichiometric amounts, but with the caveat that TaMe$_3$Cl$_2$ is light and temperature sensitive and therewith not suitable for large scale industrial processes. Using a similar approach, the addition of 1-octene to 4-methoxy-N-methyl-aniline at room temperature was achieved with a phosphoramidate supported Ta-Me complex as the catalyst. Although this catalyst demonstrated high reactivity, the phosphoramidate Ta-Me complex actually required excess alkene in order to fully convert the substrates. To improve the stability of early transition metal complexes, steric bulk in the form of e.g. bulky alkyl groups, such as for example CH$_2$SiMe$_3$ and CH$_2$CMe$_3$, may be complexed to the metal centre. Earlier, Wilkinson and Schrock have described the alkyl tantalum complexes Ta(CH$_2$SiMe$_3$)$_3$Cl$_2$ and Ta(CH$_2$CMe$_3$)$_3$Cl$_2$. However, their activity in hydroaminoalkylation reactions has not been reported in the art.

SUMMARY OF THE INVENTION

This disclosure is based in part on the discovery of group 5 metal complexes that are advantageous for catalyzing hydroaminoalkylation reactions. In particular, the present disclosure relates to group 5 metal complexes and their use for amine functionalization, as well as synthetic processes for manufacturing such complexes. The group 5 metal complexes described herein may catalyze hydroaminoalkylation reactions at stoichiometric ratios of N-containing heterocycle to alkene and at lower reaction temperatures than those reported in the art.

Aspects of this disclosure relate to a metal complex having the structure of Formula I:

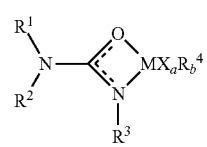

(Formula I)

wherein:

$R^1$ and $R^2$ are:
  each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
  bonded together thereby forming, together with the nitrogen atom they are both bound to, a heterocycle;

$R^3$:
  is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
  bonded together with $R^1$ and/or $R^2$ to form a heterocycle.

M is a group 5 metal;
a=0 to 4 and b=0 to 4, wherein the sum of a and b is 4;
each X is a halogen substituent;
each $R^4$ is independently: H; or a $C_1$-$C_{20}$ substituted or unsubstituted, linear, branched or cyclic alkyl, optionally comprising heteroatoms.

In various embodiments, each X is independently Cl or Br. In various embodiments, a may be 1 or 2.

$R^1$ and $R^2$ may each independently be: methyl; ethyl; isopropyl; cyclohexyl; phenyl; 2,6-dimethyl phenyl; 2,4,6- trimethyl phenyl; 4-methyl phenyl; optionally substituted piperidine; optionally substituted pyrrolidine; or substituted morpholine.

Alternatively, $R^1$ and $R^2$ may be bonded together to form, together with the nitrogen atom they are both bound to, a 6-membered ring, which optionally may be substituted.

In various embodiments, $R^1$ and $R^2$ are each phenyl. In various embodiments, $R^1$ is phenyl and $R^2$ is isopropyl. In various embodiments, $R^1$ and $R^2$ are bonded together to form, together with the nitrogen atom they are both bound to, piperidinyl. In various embodiments, $R^1$ is phenyl and $R^2$ is methyl; $R^1$ is phenyl and $R^2$ is methyl; $R^1$ is methyl and $R^2$ is 1-phenylethyl; In various embodiments, $R^1$ is methyl and $R^2$ is isopropyl; In various embodiments, $R^1$ is phenyl and $R^2$ is diphenylmethyl.

$R^3$ may be: phenyl; 2,6-dimethyl phenyl; 2,6-di(isopropyl)phenyl; or

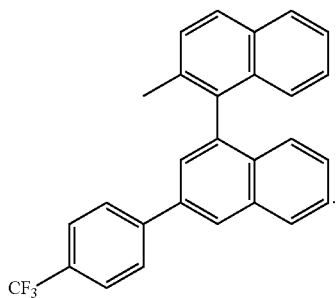 [SMILES: Cc1ccc2ccccc2c1-c1cc(-c2ccc(C(F)(F)F)cc2)cc2ccccc12]

$R^3$ may be bonded together with $R^1$ and/or $R^2$ to form, together with each of the nitrogen atoms they are bound to, a 5-membered ring, which optionally may be substituted. $R^3$ may be bonded together with $R^1$ and/or $R^2$, and each of the nitrogen atoms they are bound to, to form:

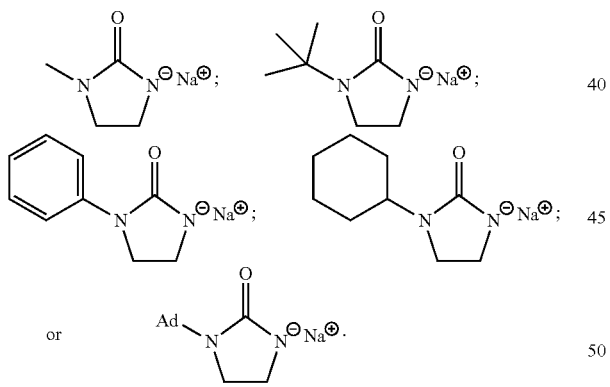

or

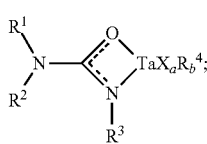

$R^4$ may be —$CH_3$, —$NMe_2$, —$CH_2C(CH_3)_3$, or —$CH_2Si(CH_3)_3$.

M may be tantalum (Ta), niobium (Nb), or vanadium (V).

Aspects of this disclosure further related to a metal complex having the structure of Formula II $$\text{(Formula II)}$$

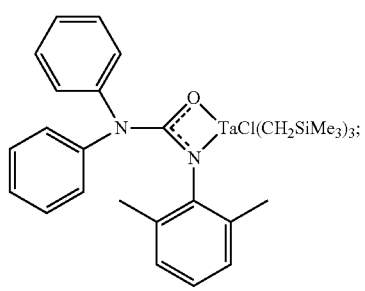

wherein:
  $R^1$ and $R^2$ are:
    each independently: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine; or
    bonded together to form, together with the nitrogen atom they are both bound to, a 6-membered ring, which optionally may be substituted;
  $R^3$ is:
    phenyl; 2,6-dimethyl phenyl; or 2,6-di(isopropyl) phenyl; or bonded together with $R^1$ and/or $R^2$ to form, together with each of the nitrogen atoms they are bound to, a 5-membered ring, which optionally may be substituted;
  each X is independently Cl or Br;
  a=1 or 2 and b=(4−a); and
  $R^4$ is —$CH_3$, —$NMe_2$, —$CH_2C(CH_3)_3$, or —$CH_2Si(CH_3)_3$.

Aspects of the disclosure related to a metal complex, which metal complex is:

(Formula III)

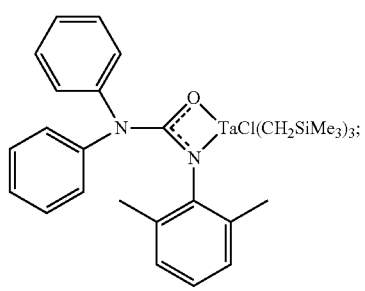

(Formula IV)

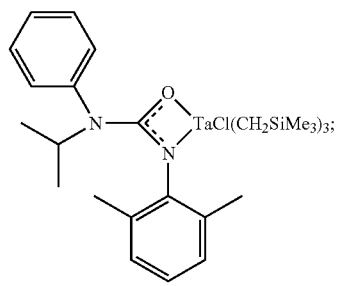

(Formula V)

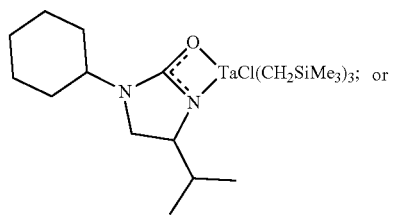

(Formula VI)

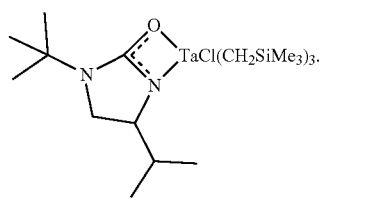

Aspects of this disclosure relate to a catalyst comprising a metal complex as defined above and elsewhere herein.

Aspects of this disclosure relate to a catalyst kit comprising at least one metal complex as defined above and elsewhere herein and a quenching agent. The quenching agent may include an alcohol, water, or a combination thereof.

Aspects of this disclosure relate to a method of synthesizing a metal complex of Formula I, the method comprising reacting a group 5 metal salt of Formula VII with one equivalent of an amide of Formula VIII according to the following reaction:

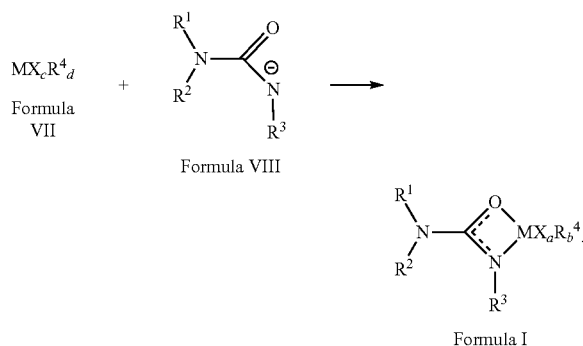

wherein:
R$^1$ and R$^2$ are:
  each independently: H; a C$_1$-C$_{40}$ substituted or unsubstituted linear, branched or cyclic alkyl or alkenyl or alkynyl; a substituted or unsubstituted aryl; or a substituted or unsubstituted heterocyclic group; or
  bonded together thereby forming, together with the nitrogen atom they are both bound to, a heterocycle;
R$^3$:
  is H; a C$_1$-C$_{40}$ substituted or unsubstituted linear, branched or cyclic alkyl or alkenyl or alkynyl; or a substituted or unsubstituted aryl; or a substituted or unsubstituted heterocyclic group; or
  bonded together with R$^1$ and/or R$^2$ to form a heterocycle.
M is a group 5 metal;
a=0 to 4 and b=0 to 4, wherein the sum of a and b is 4;
c=1 to 5 and d=0 to 4, wherein the sum of c and d is 5;
each X is a halogen substituent;
each R$^4$ is independently: H; or a C$_1$-C$_{20}$ substituted or unsubstituted, linear, branched or cyclic alkyl, optionally comprising heteroatoms.

X may be, independently, Cl or Br. In various embodiments, a may be 1 or 2.

R$^1$ and R$^2$ may each independently be: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine.

Alternatively, R$^1$ and R$^2$ may be bonded together to form, together with the nitrogen atom they are both bound to, a 6-membered ring, which optionally may be substituted.

In various embodiments, R$^1$ and R$^2$ are each phenyl. In various embodiments, R$^1$ is phenyl and R$^2$ is isopropyl. In various embodiments, R$^1$ and R$^2$ are bonded together to form, together with the nitrogen atom they are both bound to, piperidinyl. In various embodiments, R$^1$ is phenyl and R$^2$ is methyl; R$^1$ is methyl and R$^2$ is 1-phenylethyl; In various embodiments, R$^1$ is methyl and R$^2$ is isopropyl; In various embodiments, R$^1$ is phenyl and R$^2$ is diphenylmethyl.

R$^3$ may be: phenyl; 2,6-dimethyl phenyl; 2,6-di(isopropyl)phenyl; or

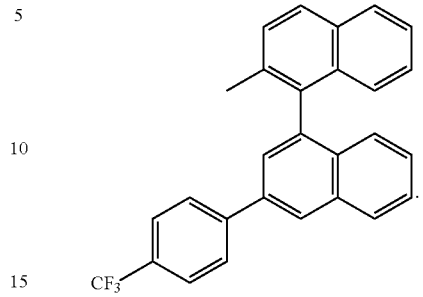

R$^3$ may be bonded together with R$^1$ and/or R$^2$ to form, together with each of the nitrogen atoms they are bound to, a 5-membered ring, which optionally may be substituted. R$^3$ may be bonded together with R$^1$ and/or R$^2$, and each of the nitrogen atoms they are bound to, to form:

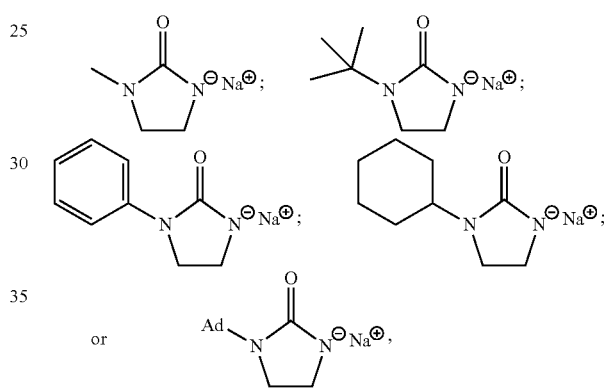

R$^4$ may be —CH$_3$, —NMe$_2$, —CH$_2$C(CH$_3$)$_3$, or —CH$_2$Si(CH$_3$)$_3$.

M may be tantalum (Ta), niobium (Nb), or vanadium (V).

In various embodiments, the reaction may be performed in a temperature range from −30° C. to ambient temperature.

In various embodiments, the reaction is performed at ambient temperature. Ambient temperature may be room temperature.

The reaction may be performed in an organic solvent. The organic solvent may be toluene or hexane.

In various embodiments, the method may include a further reaction step that is performed in situ.

Aspects of the disclosure relate to a method for α-alkylation of a secondary amine-containing moiety, the method comprising: (i) reacting said secondary amine-containing moiety with an olefin in the presence of a metal complex as defined above and elsewhere herein. The method may further include isolating a product formed in step (i).

The secondary amine-containing moiety may include at least two α-sp$^3$ hybridized C—H bonds.

The secondary amine-containing moiety may be a C$_4$-C$_{100}$ linear, branched, or cyclic alkyl, optionally substituted and/or comprising heteroatoms. The secondary amine-containing moiety may be substituted with a halogen, an ether, another amine, an alkyl, an alkene, an acetal, a phosphine, an amide, an alkyne, an imine, a nitrile, an isocyanide, an epoxide, a boronic acid ester; a phenyl that optionally may be substituted and/or part of a condensed ring system, or any combination thereof.

The olefin may include from 2 to 100 carbon atoms. In various embodiments, the olefin comprises an internal alkene. In various embodiments, the olefin is a linear or a cyclic olefin. In various embodiments, the olefin comprises a terminal alkene. In various embodiments, the olefin is an optionally substituted 1-alkene or an optionally substituted cycloalk-1-ene. In various embodiments, the olefin comprises one or more protected functional group(s). In various embodiments, the olefin is:

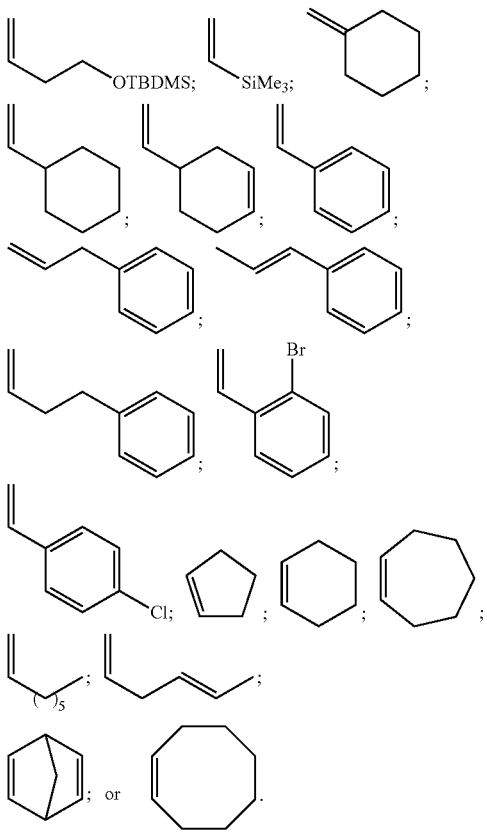

In various embodiments, the olefin is a polyolefin comprising at least one alkene group. In various embodiments, the at least one alkene group comprises an internal alkene group. In various embodiments, the at least one alkene group comprises at least one vinyl group. In various embodiments, the at least one alkene group comprises at least one pendant alkene group. In various embodiments, the at least one pendant alkene group comprises a pendant vinyl group. In various embodiments, at least one pendant alkene group comprises —CH=CHCH$_3$, —CH=CHCH$_2$CH$_3$, or both. In various embodiments, the polyolefin is a vinyl-terminated polyolefin. In various embodiments, the polyolefin comprises a polypropylene. In various embodiments, the polyolefin comprises an atactic polypropylene. In various embodiments, the polyolefin comprises a copolymer poly(ethylene-co-propylene). In various embodiments, the polyolefin comprises polyethylene.

In various embodiments, the molecular weight of the polyolefin is in the range of about 100 g/mol to about 10,000 g/mol. In various embodiments, the molecular weight of the polyolefin is in the range of about 350 g/mol to about 3,500 g/mol. In various embodiments, the molecular weight of the polyolefin is in the range of about 1,500 g/mol to about 2,000 g/mol. In various embodiments, the molecular weight of the polyolefin is about 350 g/mol, about 400 g/mol, about 450 g/mol, about 500 g/mol, about 550 g/mol, about 600 g/mol, about 650 g/mol, about 700 g/mol, about 750 g/mol, about 800 g/mol, about 850 g/mol, about 900 g/mol, about 950 g/mol, about 1000 g/mol, about 1050 g/mol, about 1,100 g/mol, about 1150 g/mol, about 1200 g/mol, about 1250 g/mol, about 1300 g/mol, about 1350 g/mol, about 1400 g/mol, about 1450 g/mol, about 1500 g/mol, about 1550 g/mol, about 1600 g/mol, about 1650 g/mol, about 1700 g/mol, about 1750 g/mol, about 1800 g/mol, about 1850 g/mol, about 1900 g/mol, about 1950 g/mol, about 2000 g/mol, about 2050 g/mol, about 2100 g/mol, about 2150 g/mol, about 2200 g/mol, about 2250 g/mol, about 2300 g/mol, about 2350 g/mol, about 2400 g/mol, about 2450 g/mol, about 2500 g/mol, about 2550 g/mol, about 2600 g/mol, about 2650 g/mol, about 2700 g/mol, about 2750 g/mol, about 2800 g/mol, about 2850 g/mol, about 2900 g/mol, about 2950 g/mol, about 3000 g/mol, about 3050 g/mol, about 3100 g/mol, about 3150 g/mol, about 3200 g/mol, about 3250 g/mol, about 3300 g/mol, about 3350 g/mol, about 3400 g/mol, about 3450 g/mol, or about 3500 g/mol.

The secondary amine-containing moiety may be: pyrrolidine; piperidine;

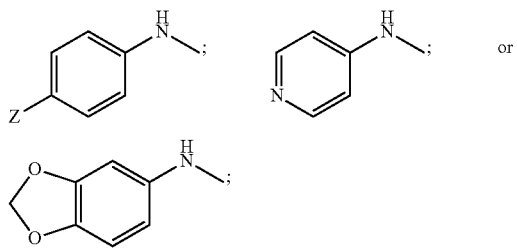

wherein Z is H, OCF$_3$, F, Cl, Br, I, or OCH$_3$.

The secondary amine-containing moiety may be:

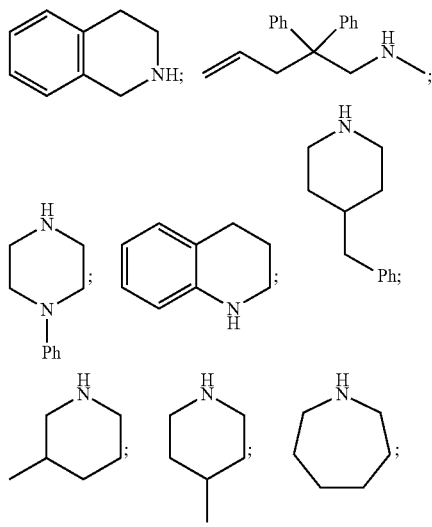

-continued

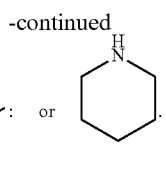

The reaction conditions may include a reaction temperature in the range from 50° C. to 200° C., a reaction temperature in the range from 75° C. to 165° C., a reaction temperature in the range from 90° C. to 150° C., a reaction temperature in the range from range from 110° C. to 130° C., a reaction temperature of about 110° C., or a reaction temperature of about 130° C.

The reaction conditions may include a solvent. The solvent may be non-protic. The solvent may be toluene, benzene, or a mixture thereof.

The secondary amine-containing moiety and said olefin may be provided in a stoichiometric ratio from 0.1 to 1.5. The secondary amine-containing moiety and said olefin may be provided in a stoichiometric ratio of about 1:1.

Aspects of the disclosure relate to a method of synthesizing a pharmaceutical compound or an agrochemical compound, the method comprising α-alkylation of a secondary amine-containing moiety according to a method as defined above and elsewhere herein.

Aspects of the disclosure relate to use of a group 5 metal salt of Formula VII $$MX_cR^4_d \qquad \text{(Formula VII)}$$

wherein:
  M is a group 5 metal;
  c=1 to 5 and d=0 to 4, wherein the sum of c and d is 5; and
  each $R^4$ is independently: H; or a $C_1$-$C_{20}$ substituted or unsubstituted, linear, branched or cyclic alkyl, optionally comprising heteroatoms,
in combination with an amide of Formula VIII

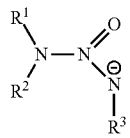
(Formula VIII)

wherein:
  $R^1$ and $R^2$ are:
    each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
    bonded together thereby forming, together with the nitrogen atom they are both bound to, a heterocycle; and
  $R^3$:
    is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
    bonded together with $R^1$ and/or $R^2$ to form a heterocycle.

for generating a catalyst for α-alkylation of a secondary amine-containing moiety.

The catalyst may be a metal complex of Formula I,

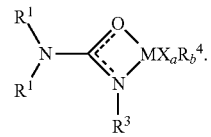
Formula I wherein a=0 to 4 and b=0 to 4, wherein the sum of a and b is 4.

In various embodiments, α-alkylation of a secondary amine-containing moiety comprises reacting said secondary amine-containing moiety with an olefin in the presence of the catalyst. The secondary-amine containing moiety and/or olefin may be as defined above and elsewhere herein.

Aspects of this disclosure relate to a method for α-alkylation of a secondary amine-containing moiety with a polyolefin comprising at least one alkene group or, in other words, a method for amination of a polyolefin comprising at least one alkene group. The method comprises: (i) reacting the secondary amine-containing moiety with the polyolefin in the presence of a metal complex, the metal complex having the structure of Formula I:

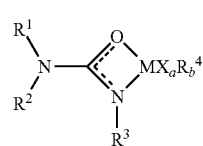
(Formula I)

wherein:
  $R^1$ and $R^2$ are:
    each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
    bonded together thereby forming, together with the nitrogen atom they are both bound to, a heterocycle;
  $R^3$:
    is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
    bonded together with $R^1$ and/or $R^2$ to form a heterocycle.
  M is a group 5 metal;
  a=0 to 4 and b=0 to 4, wherein the sum of a and b is 4;
  each X is a halogen substituent;
  each $R^4$ is independently: H; or a $C_1$-$C_{20}$ substituted or unsubstituted, linear, branched or cyclic alkyl, optionally comprising heteroatoms.

In various embodiments, each X is independently Cl or Br. In various embodiments, a is 1 or 2.

$R^1$ and $R^2$ may each independently be: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine.

Alternatively, $R^1$ and $R^2$ may be bonded together to form, together with the nitrogen atom they are both bound to, a 6-membered ring, which optionally may be substituted.

In various embodiments, $R^1$ and $R^2$ are each phenyl. In various embodiments, $R^1$ is phenyl and $R^2$ is isopropyl. In various embodiments, $R^1$ and $R^2$ are bonded together to form, together with the nitrogen atom they are both bound to, piperidinyl. In various embodiments, $R^1$ is phenyl and $R^2$ is methyl; $R^1$ is methyl and $R^2$ is 1-phenylethyl; In various embodiments, $R^1$ is methyl and $R^2$ is isopropyl; In various embodiments, $R^1$ is phenyl and $R^2$ is diphenylmethyl.

$R^3$ may be: phenyl; 2,6-dimethyl phenyl; 2,6-di(isopropyl)phenyl; or

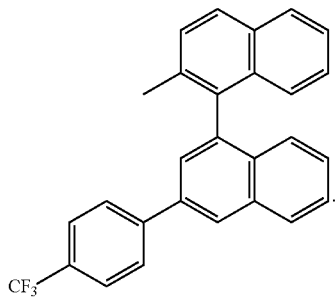 [SMILES: Cc1ccc2ccccc2c1-c1cc(-c2ccc(C(F)(F)F)cc2)cc2ccccc12]

$R^3$ may be bonded together with $R^1$ and/or $R^2$ to form, together with each of the nitrogen atoms they are bound to, a 5-membered ring, which optionally may be substituted. $R^3$ may be bonded together with $R^1$ and/or $R^2$, and each of the nitrogen atoms they are bound to, to form:

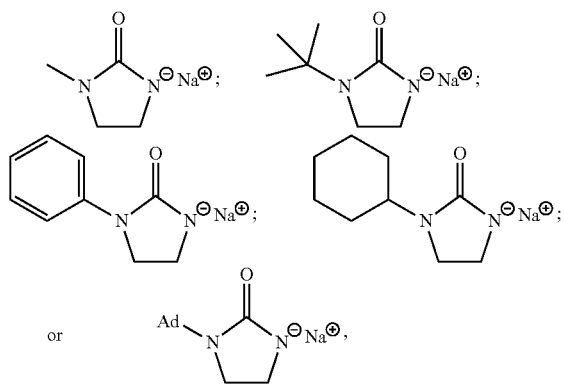

$R^4$ may be $-CH_3$, $-NMe_2$, $-CH_2C(CH_3)_3$, or $-CH_2Si(CH_3)_3$.

M may be tantalum (Ta), niobium (Nb), or vanadium (V).

Aspects of this disclosure relate to a method for α-alkylation of a secondary amine-containing moiety with a polyolefin comprising at least one alkene group or, in other words, a method for amination of a polyolefin comprising at least one alkene group. The method comprises: (i) reacting the secondary amine-containing moiety with the polyolefin in the presence of a metal complex, the metal complex having the structure of Formula II (Formula II)

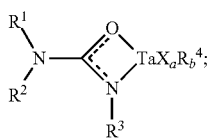

wherein:

$R^1$ and $R^2$ are:

each independently: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine; or bonded together to form, together with the nitrogen atom they are both bound to, a 6-membered ring, which optionally may be substituted;

$R^3$ is:

phenyl; 2,6-dimethyl phenyl; or 2,6-di(isopropyl) phenyl; or bonded together with $R^1$ and/or $R^2$ to form, together with each of the nitrogen atoms they are bound to, a 5-membered ring, which optionally may be substituted;

each X is independently Cl or Br;

a=1 or 2 and b=(4−a); and $R^4$ is $-CH_3$, $-NMe_2$, $-CH_2C(CH_3)_3$, or $-CH_2Si(CH_3)_3$.

Aspects of this disclosure relate to a method for α-alkylation of a secondary amine-containing moiety with a polyolefin comprising at least one alkene group or, in other words, a method for amination of a polyolefin comprising at least one alkene group. The method comprises: (i) reacting the secondary amine-containing moiety with the polyolefin in the presence of a metal complex, which metal complex is:

(Formula III)

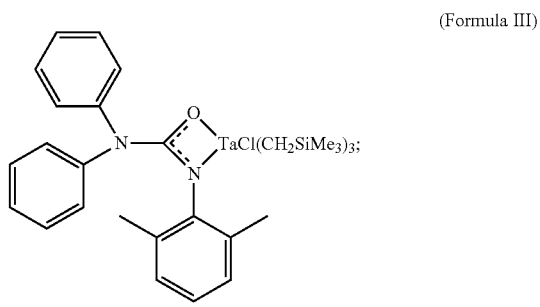

(Formula IV)

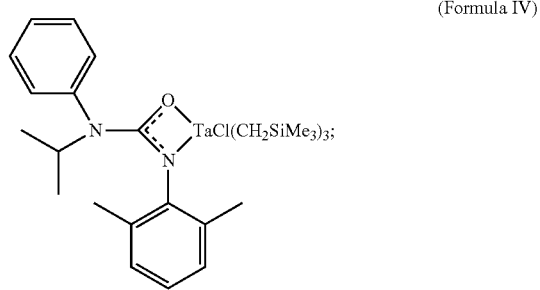

(Formula V)

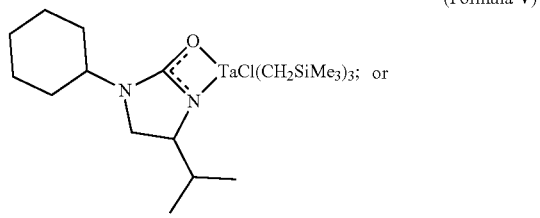

-continued (Formula VI)

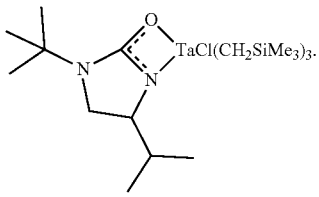

Aspects of this disclosure relate to a method for α-alkylation of a secondary amine-containing moiety with a polyolefin comprising at least one alkene group or, in other words, a method for amination of a polyolefin comprising at least one alkene group. The method comprises: (i) reacting the secondary amine-containing moiety with the polyolefin in the presence of a metal complex, which metal complex is:

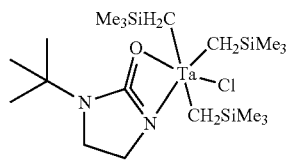

The secondary amine-containing moiety may include at least two α-sp³ hybridized C—H bonds.

The secondary amine-containing moiety may be a $C_4$-$C_{100}$ linear, branched, or cyclic alkyl, optionally substituted and/or comprising heteroatoms. The secondary amine-containing moiety may be substituted with a halogen, an ether, another amine, an alkyl, an alkene, an acetal, a phosphine, an amide, an alkyne, an imine, a nitrile, an isocyanide, an epoxide, a boronic acid ester; a phenyl that optionally may be substituted and/or part of a condensed ring system, or any combination thereof.

The olefin may include from 2 to 100 carbon atoms. In various embodiments, the olefin comprises an internal alkene. In various embodiments, the olefin is a linear or a cyclic olefin. In various embodiments, the olefin comprises a terminal alkene. In various embodiments, the olefin is an optionally substituted 1-alkene or an optionally substituted cycloalk-1-ene. In various embodiments, the olefin comprises one or more protected functional group(s). In various embodiments, the olefin is:

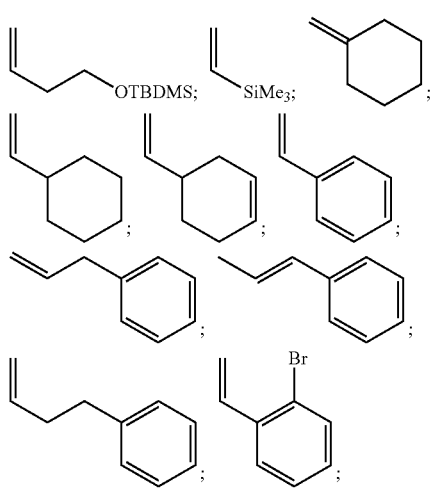

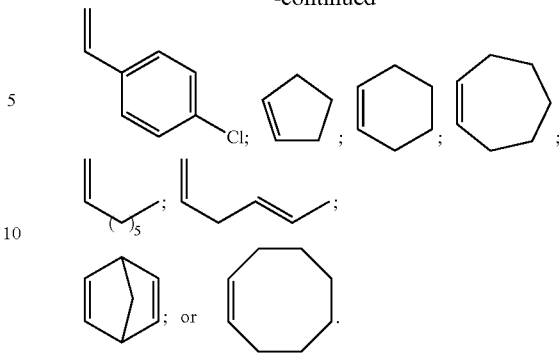

In various embodiments, the at least one alkene group comprises an internal alkene group. In various embodiments, the at least one alkene group comprises at least one vinyl group. In various embodiments, the at least one alkene group comprises at least one pendant alkene group. In various embodiments, the at least one pendant alkene group comprises a pendant vinyl group. In various embodiments, at least one pendant alkene group comprises —CH=CHCH₃, —CH=CHCH₂CH₃, or both. In various embodiments, the polyolefin is a vinyl-terminated polyolefin. In various embodiments, the polyolefin comprises a polypropylene. In various embodiments, the polyolefin comprises an atactic polypropylene. In various embodiments, the polyolefin comprises a copolymer poly(ethylene-co-propylene). In various embodiments, the polyolefin comprises polyethylene.

In various embodiments, the molecular weight of the polyolefin is in the range of about 100 g/mol to about 10,000 g/mol. In various embodiments, the molecular weight of the polyolefin is in the range of about 350 g/mol to about 3,500 g/mol. In various embodiments, the molecular weight of the polyolefin is in the range of about 1,500 g/mol to about 2,000 g/mol. In various embodiments, the molecular weight of the polyolefin is about 350 g/mol, about 400 g/mol, about 450 g/mol, about 500 g/mol, about 550 g/mol, about 600 g/mol, about 650 g/mol, about 700 g/mol, about 750 g/mol, about 800 g/mol, about 850 g/mol, about 900 g/mol, about 950 g/mol, about 1000 g/mol, about 1050 g/mol, about 1,100 g/mol, about 1150 g/mol, about 1200 g/mol, about 1250 g/mol, about 1300 g/mol, about 1350 g/mol, about 1400 g/mol, about 1450 g/mol, about 1500 g/mol, about 1550 g/mol, about 1600 g/mol, about 1650 g/mol, about 1700 g/mol, about 1750 g/mol, about 1800 g/mol, about 1850 g/mol, about 1900 g/mol, about 1950 g/mol, about 2000 g/mol, about 2050 g/mol, about 2100 g/mol, about 2150 g/mol, about 2200 g/mol, about 2250 g/mol, about 2300 g/mol, about 2350 g/mol, about 2400 g/mol, about 2450 g/mol, about 2500 g/mol, about 2550 g/mol, about 2600 g/mol, about 2650 g/mol, about 2700 g/mol, about 2750 g/mol, about 2800 g/mol, about 2850 g/mol, about 2900 g/mol, about 2950 g/mol, about 3000 g/mol, about 3050 g/mol, about 3100 g/mol, about 3150 g/mol, about 3200 g/mol, about 3250 g/mol, about 3300 g/mol, about 3350 g/mol, about 3400 g/mol, about 3450 g/mol, or about 3500 g/mol.

Aspects of the disclosure further relate to use of a group 5 metal salt of Formula VII $$MX_cR^4_d$$ (Formula VII)

wherein:
M is a group 5 metal;
c=1 to 5 and d=0 to 4, wherein the sum of c and d is 5; and
each $R^4$ is independently: H; or a $C_1$-$C_{20}$ substituted or unsubstituted, linear, branched or cyclic alkyl, optionally comprising heteroatoms,
in combination with an amide of Formula VIII

(Formula VIII)

wherein:
$R^1$ and $R^2$ are:
  each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
  bonded together thereby forming, together with the nitrogen atom they are both bound to, a heterocycle; and
$R^3$:
  is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
  bonded together with $R^1$ and/or $R^2$ to form a heterocycle.
for synthesizing a catalyst for α-alkylation of a secondary amine-containing moiety with a polyolefin having at least one alkene group or, in other words, for synthesizing a catalyst for aminating a polyolefin having at least one alkene group with a secondary amine-containing moiety. In various embodiments, the catalyst is a metal complex of Formula I,

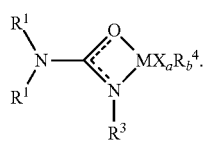

(Formula I)

wherein a=0 to 4 and b=0 to 4, wherein the sum of a and b is 4.

In various embodiments, the catalyst is a metal complex, wherein the metal complex is:

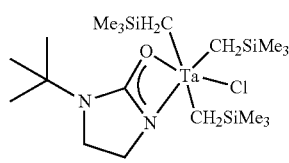

In various embodiments, the secondary amine-containing moiety is: pyrrolidine; piperidine;

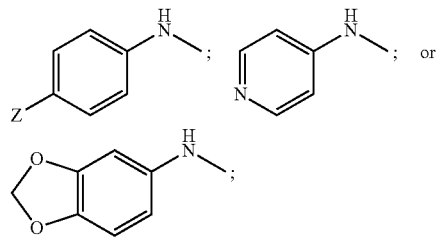

wherein Z is H, $OCF_3$, F, Cl, Br, I, or $OCH_3$.

In various embodiments, the secondary amine-containing moiety is:

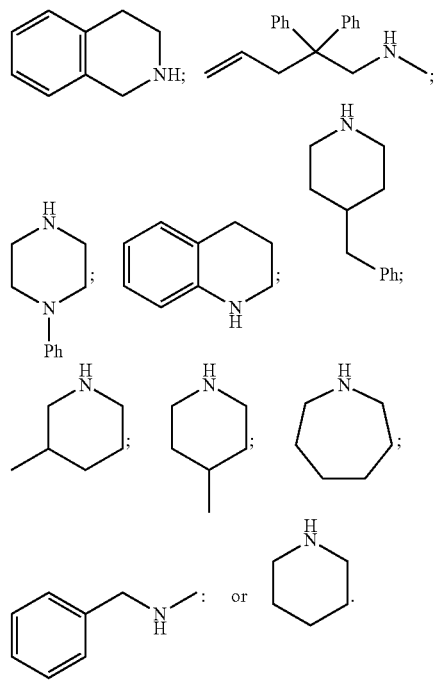

In various embodiments, the at least one alkene group comprises an internal alkene group. In various embodiments, the at least one alkene group comprises at least one vinyl group. In various embodiments, the at least one alkene group comprises at least one pendant alkene group. In various embodiments, the at least one pendant alkene group comprises a pendant vinyl group. In various embodiments, at least one pendant alkene group comprises —CH═$CHCH_3$, —CH═$CHCH_2CH_3$, or both. In various embodiments, the polyolefin is a vinyl-terminated polyolefin. In various embodiments, the polyolefin comprises a polypropylene. In various embodiments, the polyolefin comprises an atactic polypropylene. In various embodiments, the polyolefin comprises a copolymer poly(ethylene-co-propylene). In various embodiments, the polyolefin comprises polyethylene.

In various embodiments, the molecular weight of the polyolefin is in the range of about 100 g/mol to about 10,000 g/mol. In various embodiments, the molecular weight of the polyolefin is in the range of about 350 g/mol to about 3,500 g/mol. In various embodiments, the molecular weight of the polyolefin is in the range of about 1,500 g/mol to about 2,000 g/mol. In various embodiments, the molecular weight of the polyolefin is about 350 g/mol, about 400 g/mol, about 450 g/mol, about 500 g/mol, about 550 g/mol, about 600 g/mol, about 650 g/mol, about 700 g/mol, about 750 g/mol, about 800 g/mol, about 850 g/mol, about 900 g/mol, about 950 g/mol, about 1000 g/mol, about 1050 g/mol, about 1,100 g/mol, about 1150 g/mol, about 1200 g/mol, about 1250 g/mol, about 1300 g/mol, about 1350 g/mol, about 1400 g/mol, about 1450 g/mol, about 1500 g/mol, about 1550 g/mol, about 1600 g/mol, about 1650 g/mol, about 1700 g/mol, about 1750 g/mol, about 1800 g/mol, about 1850 g/mol, about 1900 g/mol, about 1950 g/mol, about 2000 g/mol, about 2050 g/mol, about 2100 g/mol, about 2150 g/mol, about 2200 g/mol, about 2250 g/mol, about 2300 g/mol, about 2350 g/mol, about 2400 g/mol, about 2450 g/mol, about 2500 g/mol, about 2550 g/mol, about 2600 g/mol, about 2650 g/mol, about 2700 g/mol, about 2750 g/mol, about 2800 g/mol, about 2850 g/mol, about 2900 g/mol, about 2950 g/mol, about 3000 g/mol, about 3050 g/mol, about 3100 g/mol, about 3150 g/mol, about 3200 g/mol, about 3250 g/mol, about 3300 g/mol, about 3350 g/mol, about 3400 g/mol, about 3450 g/mol, or about 3500 g/mol.

In various embodiments, the reaction conditions include a reaction temperature in the range from 50° C. to 200° C., a reaction temperature in the range from 75° C. to 165° C., a reaction temperature in the range from 90° C. to 150° C., a reaction temperature in the range from range from 110° C. to 130° C., a reaction temperature of about 110° C., or a reaction temperature of about 130° C.

In various embodiments, the reaction conditions include a solvent. The solvent may be non-protic. The solvent may be toluene, benzene, or a mixture thereof.

In various embodiments, the secondary amine-containing moiety and said olefin are provided in a stoichiometric ratio from 0.1 to 1.5. The secondary amine-containing moiety and said olefin may be provided in a stoichiometric ratio of about 1:1.

Aspects of the disclosure relate to a method of synthesizing a pharmaceutical compound or an agrochemical compound, the method comprising α-alkylation of a secondary amine-containing moiety according to a method as defined above and elsewhere herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Definitions

Figure 1:
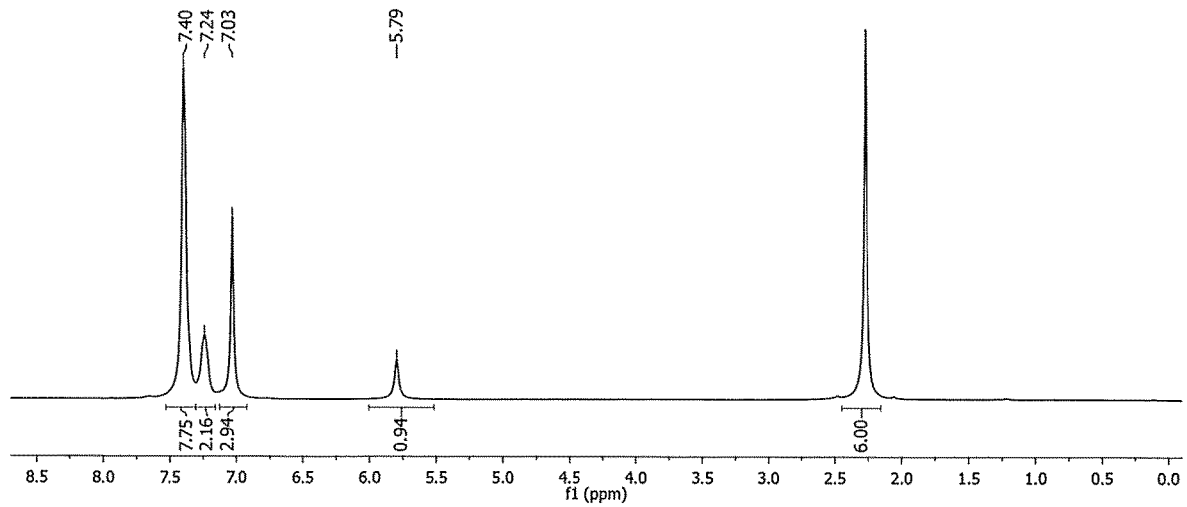
FIG. 1 is a $^1$H NMR spectrum (300 MHz, CDCl$_3$, 298 K) of 3-(2,6-dimethylphenyl)-1,1-diphenylurea.

"Catalyst", as used herein, refers to a chemical compound that accelerates a chemical reaction without itself being affected. "Catalyst" may be used interchangeably with terms such as "pre-catalyst", "catalyst system", or "catalytic system". "Catalyst", as used herein, includes catalytic intermediates or species formed in situ.

"Group 5 metal" as used herein, refers to the d-electron comprising transition metals listed in the periodic table of the elements as group 5, including transition metals vanadium (V), niobium (Nb), tantalum (Ta), and dubnium (Db).

"Atactic polypropylene", as used herein, refers to a polymer wherein the methyl group of the propylene units has no regular alignment.

"Copolymer", as used herein, refers to a polymer derived from more than one species of monomer.

"Hydroaminoalkylation", as used herein, refers to a reaction between a secondary amine containing moiety and an olefin. A catalyst may often be used to promote such reaction.

"Secondary amine", as used herein, refers to an amine in which the amino group is directly bonded to two C-atoms of any hybridization. The two C-atoms in α-position to the N-atom may be spa hybridized.

"Olefin" or "alkene", as used herein, refers to an unsaturated hydrocarbon containing one or more pairs of C-atoms linked by a double bond.

"TOF", as used herein, refers to "turnover frequency".

"Vinyl", as used herein, refers to a functional group with the formula —CH=CH$_2$.

A "pendant" group, as used herein, refers to a side group (or offshoot) from the main chain (or backbone) of a polyolefin.

Throughout this specification, unless the context requires otherwise, the words "comprise", "comprising" and the like, are to be construed in an inclusive sense as opposed to an exclusive sense, that is to say, in the sense of "including, but not limited to".

This disclosure relates to the discovery that rapid C—H alkylation of unprotected secondary arylamines with unactivated alkenes, particularly pendant and terminal alkene groups of polyolefins, can be achieved with metal complex catalysts comprising a combination of a tantalum (Ta) organometallic reagent (e.g. Ta(CH$_2$SiMe$_3$)$_3$Cl$_2$) and a ureate N, O chelating-ligand salt.

Materials and Methods

The procedures described herein are given for the purposes of example and illustration only and should not be considered to limit the spirit or scope of the invention.

1. Materials

All reactions were performed under a N$_2$ atmosphere using Schlenk or glovebox techniques, unless otherwise stated. TaCl$_5$ (Strem), Ta(NMe$_2$)$_5$ (Strem), and (chloromethyl)trimethylsilane (Sigma) were used as received. NaN (SiMe$_3$)$_2$ (Sigma) was recrystallized from a hot toluene solution before use. All amines and alkenes were commercially available, dried over CaH$_2$ and distilled and degassed prior to use in catalytic experiments. [Ta(NMe$_2$)$_3$Cl$_2$]2, TaMe$_3$Cl$_2$, Ta(CH$_2$CMe$_3$)$_3$Cl$_2$, and Ta(CH$_2$SiMe$_3$)$_3$Cl$_2$ were synthesized according to literature protocols (Chem. Int. Ed. 48, 4892-4894; Synthesis 46, 2884-2896; Chem. Res 48: 2576-2586; Inorg. Chem. 20: 1859-1866; J. Am. Chem. Soc. 100: 2389-2399; Dalton Trans. 40, 7777-7782). All glassware was dried in a 180° C. oven overnight before use. Toluene, hexanes and Et$_2$O were dried over an activated alumina column and stored over activated molecular sieves (4 Å). d$_8$-Benzene and do-toluene were dried over sodium/ketyl and distilled prior to use. Experiments conducted on NMR tube scale were performed in J. Young NMR tubes (8"×5 mm) sealed with screw-type Teflon caps.

2. Instrumentation $^1$H and $^{13}$C NMR spectra were recorded on Bruker 300 MHz, or 400 MHz, Avance spectrometers at ambient temperature. Chemical shifts (δ) are given relative to the corresponding residual protio solvent and are reported in parts per million (ppm). Coupling constants J are given in Hertz (Hz). The following abbreviations are used to indicate signal multiplicity: s=singlet, d=doublet, t=triplet, q=quartet, m=multiplet, and br=broad.

Assignment of the signals was carried out using 1D ($^1$H, $^{13}$C{$^1$H}) and 2D (COSY, HSQC and HMBC) NMR experiments.

3. Synthesis

3.1 Proligands

Figure 42:
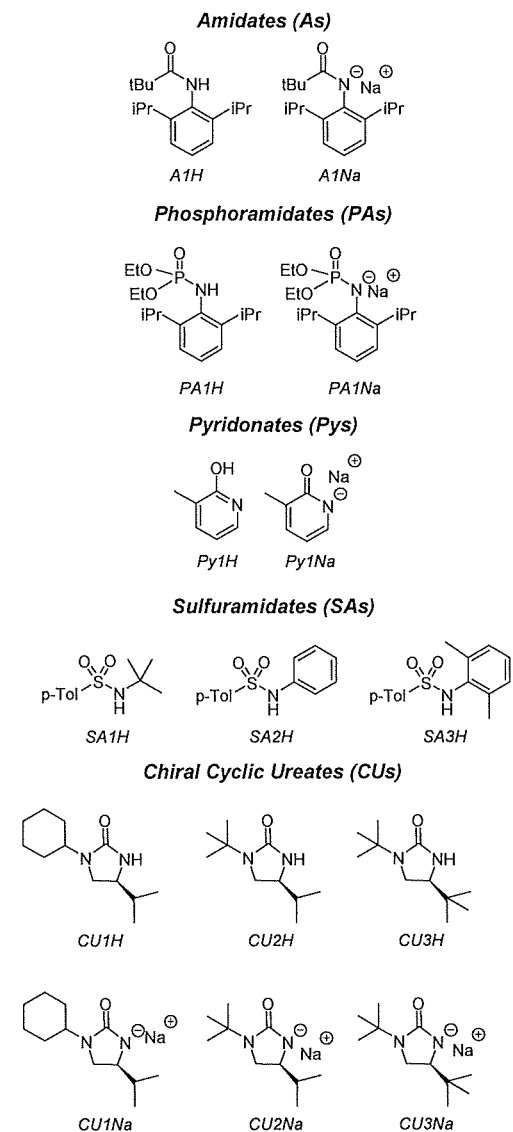
FIG. 42 is a legend of all ligands prepared and investigated in the study disclosed herein.
Figure 42:
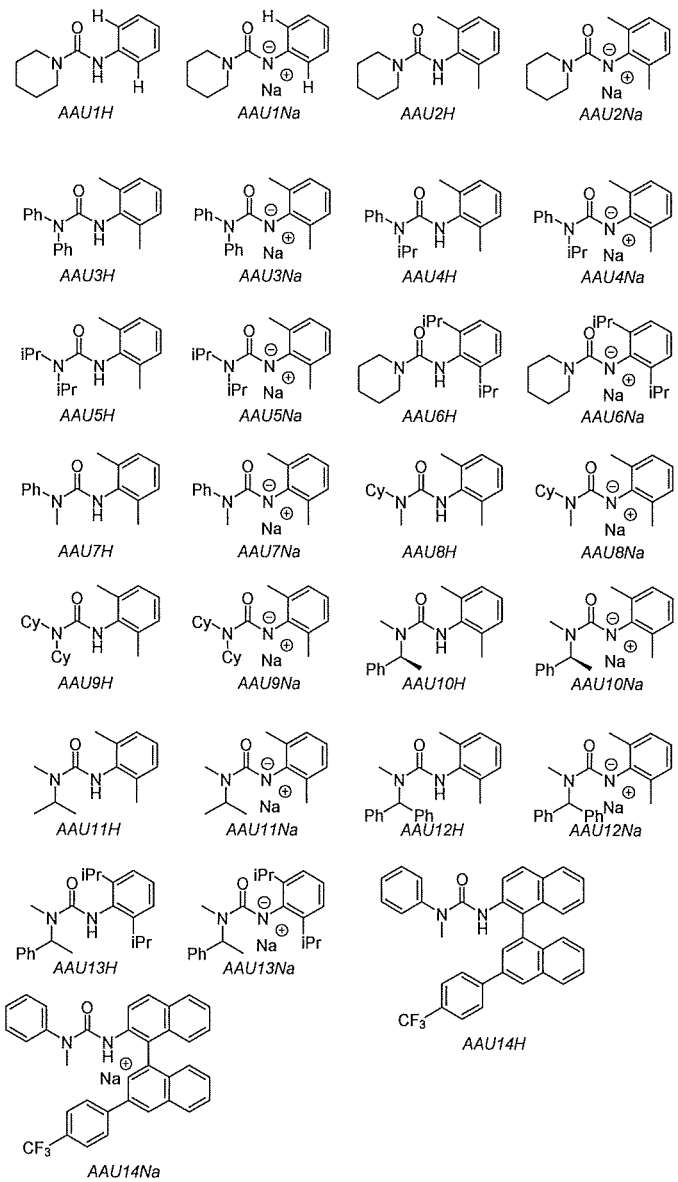
Figure 42:
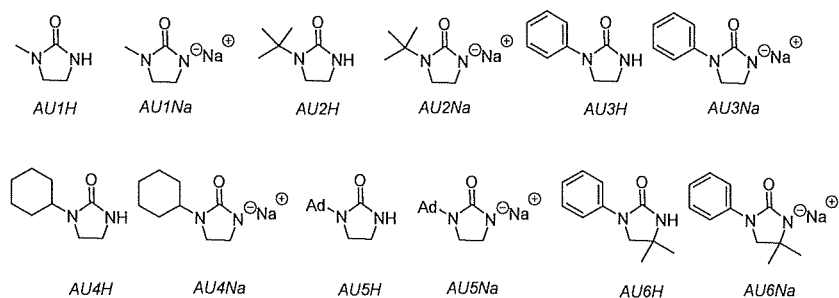

The synthesis of proligands is generally discussed below, with reference to particular exemplified proligands. FIG. 42 summarizes the proligands synthesized and disclosed herein.

General procedure for the synthesis of urea proligands: Urea proligands were prepared following a modified literature procedure[3] in which the aniline (1 equiv) was dissolved in DCM and the solution was cooled to 0° C. Triphosgene (0.35 equiv) was added in one portion. The solution was stirred for five minutes after which N,N-diisopropylethylamine (2 equiv) was added and the cold bath removed. The solution was stirred for 1 hour and then piperidine (1 equiv) and a second portion of N,N-diisopropylethylamine (1 equiv) were added. The solution was stirred for an additional hour, and then diluted with 1 M HCl. The organic phase was washed three times with 1 M HCl dried over MgSO$_4$, filtered, and concentrated by rotary evaporation.

Synthesis of 3-(2,6-dimethylphenyl)-1,1-diphenylurea

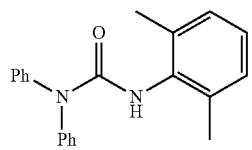 [SMILES: Cc1cccc(C)c1NC(=O)N(c1ccccc1)c1ccccc1]

Prepared following the general procedure outlined above. Recrystallization provided the desired compound as a white solid (1.2 g, Unoptimized Synthesis): $^1$H NMR (CDCl$_3$, 300 MHz, 298 K): δ 7.42-7.38 (overlapping m, 8H, o-C$_6$H$_5$ and m-C$_6$H$_5$), 7.29-7.18 (m, 2H, p-C$_6$H$_5$), 7.05 (s, 3H, 2,6-Me$_2$C$_6$H$_3$), 5.79 (NH), 2.27 (s, 6H, CH$_3$) ppm. $^{13}$C NMR (CDCl$_3$, 75 MHz, 298 K): δ 153.94 (C=O), 142.72 (i-C$_6$H$_5$), 135.68 (o-C$_6$H$_3$), 134.56 (i-C$_6$H$_3$), 129.53 (m-C$_6$H$_5$), 128.12 (m-C$_6$H$_3$), 127.28 (o-C$_6$H$_5$), 126.85 (p-C$_6$H$_5$), 126.40 (p-C$_6$H$_3$), 18.62 (CH$_3$) ppm.

Figure 2:
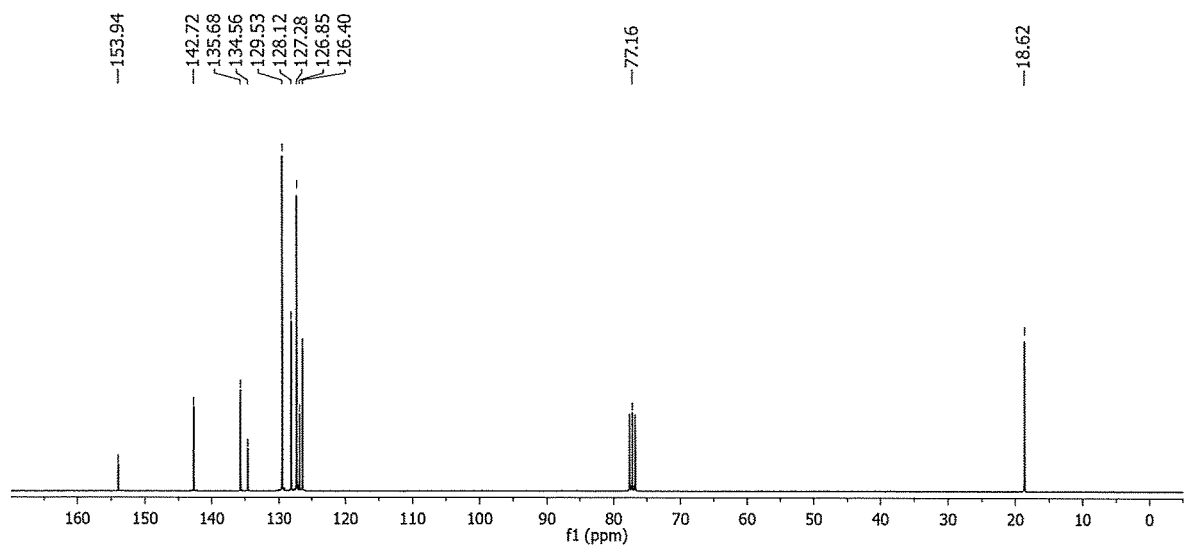
FIG. 2 is a $^{13}$C NMR spectrum (75 MHz, CDCl$_3$, 298 K) of 3-(2,6-dimethylphenyl)-1,1-diphenylurea.

A $^1$H NMR spectrum (300 MHz, CDCl$_3$, 298 K) of 3-(2,6-dimethylphenyl)-1,1-diphenylurea is shown in FIG. 1. A $^{13}$C NMR spectrum (75 MHz, CDCl$_3$, 298 K) of 3-(2,6-dimethylphenyl)-1,1-diphenylurea is shown in FIG. 2.

Synthesis of 3-(2,6-dimethylphenyl)-1-isopropyl-1-phenylurea

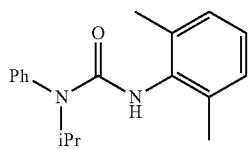 [SMILES: Cc1cccc(C)c1NC(=O)N(c1ccccc1)C(C)C]

Prepared following the general procedure outlined above. Recrystallization provided the desired compound as a white solid (1.1 g, Unoptimized Synthesis): $^1$H NMR (CDCl$_3$, 400 MHz, 298 K): δ 7.61-7.28 (overlapping m, 5H, o,m,p-C$_6$H$_5$), 6.99 (s, 3H, C$_6$H$_3$), 5.24 (NH), 4.96 (hept, $^3J_{H-H}$=6.5 Hz, 1H, CH(CH$_3$)$_2$), 2.19 (s, 6H, 2,6-(CH$_3$)$_2$C$_6$H$_3$), 1.14 (d, $^3J_{H-H}$=6.2 Hz, 6H, CH(CH$_3$)$_2$) ppm. $^{13}$C NMR (CDCl$_3$, 101 MHz, 298 K): 154.62 (C=O), 138.17 (i-C$_6$H$_5$), 135.71 (o-C$_6$H$_3$), 135.18 (i-C$_6$H$_3$), 131.21 (m-C$_6$H$_3$), 129.83 (o-C$_6$H$_5$), 128.66 (p-C$_6$H$_5$), 127.94 (m-C$_6$H$_3$), 126.38 (p-C$_6$H$_3$), 46.58 (CH(CH$_3$)$_2$), 21.65 (CH(CH$_3$)$_3$), 18.47 (2,6-(CH$_3$)$_2$C$_6$H$_3$) ppm.

Figure 3:
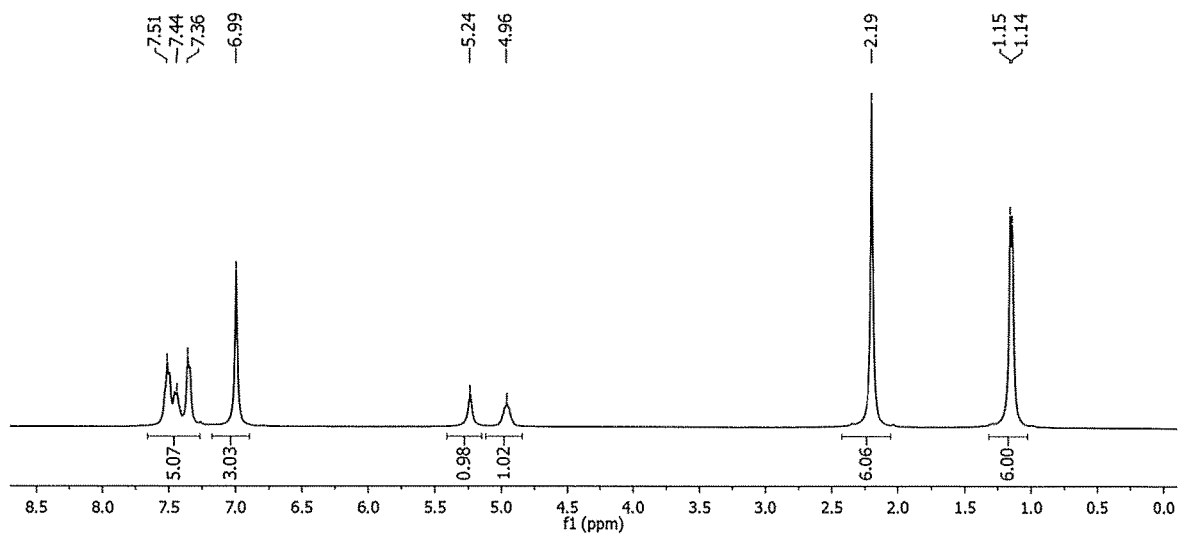
FIG. 3 is a $^1$H NMR spectrum (300 MHz, CDCl$_3$, 298 K) of 3-(2,6-dimethylphenyl)-1-isopropyl-1-phenylurea.
Figure 4:
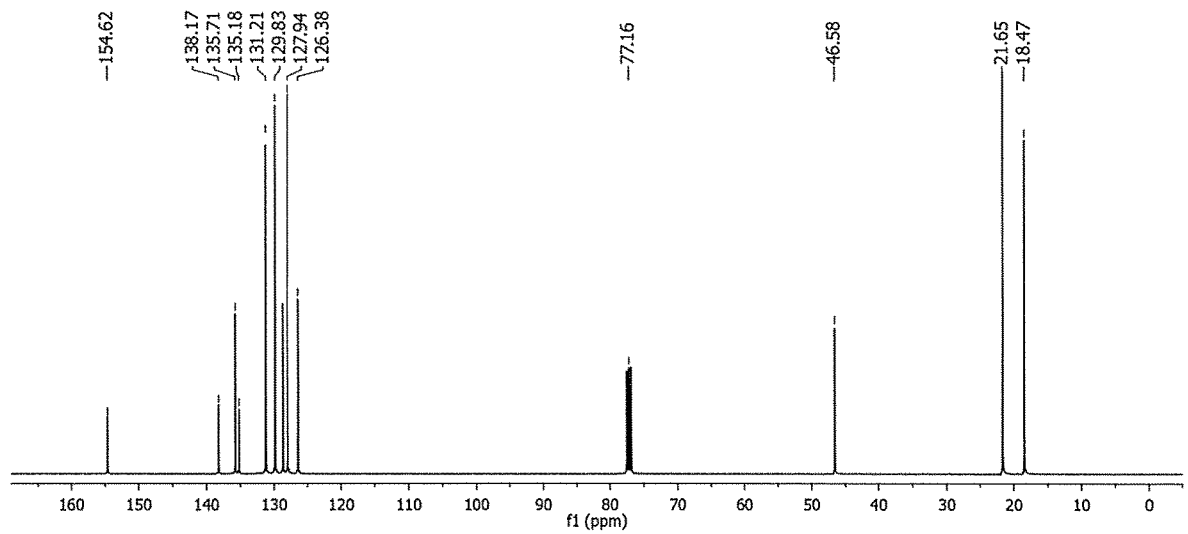
FIG. 4 is a $^{13}$C NMR spectrum (75 MHz, CDCl$_3$, 298 K) of 3-(2,6-dimethylphenyl)-1-isopropyl-1-phenylurea.

A $^1$H NMR spectrum (300 MHz, CDCl$_3$, 298 K) of 3-(2,6-dimethylphenyl)-1-isopropyl-1-phenylurea is shown in FIG. 3. A $^{13}$C NMR spectrum (75 MHz, CDCl$_3$, 298 K) of 3-(2,6-dimethylphenyl)-1-isopropyl-1-phenylurea.

Cyclic Ureate Ligands

Synthesis and Characterization of Cyclic Ureate Proligands

Scheme 1. General synthesis of cyclic ureate proligands

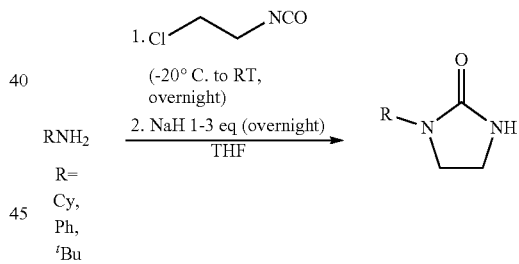

Synthesis of 1-cyclohexylimidazolidin-2-one ($^{Cy}$LH)

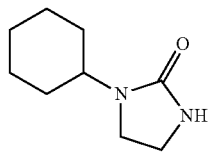 [SMILES: O=C1NCCN1C1CCCCC1]

A solution 2-chloroethyl isocyanate (1.11 g, 10.5 mmol) in THF (50 mL) was added dropwise to a stirring solution of cyclohexylamine (0.99 g, 10 mmol) in THF (20 mL) at room temperature. The resulting reaction mixture was treated with NaH (0.24 g, 10 mmol) under an inert atmosphere and stirred at room temperature overnight under an inert atmosphere. The mixture was treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and concentrated under vacuum to form a colorless suspension in EtOAc. The reaction mixture was filtered and the resulting solid was dried to form the desired product. Yield (0.44 g, 27%). $^1$H NMR (CDCl$_3$, 300 MHz, 298 K): δ 5.41 (br s, 1H, NH), 3.77-3.58 (m, 1H, NCH), 3.43 (s, 4H, CH$_2$CH$_2$NH), 1.92-1.52 (m, 11H, HNCH$_2$) ppm. $^{13}$C NMR (CDCl$_3$, 75 MHz, 298 K): δ 162.52 (C=O), 40.71 ($^{tBu}$NCH$_2$), 51.15 (CH), 38.76 (HNCH$_2$), 30.39 ($^{Cy}$CH$_2$), 25.64 ($^{Cy}$CH$_2$) ppm. HRMS (ESI): m/z calcd for C$_9$H$_{16}$N$_2$ONa [M+Na$^+$]: 191.1160. Found: 191.1159.

Figure 22:
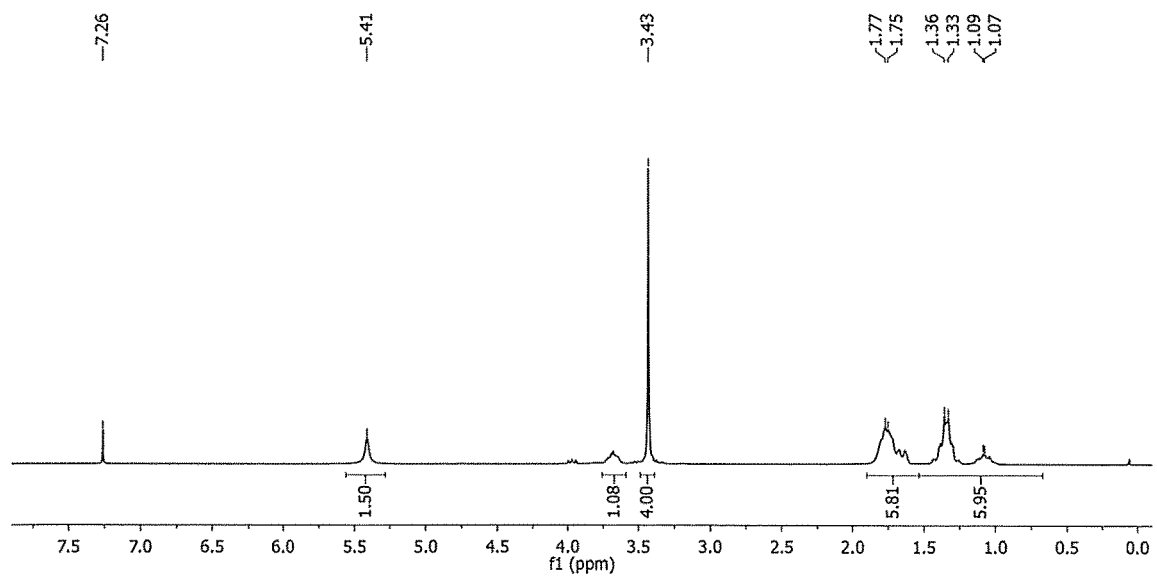
FIG. 22 is a $^1$H NMR spectrum (300 MHz, CDCl$_3$, 298 K) of 1-cyclohexylimidazolidin-2-one ($^{Cy}$LH).
Figure 23:
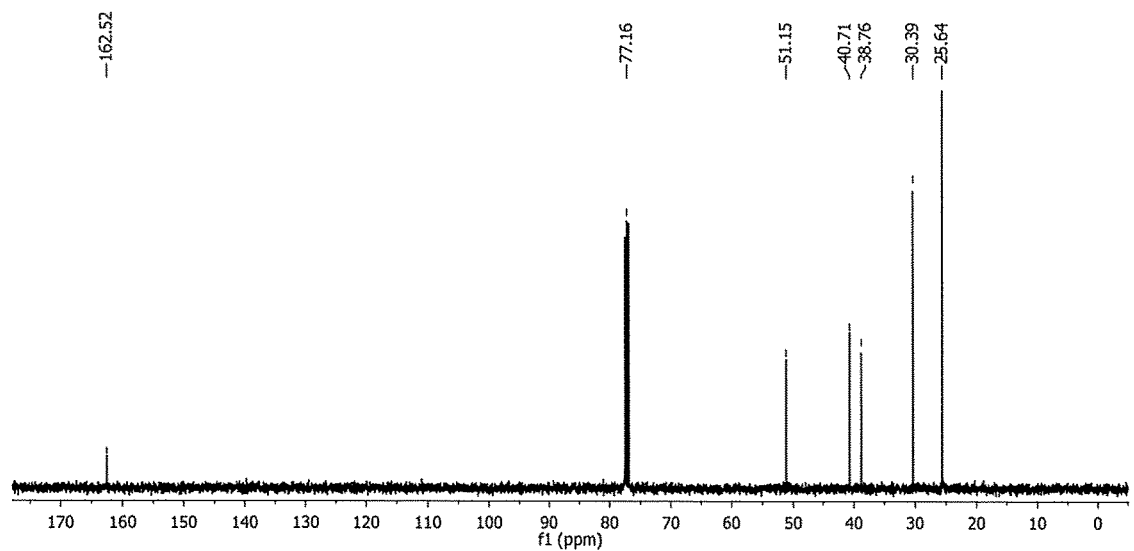
FIG. 23 is a $^{13}$C NMR spectrum (100 MHz, CDCl$_3$, 298 K) of 1-cyclohexylimidazolidin-2-one ($^{Cy}$LH).

FIG. 22 is a $^1$H NMR spectrum (300 MHz, CDCl$_3$, 298 K) of 1-cyclohexylimidazolidin-2-one ($^{Cy}$LH). FIG. 23 is a $^{13}$C NMR spectrum (100 MHz, CDCl$_3$, 298 K) of 1-cyclohexylimidazolidin-2-one ($^{Cy}$LH).

Synthesis of 1-phenylimidazolidin-2-one ($^{Ph}$LH)

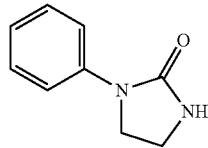 [SMILES: O=C1NCCN1c1ccccc1]

A solution 2-chloroethyl isocyanate (1.05 g, 10 mmol) in THF (50 mL) was added dropwise to a stirring solution of phenylamine (0.93 g, 10 mmol) in THF (20 mL) at −20° C. The solution was brought to room temperature overnight. The resulting reaction mixture was treated with NaH (0.24 g, 10 mmol) under an inert atmosphere and stirred at room temperature overnight. The mixture was treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and concentrated under vacuum to form a colorless suspension in EtOAc. The reaction mixture was filtered and the resulting solid was dried to form the desired product. Yield (0.42 g, 26%). $^1$H NMR (CDCl$_3$, 300 MHz, 298 K): δ 7.58 (d, 2H, J$_{H-H}$=8.2 Hz, m-C$_6$H$_5$), 7.38-7.29 (m, 2H, o-C$_6$H$_5$), 7.05 (t, 2H, J$_{H-H}$=7.2 Hz, p-C$_6$H$_5$), 4.00-3.84 (m, 2H, $^{Ph}$NCH$_2$), 3.65-3.48 (m, 2H, HNCH$_2$) ppm. $^{13}$C NMR (CDCl$_3$, 75 MHz, 298 K): δ 160.27 (C=O), 140.18 (C$_6$H$_5$), 128.92 (C$_6$H$_5$), 122.83 (C$_6$H$_5$), 118.09 (C$_6$H$_5$), 45.49 ($^{Ph}$NCH$_2$), 37.70 (HNCH$_2$) ppm. HRMS (ESI): m/z calcd for C$_9$H$_{10}$N$_2$ONa [M+Na$^+$]: 185.0691. Found: 185.0691.

Figure 24:
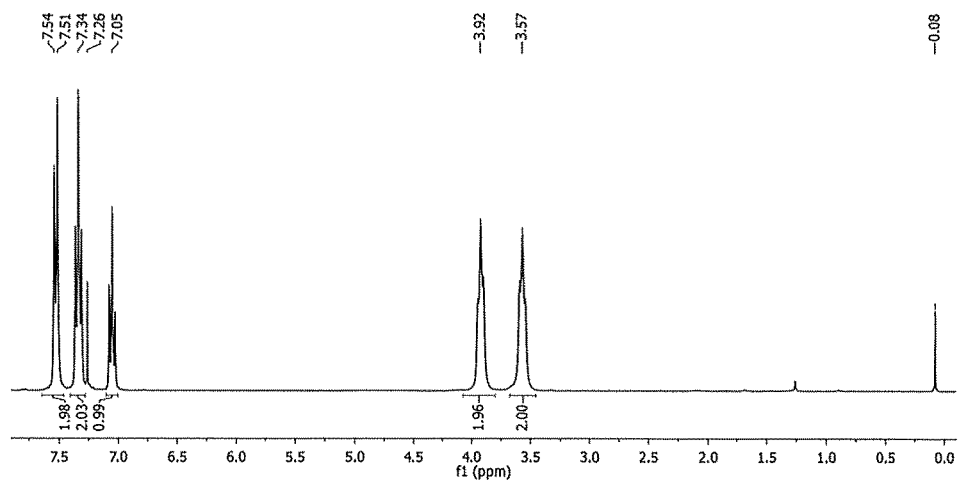
FIG. 24 is a $^1$H NMR spectrum (300 MHz, CDCl$_3$, 298 K) of 1-phenylimidazolidin-2-one ($^{Ph}$LH).
Figure 25:
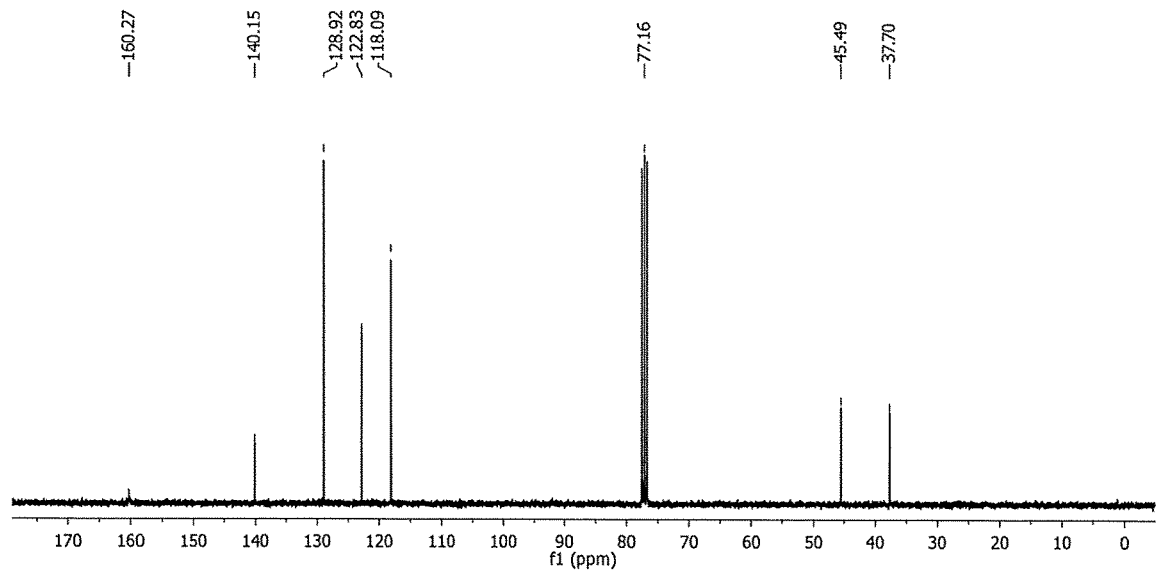
FIG. 25 is a $^{13}$C NMR spectrum (75 MHz, CDCl$_3$, 298 K) of 1-phenylimidazolidin-2-one ($^{Ph}$LH).

FIG. 24 is a $^1$H NMR spectrum (300 MHz, CDCl$_3$, 298 K) of 1-phenylimidazolidin-2-one ($^{Ph}$LH). FIG. 25 is a $^1$H NMR spectrum (75 MHz, CDCl$_3$, 298 K) of 1-phenylimidazolidin-2-one ($^{Ph}$LH).

Synthesis of 1-(tert-butyl)imidazolidin-2-one ($^{tBu}$LH)

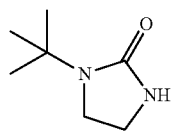

A solution 2-chloroethyl isocyanate (6.80 g, 64 mmol) in THF (50 mL) was added dropwise to a stirring solution of tertbutylamine (4.28 g, 58.5 mmol) in THF (20 mL) at −20° C. The solution was brought to room temperature overnight. The resulting reaction mixture was treated with NaH (6.8 g, 283 mmol) under an inert atmosphere and heated at 65° C. overnight under an inert atmosphere. The mixture was brought to dryness and treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and brought to dryness under vacuum forming a yellow oil. Hexanes (5 mL) were then added resulting with the formation of a solid at the bottom of the round bottom flask. The mother liquor was removed by filtration. This process was repeated 3 more times and the combined hexane solutions (fraction 1) were stored at −30° C. overnight, while the solid (fraction 2) was also kept. Storing the combined hexane solutions (fraction 1) at low temperatures resulted in the formation of colorless crystals that were later filtered and dried in vacuo to afford 350 mg of pure product. The solid from fraction 2 was sublimed at 100° C. under vacuum to afford a waxy solid on the cold finger. The resulting waxy solid was washed with hexanes (2×4 mL) to afford 770 mg of pure product. Total yield: 1.12 g (13%). $^1$H NMR (CDCl$_3$, 300 MHz, 298 K): δ 4.37 (br s, 1H, NH), 3.49-3.40 (m, 2H, $^{tBu}$NCH$_2$), 3.33-3.23 (m, 2H, HNCH$_2$), 1.36 (s, 9H, C(CH$_3$)$_3$) ppm. $^{13}$C NMR (CDCl$_3$, 75 MHz, 298 K): δ 163.15 (C=O), 52.96 (C(CH$_3$)$_3$), 43.73 ($^{tBu}$NCH$_2$), 38.13 (HNCH$_2$), 27.67 (C(CH$_3$)$_3$) ppm. HRMS (ESI): m/z calcd for C$_7$H$_{14}$N$_2$O [M+Na$^+$]: 165.10039. Found: 165.1001. Anal. Calcd. for C$_7$H$_{14}$N$_2$O: C, 59.12; H, 9.92; N, 19.70; Found: C, 59.12; H, 10.29; N, 19.71.

Figure 26:
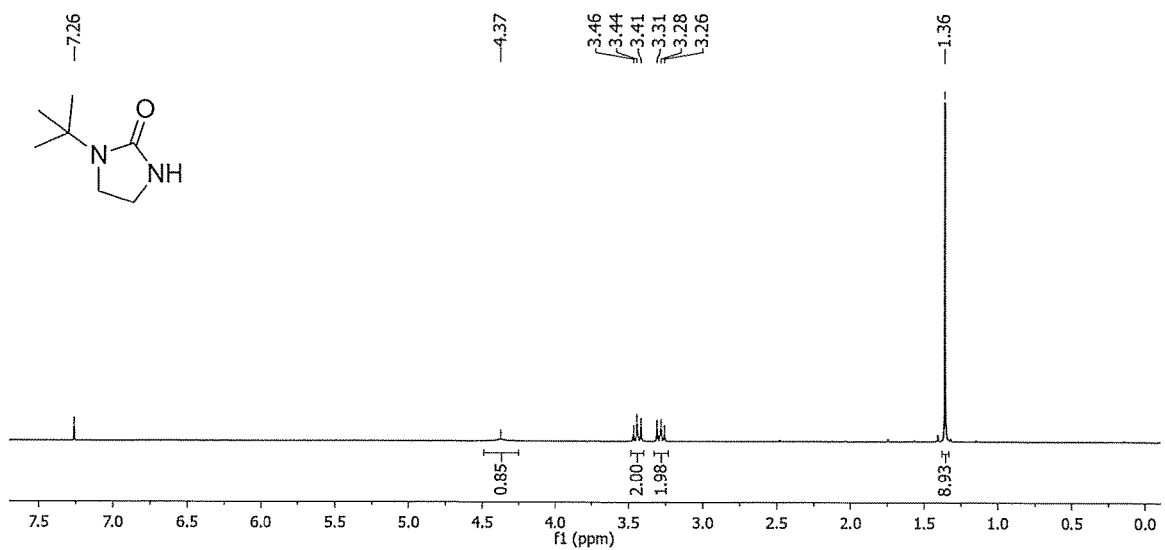
FIG. 26 is a $^1$H NMR spectrum (300 MHz, CDCl$_3$, 298 K) of 1-(tert-butyl)imidazolidin-2-one ($^{tBu}$LH).
Figure 27:
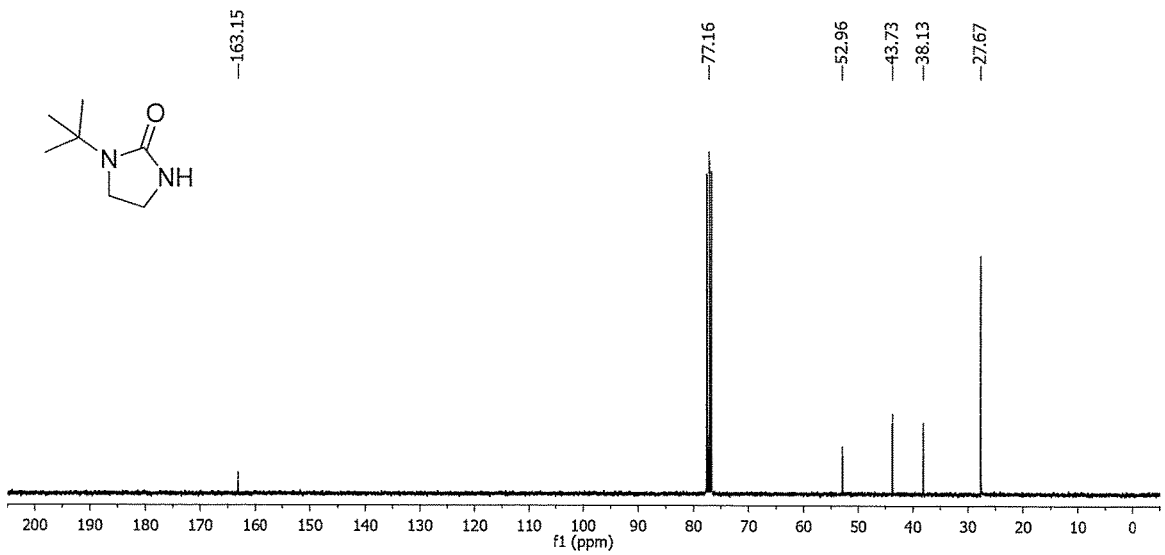
FIG. 27 is a $^{13}$C NMR spectrum (75 MHz, CDCl$_3$, 298 K) of 1-(tert-butyl)imidazolidin-2-one ($^{tBu}$LH).

FIG. 26 is a $^1$H NMR spectrum (300 MHz, CDCl$_3$, 298 K) of 1-(tert-butyl)imidazolidin-2-one ($^{tBu}$LH). FIG. 27 is a $^{13}$C NMR spectrum (75 MHz, CDCl$_3$, 298 K) of 1-(tert-butyl)imidazolidin-2-one ($^{tBu}$LH).

Synthesis of Cyclic Ureate Ligand Salts

General procedure for the synthesis of ligand salts $^X$LH (X=Me, Cy, Ph, $^t$Bu): NaN(SiMe$_3$)$_2$ (1 equiv.) and the corresponding proteoligand (1 equiv.) were mixed in toluene (~5 mL) and stirred overnight at room temperature. The volatiles were then removed at low pressure and the resulting solid was thoroughly stripped with hexanes (3×5 mL) and dried to give the sodium salt in moderate to quantitative yields as a colorless powder. The resulting ligand salts were used directly without further purification via storage in a glove box. Except in the case of $^{Dipp}$LH, NMR characterization was precluded due to poor solubility in common NMR solvents (e.g. d$_6$-benzene or de-toluene).

Synthesis of sodium 3-methyl-2-oxoimidazolidin-1-ide ($^{Me}$L$^-$Na$^+$)

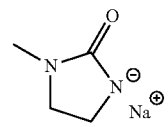

Prepared following the general procedure outlined above: $^{Me}$LH (197 mg, 1.97 mmol) and NaN(SiMe$_3$)$_2$ (361 mg, 1.97 mmol). Yield (163 mg, 68%).

Synthesis of sodium 3-cyclohexyl-2-oxoimidazolidin-1-ide ($^{Cy}L^-Na^+$)

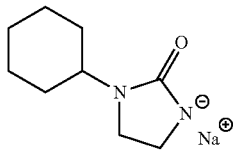 [SMILES: O=C1[N-]CCN1C1CCCCC1 ; [Na+]]

Prepared following the general procedure outlined above: $^{Cy}LH$ (100 mg, 0.59 mmol) and NaN(SiMe$_3$)$_2$ (109 mg, 0.59 mmol). Yield (107 mg, 95%).

Synthesis of sodium 2-oxo-3-phenylimidazolidin-1-ide ($^{Ph}L^-Na^+$)

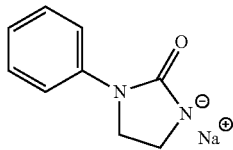 [SMILES: O=C1[N-]CCN1c1ccccc1 ; [Na+]]

Prepared following the general procedure outlined above: $^{Ph}LH$ (150 mg, 0.93 mmol) and NaN(SiMe$_3$)$_2$ (170 mg, 0.93 mmol). Yield (140 mg, 82%).

Synthesis of sodium 3-(tert-butyl)-2-oxoimidazolidin-1-ide ($^{tBu}L^-Na^+$)

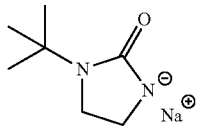

Prepared following the general procedure outlined above: $^{tBu}L^-Na^+$ (230 mg, 1.62 mmol) and NaN(SiMe$_3$)$_2$ (297 g, 1.62 mmol). Yield (265 mg, 99%).

Acyclic Ureate Ligands

Synthesis and Characterization of Proteoligands

General procedure for the synthesis of urea based proteoligands: Prepared following a modified literature procedure in which a chosen primary amine (1 equiv.) was dissolved in dichloromethane and the solution was cooled to 0° C. Triphosgene (0.35 equiv.) was added in portions as a solid. The solution was stirred for five minutes after which N,N-diisopropylethylamine DIPEA (3 equiv.) was added and the cold bath removed. The solution was stirred for 1 hour and then the appropriate amine (1 equiv.) and a second portion of DIPEA (1 equiv.) was added. The solution was stirred for an additional hour, and then diluted with 3 M HCl. The organic phase was washed three times with 1 M HCl dried over MgSO$_4$, filtered, and concentrated by rotary evaporation to give the crude product.

Synthesis of 3-(2,6-dimethylphenyl)-1-methyl-1(1-phenylethyl)urea

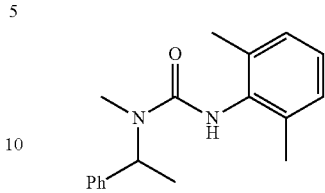

Prepared following the general procedure outlined above: 2,6-dimethylaniline (2.25 g, 18.5 mmol), triphosgene (1.81 g, 6.10 mmol), DIPEA (7.2 g, 55.5 mmol), N-methyl-1-phenylethan-1-amine (2.5 g, 18.5 mmol). Recrystallization from a concentrated ethyl acetate solution provided the desired compound as a white solid (3.48 g, 66.9%): $^1$H NMR (CDCl$_3$, 300 MHz, 298 K): δ 7.41-7.26 (overlapping m, 5H, o-C$_6$H$_5$ m-C$_{61}$-16, and p-C$_6$H$_5$), 7.04 (s, 3H, m-C$_6$H$_6$, and p-C$_6$H$_5$), 5.86 (br s, 1H, NH), 5.64-5.57 (q, 1H, CHCH$_3$), 2.79 (s, 3H, CH$_3$), 2.19 (s, 6H, 2,6-(CH$_3$)$_2$C$_6$H$_3$) ppm. $^{13}$C NMR (CDCl$_3$, 75 MHz, 298 K): δ 156.31 (C=O), 141.79, 135.58, 135.33, 128.64, 128.07, 127.28, 126.88, 126.34, 52.80, 29.53, 18.43, 17.02 ppm. HRMS (ESI): m/z calcd for C$_{18}$H$_{23}$N$_2$O [M+H$^+$]: 283.1810. Found: 283.1809.

Figure 33:
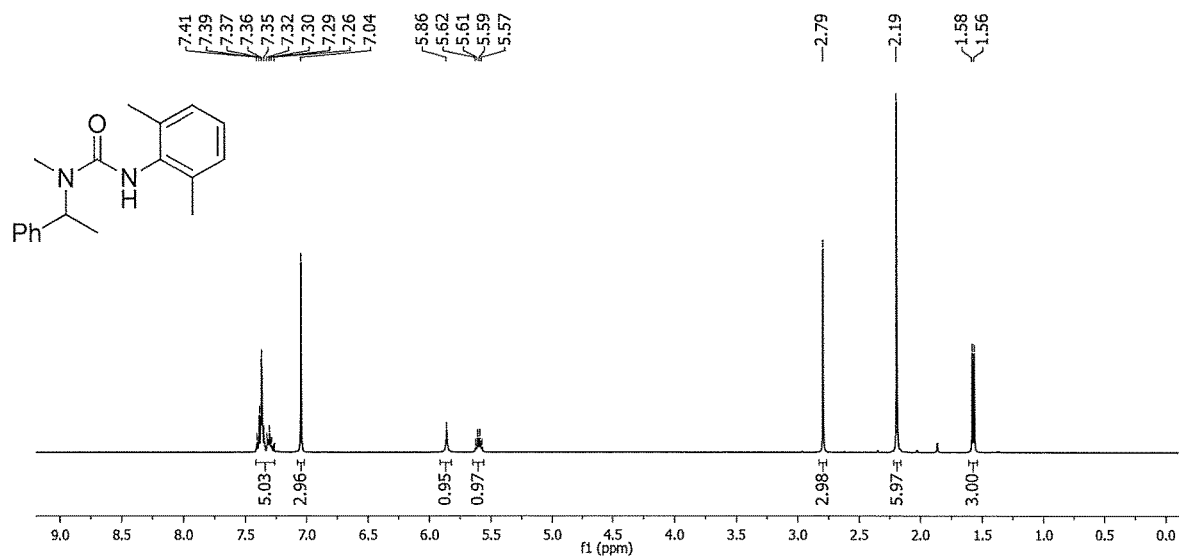
FIG. 33 is a $^1$H NMR spectrum (400 MHz, CDCl$_3$, 298 K) of 3-(2,6-dimethylphenyl)-1-methyl-1-(1-phenylethyl)urea.
Figure 34:
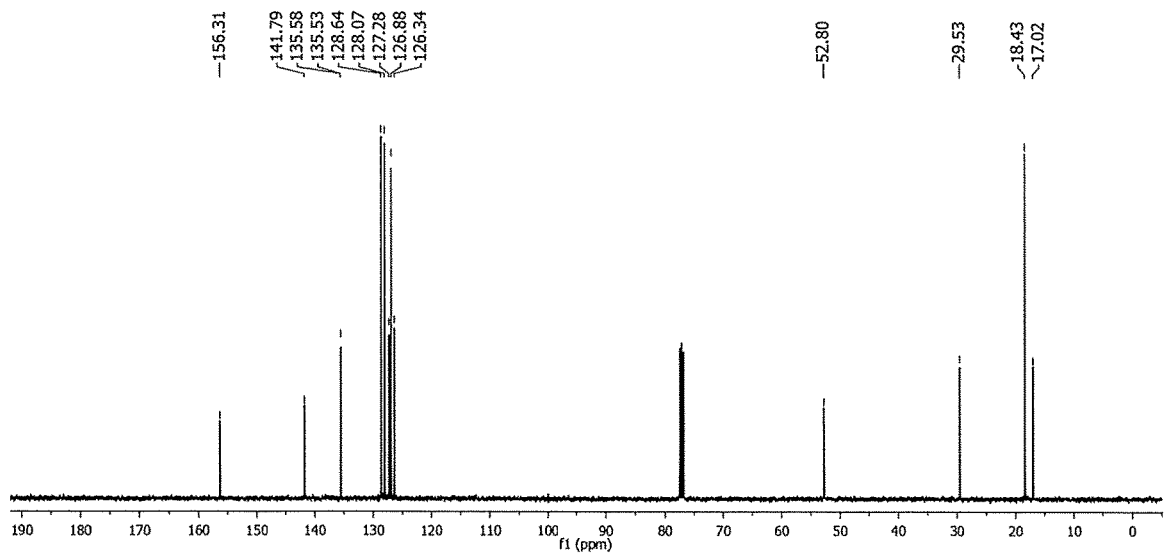
FIG. 34 is a $^{13}$C NMR spectrum (100 MHz, benzene-dB, 298 K) of 3-(2,6-dimethylphenyl)-1-methyl-1-(1-phenylethyl)urea.

FIG. 33 is a $^1$H NMR spectrum (400 MHz, CDCl$_3$, 298 K) of 3-(2,6-dimethylphenyl)-1-methyl-1-(1-phenylethyl)urea. FIG. 34 is a $^{13}$C NMR spectrum (100 MHz, benzene-d$_6$, 298 K) of 3-(2,6-dimethylphenyl)-1-methyl-1-(1-phenylethyl)urea.

Synthesis of 3-(2,6-dimethylphenyl)-1-isopropyl-1-phenylurea

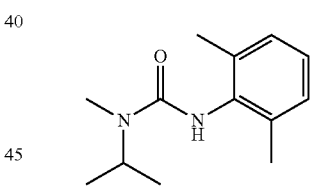

Prepared following the general procedure outlined above: 2,6-dimethylaniline (1.5 g, 20.5 mmol), triphosgene (2.02 g, 7.41 mmol), DIPEA (7.95 g, 61.5 mmol), N-isopropylaniline (2.5 g, 20.5 mmol). Recrystallization from a concentrated ethyl acetate solution provided the desired compound as a white solid (3.20 g, 65%): $^1$H NMR (CDCl$_3$, 400 MHz, 298 K): δ 7.05 (s, 3H, o,m,p-C$_6$H$_5$), 5.69 (br s, 1H, NH), 4.56-4.49 (m, 1H, CH(CH$_3$)$_2$), 2.86 (s, 3H, CH$_3$), 2.24 (s, 6H, 2,6-(CH$_3$)$_2$C$_6$H$_3$), 1.17 (d, J$_{H-H}$=1.7 Hz, 6H, CH(CH$_3$)$_2$) ppm. $^{13}$C NMR (CDCl$_3$, 101 MHz, 298 K): δ 156.00 (C=O), 135.70, 135.57, 128.20, 126.40, 45.89, 27.45, 20.21, 18.56 ppm. HRMS (ESI): m/z calcd for C$_{13}$H$_{21}$N$_2$O [M+H$^+$]: 221.1654. Found: 221.1656.

Figure 35:
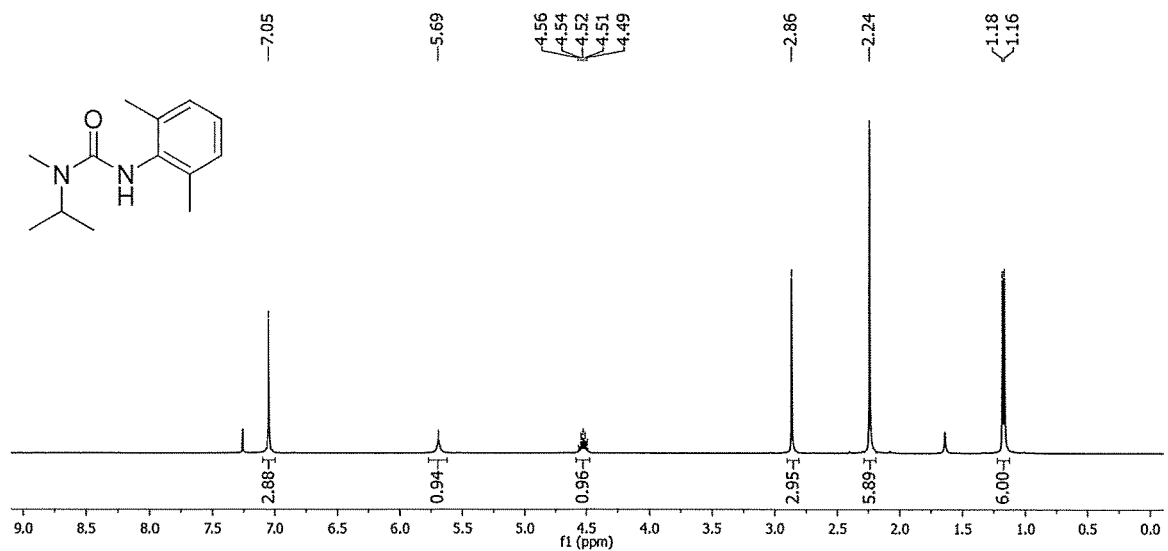
FIG. 35 is a $^1$H NMR spectrum (400 MHz, CDCl$_3$, 298 K) of 3-(2,6-dimethylphenyl)-1-isopropyl-1-phenylurea.
Figure 36:
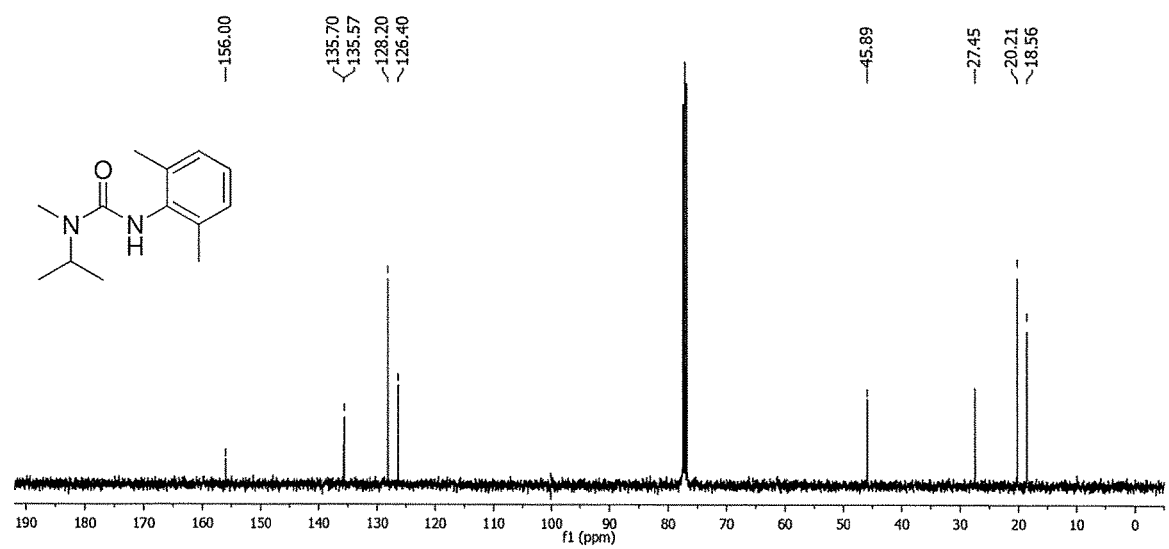
FIG. 36 is a $^{13}$C NMR spectrum (100 MHz, benzene-d$_6$, 298 K) of 3-(2,6-dimethylphenyl)-1-isopropyl-1-phenylurea.

FIG. 35 is a $^1$H NMR spectrum (400 MHz, CDCl$_3$, 298 K) of 3-(2,6-dimethylphenyl)-1-isopropyl-1-phenylurea. FIG. 36 is a $^{13}$C NMR spectrum (100 MHz, benzene-d$_6$, 298 K) of 3-(2,6-dimethylphenyl)-1-isopropyl-1-phenylurea.

Synthesis of
1-benzhydryl-3-(2,6-dimethylphenyl)-1-methylurea

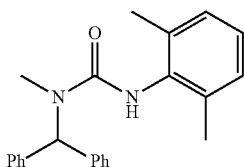

Prepared following the general procedure outlined above: 2,6-dimethylaniline (307 mg, 2.53 mmol), triphosgene (250.2 mg, 0.843 mmol), DIPEA (981 mg, 7.59 mmol), N-methyl-1,1-diphenylmethanimine (500 mg, 2.53 mmol). Recrystallization from a concentrated ethyl acetate solution provided the desired compound as a white solid (750 mg, 86%): $^1$H NMR (CDCl$_3$, 400 MHz, 298 K): δ 7.41-7.27 (overlapping m, 10H, o,m,p-C$_6$H$_5$), 7.04 (s, 3H, m,p-C$_6$H$_5$), 6.70 (s, 1H, NHCH), 5.78 (br s, 1H, NH), 2.88 (s, 3H, CH$_3$), 2.16 (s, 6H, 2,6-(CH$_3$)$_2$C$_6$H$_3$) ppm. $^{13}$C NMR (CDCl$_3$, 101 MHz, 298 K): δ 156.57 (C=O), 139.66, 135.47, 135.30, 128.80, 128.77, 128.25, 127.80, 126.49, 63.30, 32.05, 28.48 ppm. HRMS (ESI): m/z calcd for C$_{23}$H$_{25}$N$_2$O [M+H$^+$]: 345.1967 Found: 345.1964.

Figure 37:
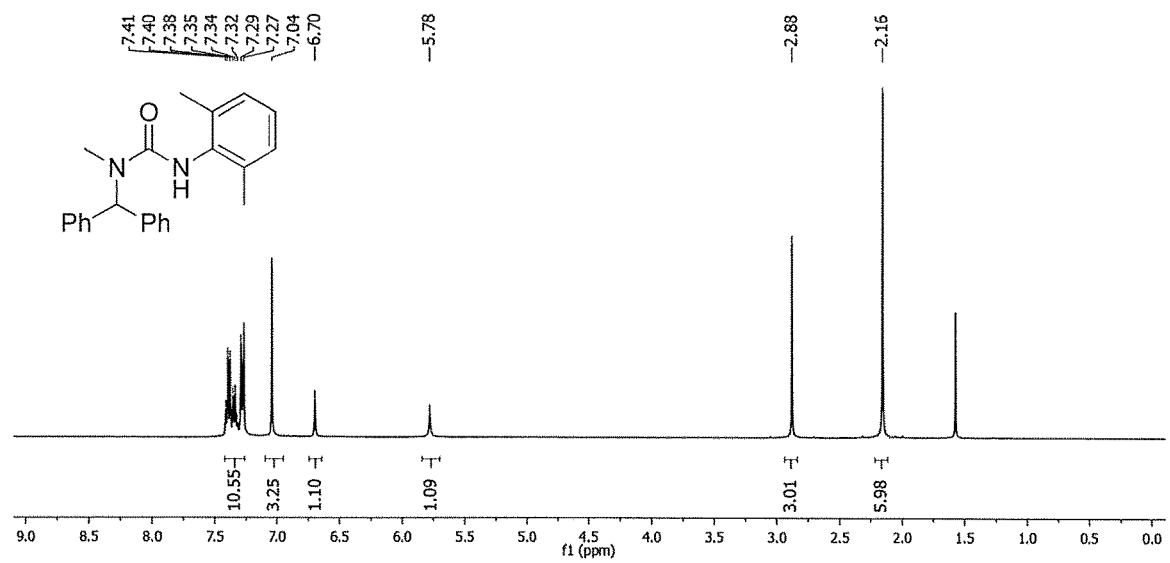
FIG. 37 is a $^1$H NMR spectrum (400 MHz, CDCl$_3$, 298 K) of 1-benzhydryl-3-(2,6-dimethylphenyl)-1-methylurea.
Figure 38:
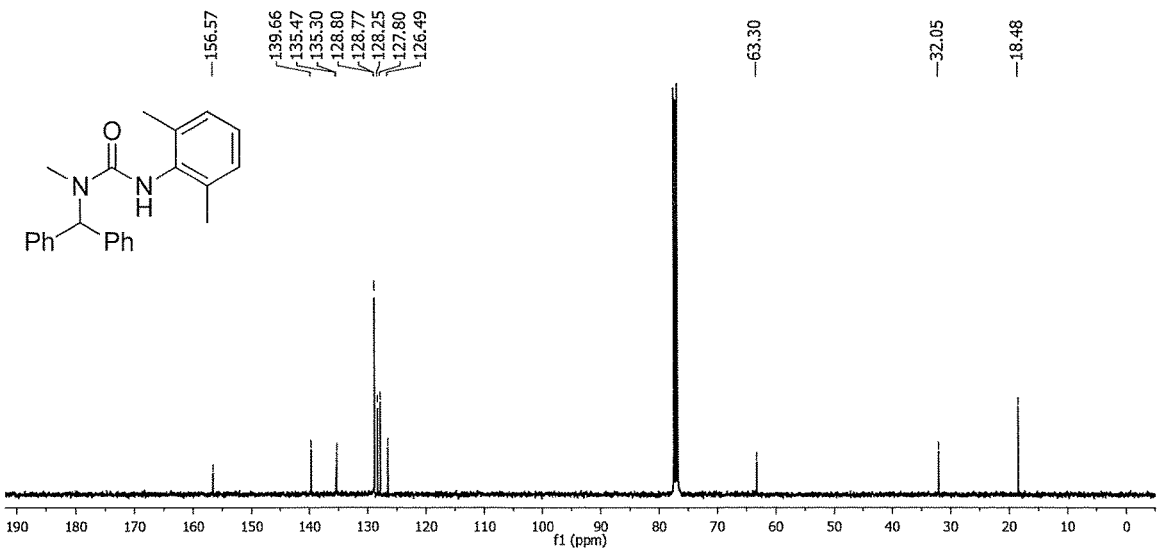
FIG. 38 is a $^{13}$C NMR spectrum (100 MHz, CDCl$_3$, 298 K) of 1-benzhydryl-3-(2,6-dimethylphenyl)-1-methylurea.

FIG. 37 is a $^1$H NMR spectrum (400 MHz, CDCl$_3$, 298 K) of 1-benzhydryl-3-(2,6-dimethylphenyl)-1-methylurea. FIG. 38 is a $^{13}$C NMR spectrum (100 MHz, CDCl$_3$, 298 K) of 1-benzhydryl-3-(2,6-dimethylphenyl)-1-methylurea.

Synthesis of 3-(2,6-diisopropylphenyl)-1-methyl-1-(1-phenylethyl)urea

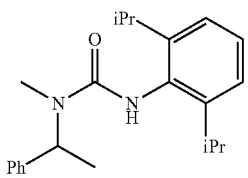 [SMILES: CC(C)c1cccc(C(C)C)c1NC(=O)N(C)C(C)c1ccccc1]

Prepared following the general procedure outlined above: 2,6-dimethylaniline (1.32 g, 7.40 mmol), triphosgene (724 mg, 2.44 mmol), DIPEA (2.87 g, 22.2 mmol), N-methyl-1,1-diphenylmethanimine (1.0 g, 7.40 mmol). Recrystallization from a concentrated ethyl acetate solution provided the desired compound as a white solid (1.81 g, 72.3(%): $^1$H NMR (CDCl$_3$, 400 MHz, 298 K): δ 7.51-7.50 (overlapping m, 4H), 7.45-7.39 (overlapping m, 2H), 7.37-7.35 (m, 1H), 7.28 (m, 1H), 5.78-5.72 (overlapping m, 2H), 3.22-3.12 (m, 2H, CH(CH$_3$)$_2$), 3.00 (s, 3H, CH$_3$), 1.72 (s, 3H, CH$_3$), 1.31 (s, 12H, CH(CH$_3$)$_2$) ppm. $^{13}$C NMR (CDCl$_3$, 101 MHz, 298 K): δ 157.22 (C=O), 146.52, 142.12, 132.80, 128.73, 127.63, 127.41, 126.95, 123.36, 52.99, 29.82, 28.79, 23.81 ppm. HRMS (ESI): m/z calcd for C$_{22}$H$_{31}$N$_2$O [M+H$^+$]: 339.2437. Found: 339.2444.

Figure 39:
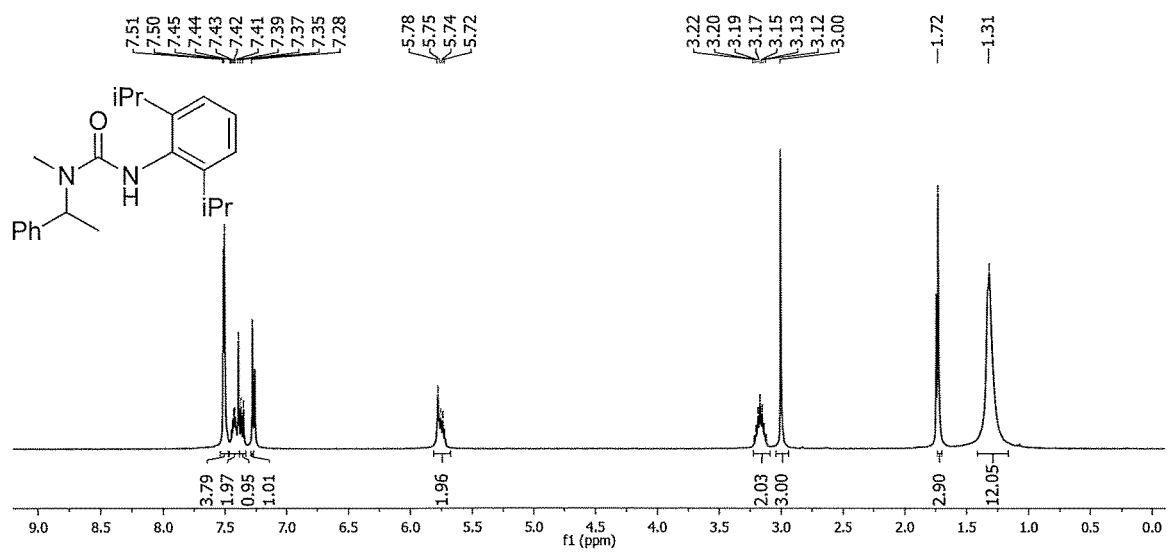
FIG. 39 is a $^1$H NMR spectrum (400 MHz, CDCl$_3$, 298 K) of 3-(2,6-diisopropylphenyl)-1-methyl-1-(1-phenylethyl) urea.
Figure 40:
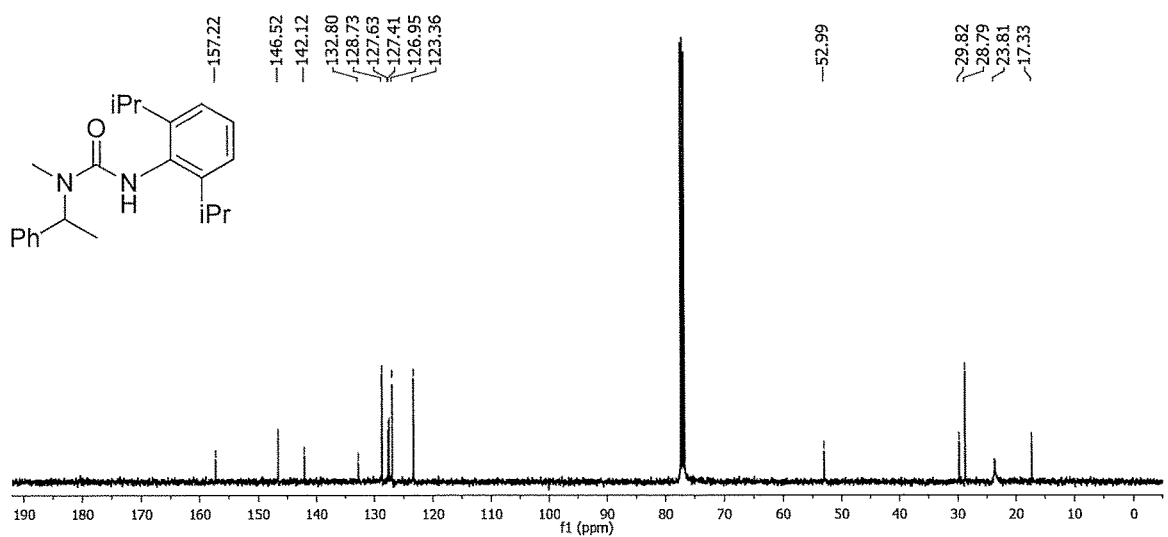
FIG. 40 is a $^{13}$C NMR spectrum (100 MHz, CDCl$_3$, 298 K) of 3-(2,6-diisopropylphenyl)-1-methyl-1-(1-phenylethyl) urea.

FIG. 39 is a $^1$H NMR spectrum (400 MHz, CDCl$_3$, 298 K) of 3-(2,6-diisopropylphenyl)-1-methyl-1-(1-phenylethyl)urea. FIG. 40 is a $^{13}$C NMR spectrum (100 MHz, CDCl$_3$, 298 K) of 3-(2,6-diisopropylphenyl)-1-methyl-1-(1-phenylethyl)urea.

Synthesis of Ta(CH$_2$SiMe$_3$)$_3$Br$_2$: A solution of Zn(CH$_2$SiMe$_3$)$_2$ (0.64 g, 2.67 mmol) in hexanes (20 mL) was added to a suspension of TaBr$_5$ (1.00 g, 1.72 mmol) in hexanes (10 mL). The reaction mixture was stirred at room temperature overnight forming a colorless precipitate. The following day, the solution was filtered and concentrated in vacuo to afford the formation of the title product as yellow powder. Yield (0.73 g, 71%). $^1$H NMR (toluene-d$_3$, 300 MHz, 298 K): δ 2.11 (s, 6H, CH$_2$), 0.29 (s, 27H, SiCH$_3$) ppm.

3.3 Ligand Salts

General procedure for the synthesis of ligand salts NaN(SiMe$_3$)$_2$ (1 equiv.) was added in portions to a suspension of the corresponding proteo-ligand (1 equiv.) in Et$_2$O (~10 mL) and stirred overnight at room temperature. The volatiles were then removed at low pressure and the resulting solid was thoroughly washed with hexanes (3×5 mL) and dried to give the sodium salt as a colorless powder. Salts were used directly without further characterization.

Scheme 2.
General method for the information of alkyl tantalum complexes

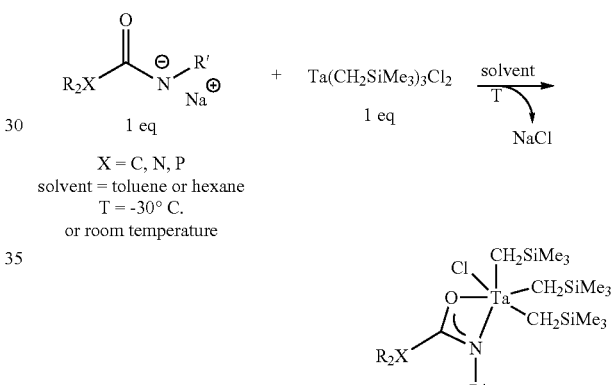

Synthesis and Characterization of Tantalum Based Ureate Complexes

Scheme 3.
Synthesis of tantalum complexes supported by cyclic ureate ligands

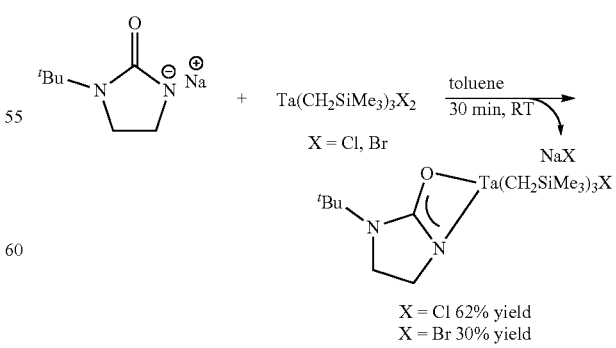

Figure 28:
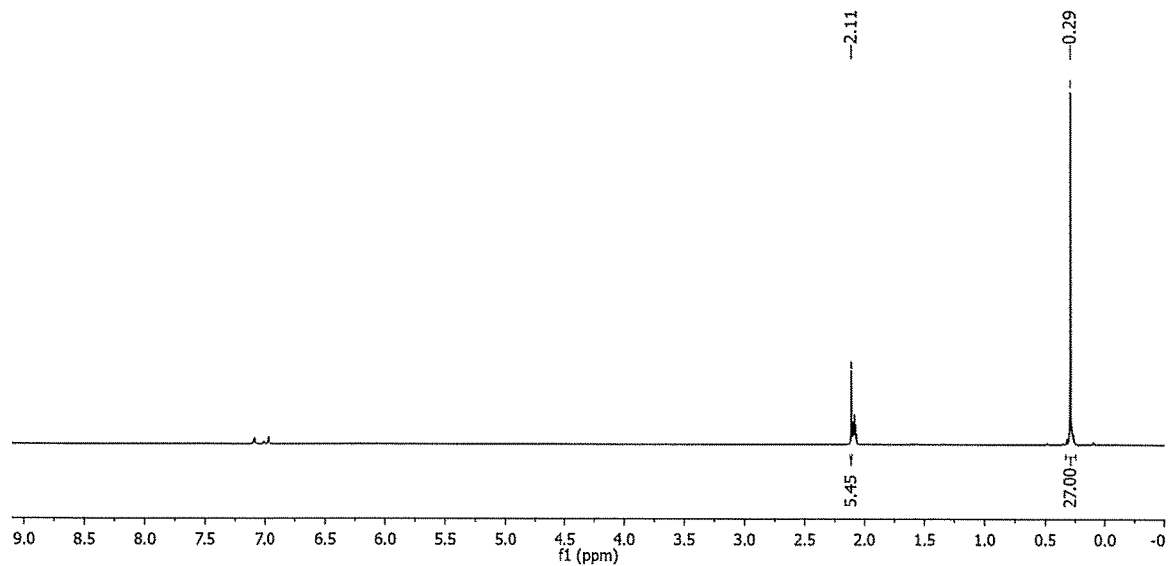
FIG. 28 is a $^1$H NMR spectrum (300 MHz, toluene-d$_8$, 298 K) of Ta(CH$_2$SiMe$_3$)$_3$Br$_2$.

FIG. 28 is a $^1$H NMR spectrum (300 MHz, toluene-d$_8$, 298 K) of Ta(CH$_2$SiMe$_3$)$_3$Br$_2$.

Synthesis of $^{tBu}$LTa(CH$_2$SiMe$_3$)$_3$Cl

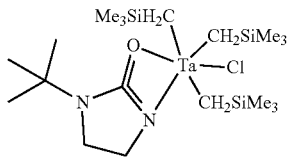

A suspension of $^{tBu}$L$^-$Na$^+$ (71 mg, 0.43 mmol) in toluene (3 mL) was added dropwise at room temperature to a solution of Ta(CH$_2$SiMe$_3$)Cl$_2$ (200 mg, 0.39 mmol) in toluene (3 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. A large crop of crystals were formed overnight which were further dried affording the title compound as pale yellow crystals. Yield (150 mg, 62%). $^1$H NMR (benzene-d$_6$, 300 MHz, 298 K): δ 3.36-3.23 (m, 2H, NCH$_2$), 2.75-2.62 (m, 2H, NCH$_2$), 1.57 (s, 6H, CH$_2$SiMe$_3$), 1.06 (s, 9H, NC(CH$_3$)$_3$), 0.36 (s, 27H, SiCH$_3$) ppm. $^{13}$C NMR (benzene-d$_6$, 75 MHz, 298 K): δ 171.36 (C=O), 90.19 (CH$_2$SiMe$_3$), 53.68 (NC(CH$_3$)$_3$), 45.38 (NCH$_2$), 44.41 (NCH$_2$), 27.96 (NC(CH$_3$)$_3$), 2.79 (SiCH$_3$) ppm. LRMS (ESI): m/z: 531 (M−CH$_2$SiMe$_3$−H$^+$), 443 (M−2CH$_2$SiMe$_3$−2H$^+$). Anal. Calcd. for C$_{19}$H$_{47}$ClN$_2$OSi$_3$Ta: C, 36.79; H, 7.64; N, 4.52; Found: C, 36.44; H, 7.69; N, 4.59.

Figure 29:
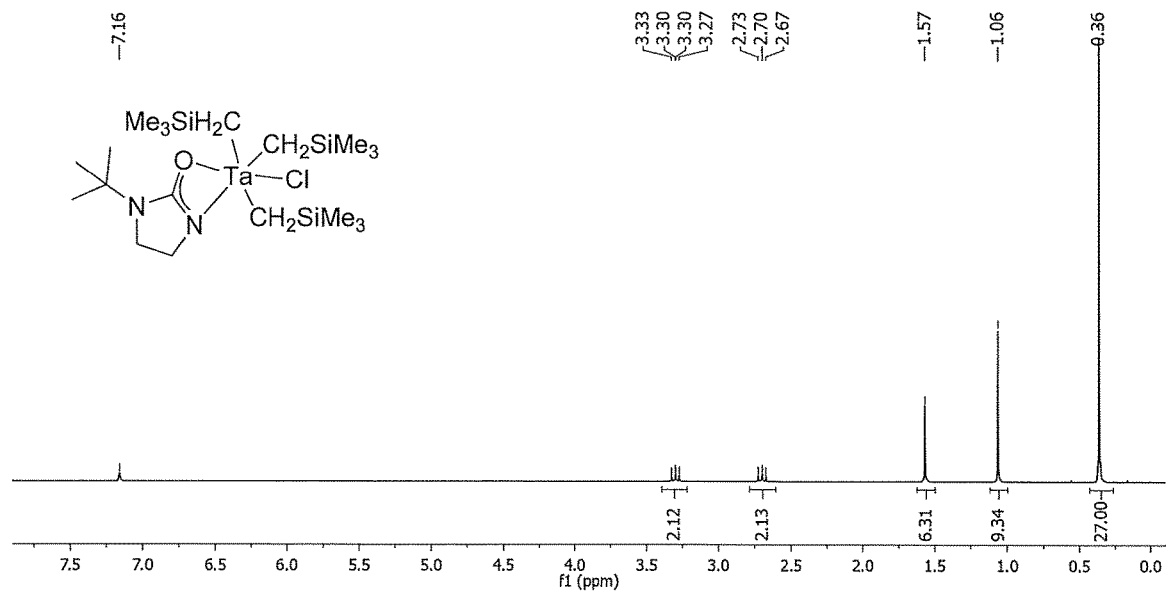
FIG. 29 is a $^1$H NMR spectrum (300 MHz, benzene-d$_6$, 298 K) of $^{tBu}$LTa(CH$_2$SiMe$_3$)$_3$Cl.
Figure 30:
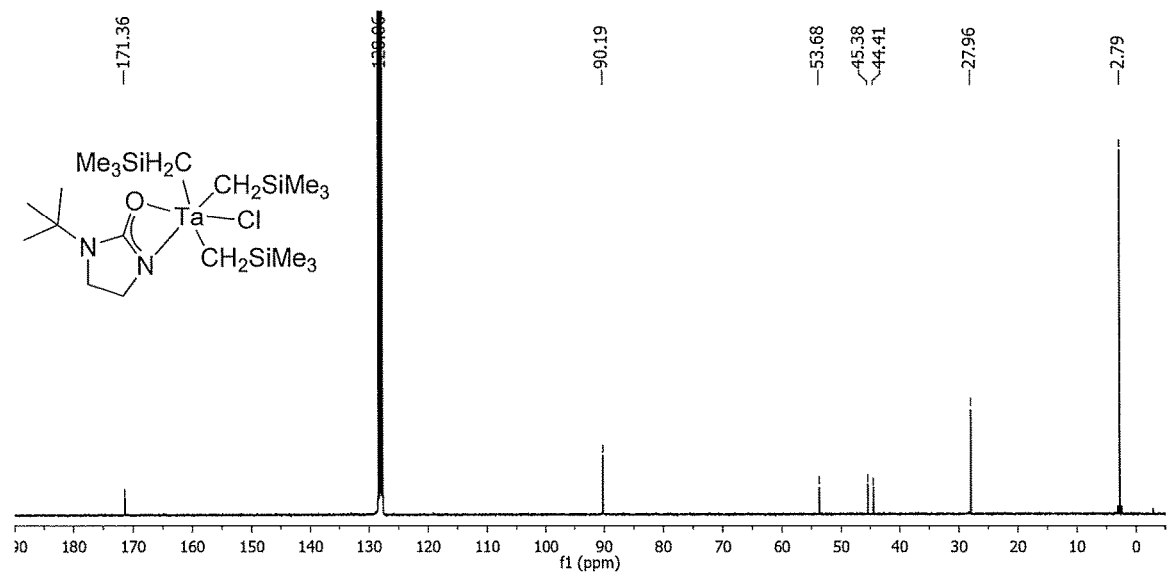
FIG. 30 is a $^{13}$C NMR spectrum (75 MHz, benzene-d$_6$, 298 K) of $^{tBu}$LTa(CH$_2$SiMe$_3$)$_3$Cl.

FIG. 29 is a $^1$H NMR spectrum (300 MHz, benzene-d$_6$, 298 K) of $^{tBu}$LTa(CH$_2$SiMe$_3$)$_3$Cl. FIG. 30 is a $^{13}$C NMR spectrum (75 MHz, benzene-de, 298 K) of $^{tBu}$LTa(CH$_2$SiMe$_3$)$_3$Cl.

Synthesis of $^{tBu}$LTa(CH$_2$SiMe$_3$)$_3$Br

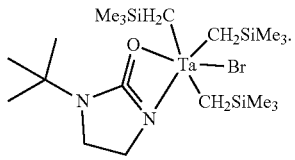

A suspension of $^{tBu}$L$^-$Na$^+$ (30 mg, 0.19 mmol) in toluene (3 mL) was added dropwise at room temperature to a solution of Ta(CH$_2$SiMe$_3$)Cl$_2$ (106 mg, 0.18 mmol) in toluene (3 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. A large crop of crystals were formed overnight which were further dried affording the title compound as pale yellow crystals. Yield (35 mg, 30%). $^1$H NMR (benzene-d$_6$, 400 MHz, 298 K): δ 3.31-3.24 (m, 2H, NCH$_2$), 2.72-2.65 (m, 2H, NCH$_2$), 1.62 (s, 6H, CH$_2$SiMe$_3$), 1.05 (s, 9H, NC(CH$_3$)$_3$), 0.37 (s, 27H, SiCH$_3$) ppm. $^{13}$C NMR (benzene-d$_6$, 75 MHz, 298 K): δ 171.18 (C=O), 94.33 (CH$_2$SiMe$_3$), 53.78 (NC(CH$_3$)$_3$), 45.34 (NCH$_2$), 44.16 (NCH$_2$), 27.96 (NC(CH$_3$)$_3$), 2.91 (SiCH$_3$) ppm.

Figure 31:
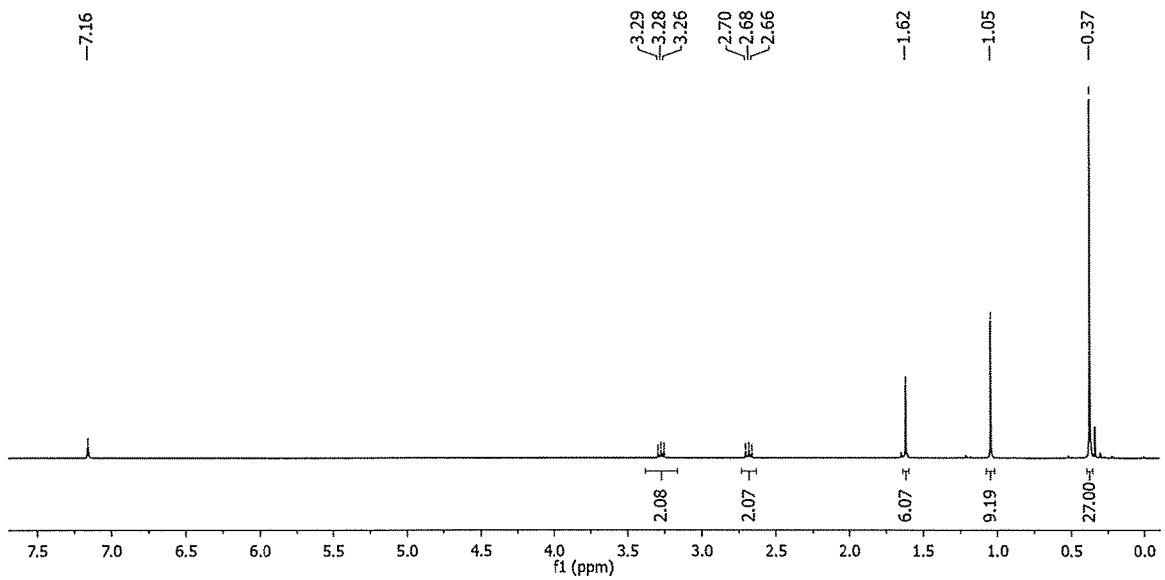
FIG. 31 is a $^1$H NMR spectrum (400 MHz, benzene-d$_6$, 298 K) of $^{tBu}$LTa(CH$_2$SiMe$_3$)$_3$Br.
Figure 32:
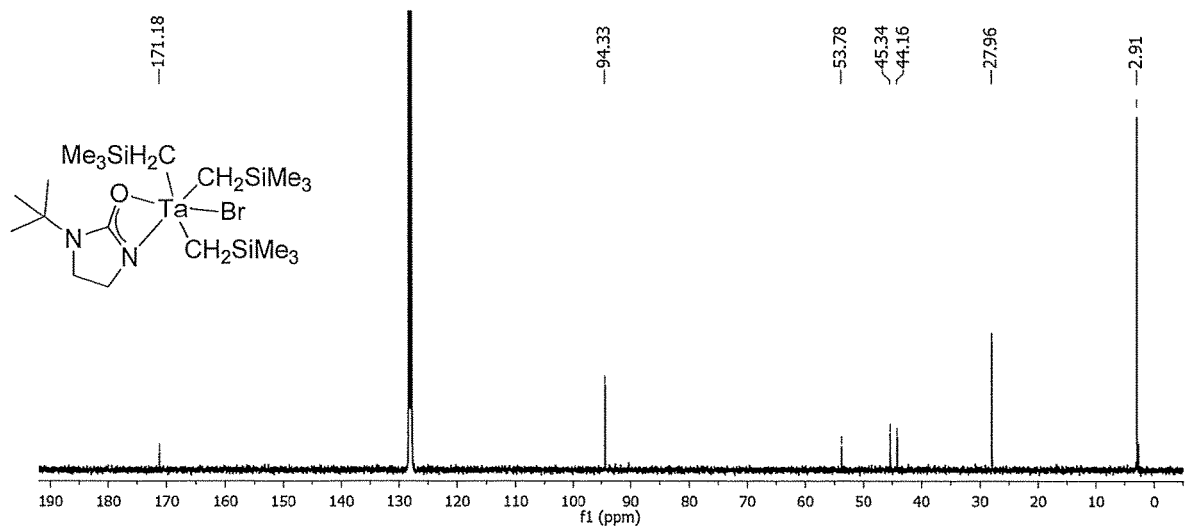
FIG. 32 is a $^{13}$C NMR spectrum (100 MHz, benzene-d$_6$, 298 K) of $^{tBu}$LTa(CH$_2$SiMe$_3$)$_3$Br.

FIG. 31 is a $^1$H NMR spectrum (400 MHz, benzene-d$_6$, 298 K) of $^{tBu}$LTa(CH$_2$SiMe$_3$)$_3$Br. FIG. 32 is a $^{13}$C NMR spectrum (100 MHz, benzene-d$_6$, 298 K) of $^{tBu}$LTa(CH$_2$SiMe$_3$)$_3$Br.

Synthesis and Characterization of Tantalum Based Ureate Complexes

Synthesis of LTa(CH$_2$SiMe$_3$)$_3$Cl

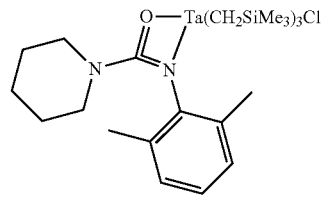

A suspension of L$^-$Na$^+$ (206 mg, 0.81 mmol) in toluene (5 mL) was added dropwise at room temperature to a solution of Ta(CH$_2$SiMe$_3$)Cl$_2$ (378 mg, 0.736 mmol) in toluene (6 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. Over a week period, a large amount of solid precipitated. The mixture was then filtered and the resulting solid was dried in vacuo to form the desired complex. Yield (370 mg, 71%). $^1$H NMR (benzene-d$_6$, 300 MHz, 298 K): δ 6.92-6.80 (m, 3H, C$_6$H$_3$), 3.52-3.85 (m, 2H, CH$_2$), 2.21 (s, 6H, CH$_2$SiMe$_3$), 1.41 (s, 6H, CH$_3$), 0.39 (s, 27H, SiCH$_3$) ppm.

Figure 41:
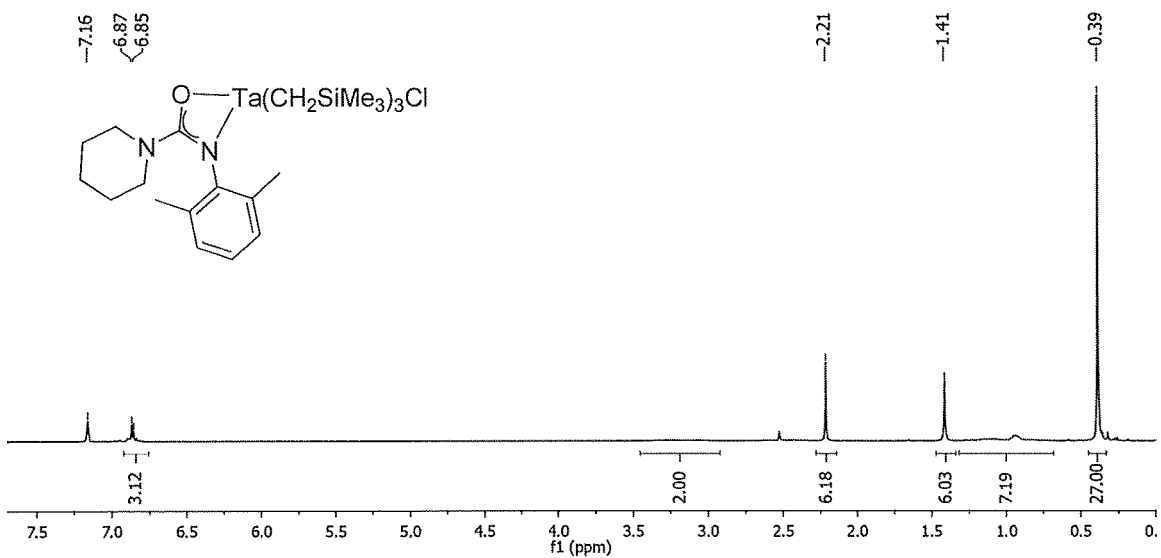
FIG. 41 is a $^1$H NMR spectrum (300 MHz, benzene-cis, 298 K) of LTa(CH$_2$SiMe$_3$)$_3$Cl.

FIG. 41 is a $^1$H NMR spectrum (300 MHz, benzene-d$_6$, 298 K) of LTa(CH$_2$SiMe$_3$)$_3$Cl.

3.4 Hydroaminoalkylation Reaction

General procedure for hydroaminoalkylation reaction: Solid tantalum precursor (0.0025 mmol) was weighed into a vial, followed by addition of the chosen ligand salt (0.025 mmol) d$_8$-toluene (0.3 g) was added, and the resultant mixture was left for 15 minutes. A chosen amine substrate was then added (0.5 mmol), followed by the alkene (0.5 mmol). The resultant reaction mixture was transferred into a J. Young NMR tube and the vial was rinsed with an additional 0.2 g of d$_8$-toluene. An initial $^1$H NMR spectrum was recorded and the sample was added to a pre-heated oil bath. All conversion values were determined by $^1$H NMR spectroscopy. After removal of all reaction solvent, pentane was added to the reaction mixture and a white precipitate was formed instantaneously. Residual tantalum salts and proteo-ligands were then removed by filtering the pentane solution at −80° C. Unreacted amine or alkene starting materials were removed at 40° C. under low pressure. In all cases, $^1$H NMR spectroscopy still showed the presence of proteo-ligands in low amounts (2-4%), which can be entirely removed by column chromatography. N-(2-propylhexyl)aniline and N-(2-ethylpentyl)aniline showed signs of decomposition while heated under vacuum, and therefore must be purified by column chromatography.

General procedure for post-polymerization amination of polyolefins. All experiments were performed in the presence of Ta complex $^{tBu}$LTa(CH$_2$SiMe$_3$)$_3$Cl (Table 12), which could be used either in an isolated form or formed in situ.

Based on NMR experiments, the initial polyolefins had a molecular weight range between 350-3500 g/mol. The precatalyst and the internal standard (1,3,5-trimethoxybenzene) were weighed in separate vials. In a different vial, the polyolefin (in a stock solution or neat) was mixed with the corresponding amount of the amine. Toluene-d8 was then added to the first vials and the combined solution of all mentioned vials was transferred to a J-young NMR tube. The vials were further rinsed with 200 mg of toluene-d8 and transferred to the NMR tube. An initial 1H-NMR spectrum was recorded prior to heating the sample. The NMR tube was then added to a preheated oil bath (110° C. — for N-methylaniline and N-methylcyclohexylamine; 145° C. —for N-methylbutylamine) for the corresponding amount of time. The polymers derived from Sample 1, vinyl-terminated atactic polypropylene ("vt aPP") having a molecular weight of about 300 g/mol and supplied neat and corresponding to entries 1 to 6 in Table 12, were purified via column chromatography. The polymers derived from Sample 2, vinyl-terminated atactic polypropylene ("vt aPP"; supplied as a stock solution in toluene and corresponding to entries 7 to 12 in Table 12) having a molecular weight of about 1,500 to about 2,000 g/mol, and Sample 3, vinyl-terminated copolymer poly(ethylene-co-propylene) (vt EP) having a molecular weight of approximately 3500 g/mol and corresponding to entries 12 to 14 in Table 12, were purified by dissolving the sample in dichloromethane and precipitating the desired product with methanol. This process was repeated 3 times. All reactions were performed on a 100 mg scale corresponding to the polyolefin.

N-(2-methyloctyl)aniline

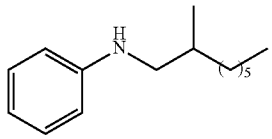

N-methylaniline (54 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 88%. $^1$H NMR (CDCl$_3$, 300 MHz, 298 K): δ 7.24-7.16 (m, 2H, burn-C$_6$H$_5$), 6.75-6.67 (m, 1H, p-C$_6$H$_5$), 6.67-6.60 (m, 2H, o-C$_6$H$_5$), 3.69 (br s, 1H, NH), 3.08 (dd, J$_{H-H}$=12.8, 5.8 Hz, 1H, NC(H)H), 2.91 (dd, J$_{H-H}$=12.2, 7.3 Hz, 1H, NC(H)H), 1.86-1.68 (m, 1H, CH), 1.53-1.14 (overlapping m, 10H, CH$_2$), 1.00 (d, J$_{H-H}$=6.6 Hz, 3H, CHCH$_3$), 0.97-0.89 (t, J$_{H-H}$=6.1 Hz, 3H, CH$_2$CH$_3$) ppm. The chemical shifts for the title compound match those reported by Hartwig et al.

N-(cyclooctylmethyl)aniline

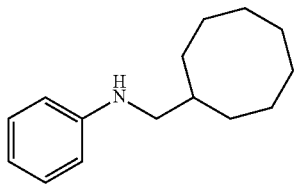 [SMILES: c1ccc(NCC2CCCCCCC2)cc1]

N-methylaniline (54 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 83%. $^1$H NMR (CDCl$_3$, 300 MHz, 298 K): δ 7.20 (dd, J$_{H-H}$=8.5, 7.4 Hz, 2H, m-C$_6$H$_5$), 6.70 (t, J$_{H-H}$=6.7 Hz, 1H, p-C$_6$H$_5$), 6.62 (dd, J$_{H-H}$=8.5, 0.9 Hz, 2H, o-C$_6$H$_5$), 3.71 (br s, 1H, NH), 2.08 (d, J$_{H-H}$=6.8 Hz, NCH$_2$), 1.92-1.27 (overlapping m, 13H, CH$_2$ and CH) ppm.

4-methoxy-N-(2-methyloctyl)aniline

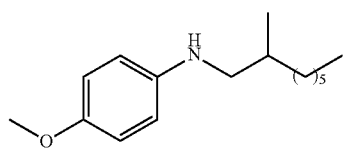

4-methoxy-N-methylaniline (96 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 77%. $^1$H NMR (CDCl$_3$, 300 MHz, 298 K): δ 6.84-6.74 (m, 2H, m-C$_6$H$_4$), 6.63-6.55 (m, 2H, o-C$_6$H$_4$), 3.76 (s, 3H, OCH$_3$), 3.38 (br s, 1H, NH), 3.02 (dd, J$_{H-H}$=5.8, 12.1 Hz, 1H, NC(H)H), 3.02 (dd, J$_{H-H}$=7.8, 12.1 Hz, 1H, NC(H)H), 1.82-1.64 (m, 1H, CH$_2$), 1.55-1.05 (m, 10H, CH$_2$), 0.98 (d, J$_{H-H}$=6.6 Hz, 3H, CHCH$_3$), 0.91 (t, J$_{H-H}$=6.7 Hz, 3H, CH$_2$CH$_3$) ppm. The chemical shifts for the title compound match those previously reported in the literature.

4-bromo-N-(2-methyloctyl)aniline

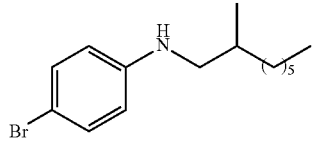

4-bromo-N-methylaniline (93 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 86%. $^1$H NMR (CDCl$_3$, 300 MHz, 298 K): δ 7.23 (d, =8.7 Hz, 2H, m-C$_6$H$_4$), 6.48 (d, J$_{H-H}$=8.9 Hz, 2H, o-C$_6$H$_4$), 3.92 (br s, 1H, NH), 3.01 (dd, J$_{H-H}$=5.9, 12.2 Hz, 1H, NC(H)H), 2.84 (dd, J$_{H-H}$=7.1, 12.1 Hz, 1H, NC(H)H), 1.78-1.65 (m, 1H, CH), 1.51-1.08 (m, 10H, CH$_2$), 0.96 (d, J$_{H-H}$=6.6 Hz, 3H, CHCH$_3$), 0.89 (t, J$_{H-H}$=6.9 Hz, 3H, CH$_2$CH$_3$) ppm. $^{13}$C NMR (CDCl$_3$, 75 MHz, 298 K): δ 148.51 (i-C$_6$H$_4$), 129.34 (m-C$_6$H$_4$), 117.24 (p-C$_6$H$_4$), 112.87 (o-C$_{81}$-14), 48.11, 47.99, 37.45, 37.28, 36.79, 36.56, 29.68, 27.37, 27.00, 26.11, 25.95, 25.04, 14.94 (CH$_3$), 14.48 (CH$_3$) ppm.

Figure 5:
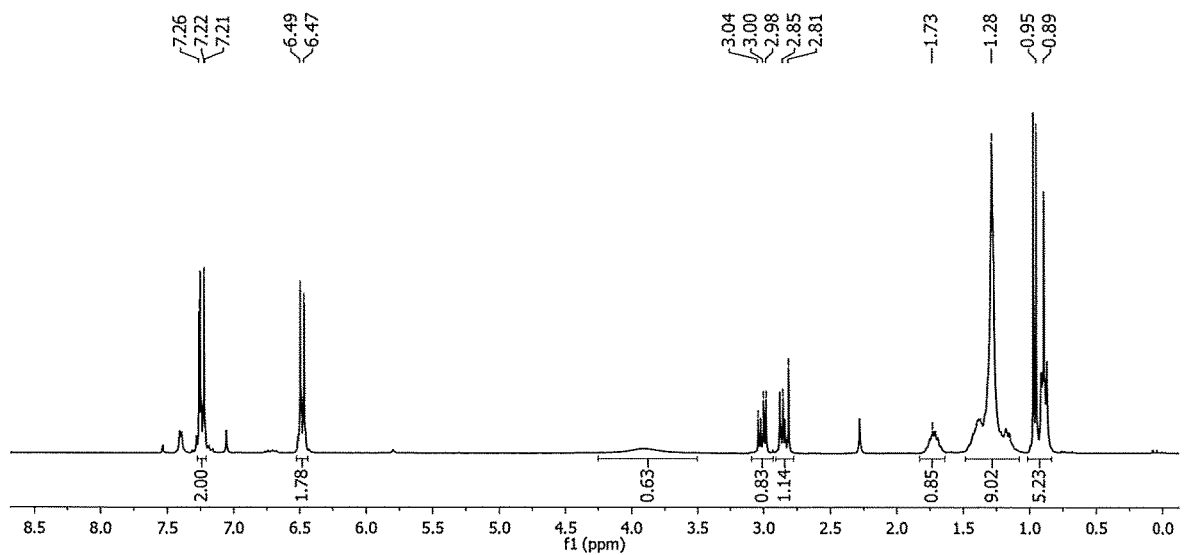
FIG. 5 is a $^1$H NMR spectrum (300 MHz, CDCl$_3$, 298 K) of 4-bromo-N-(2-methyloctyl)aniline.
Figure 6:
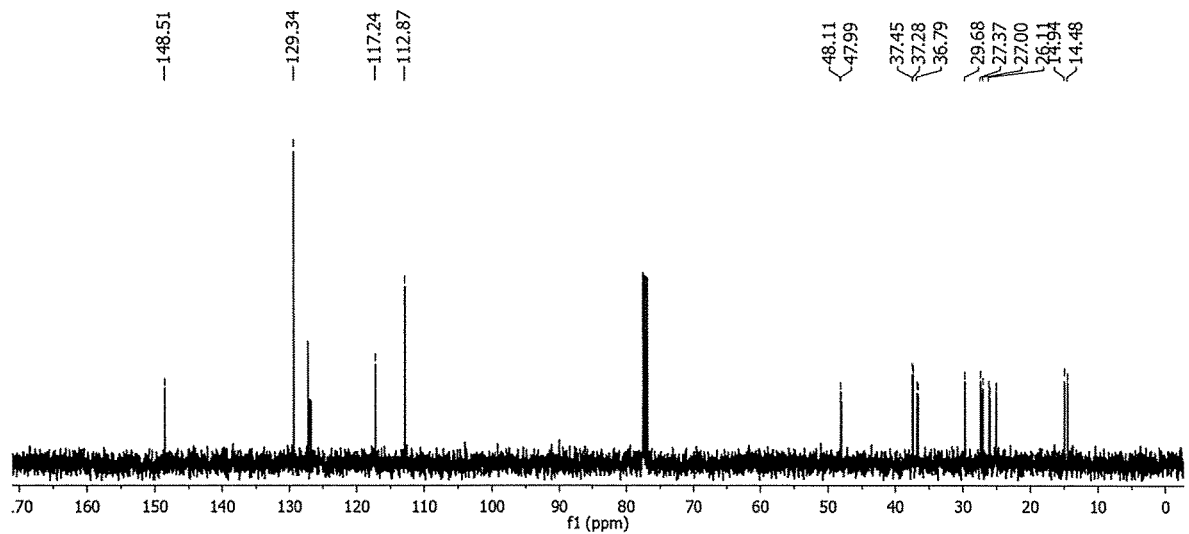
FIG. 6 is a $^{13}$C NMR spectrum (100 MHz, CDCl$_3$, 298 K) of 4-bromo-N-(2-methyloctyl)aniline.

FIG. 5 is a $^1$H NMR spectrum (300 MHz, CDCl$_3$, 298 K) of 4-bromo-N-(2-methyloctyl)aniline. FIG. 6 is a $^{13}$C NMR spectrum (100 MHz, CDCl$_3$, 298 K) of 4-bromo-N-(2-methyloctyl)aniline.

4-bromo-N-(cyclooctylmethyl)aniline

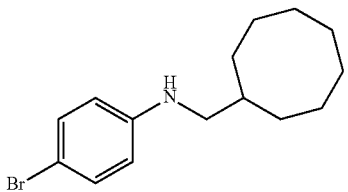

4-bromo-N-methylaniline (93 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 95%. $^1$H NMR (CDCl$_3$, 300 MHz, 298 K): δ 7.25 (d, J$_{H-H}$=8.8 Hz, m-C$_6$H$_4$), 6.47 (d, J$_{H-H}$=8.8 Hz, o-C$_6$H$_4$), 3.75 (br s, 1H, NH), 2.90 (d, J$_{H-H}$=6.8 Hz, NCH$_2$), 1.86-1.24 (overlapping m, 13H, CH and CH$_2$) ppm. $^{13}$C NMR (CDCl$_3$, 75 MHz, 298 K): δ 147.65 (i-C$_6$H$_4$), 131.95 (m-C$_6$H$_4$), 114.25 (o-C$_6$H$_4$), 108.40 (p-C$_6$H$_4$), 51.21 (NCH$_2$), 37.33 (CH$_2$), 30.67 (CH$_2$), 27.13 (CH$_2$), 26.41 (CH$_2$), 25.58 (CH$_2$) ppm.

Figure 7:
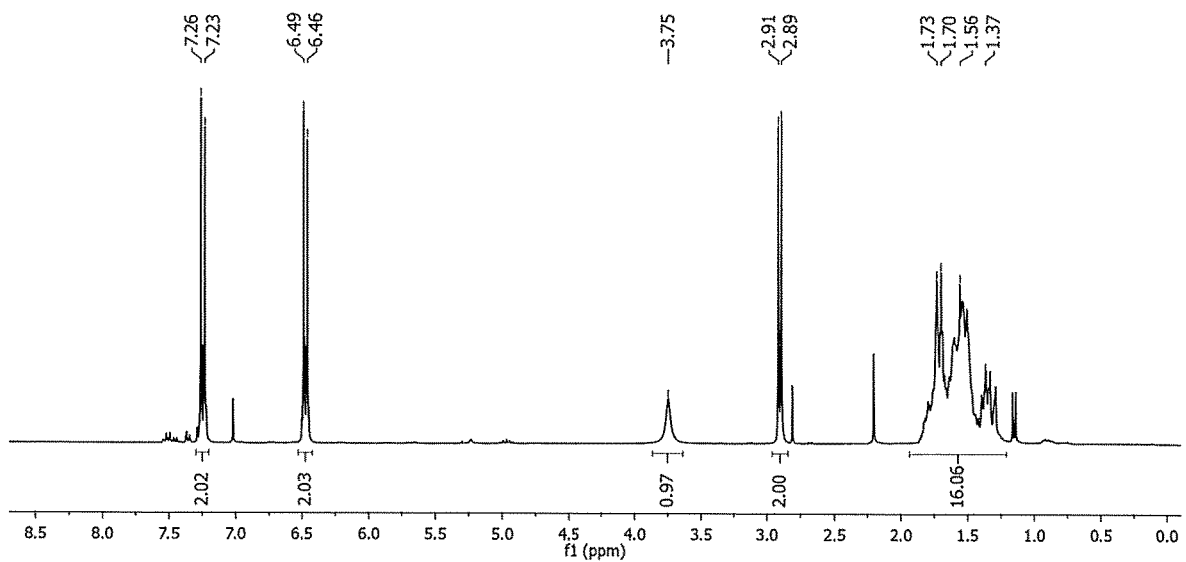
FIG. 7 is a $^1$H NMR spectrum (300 MHz, CDCl$_3$, 298 K) of 4-bromo-N-(cyclooctylmethyl)aniline.
Figure 8:
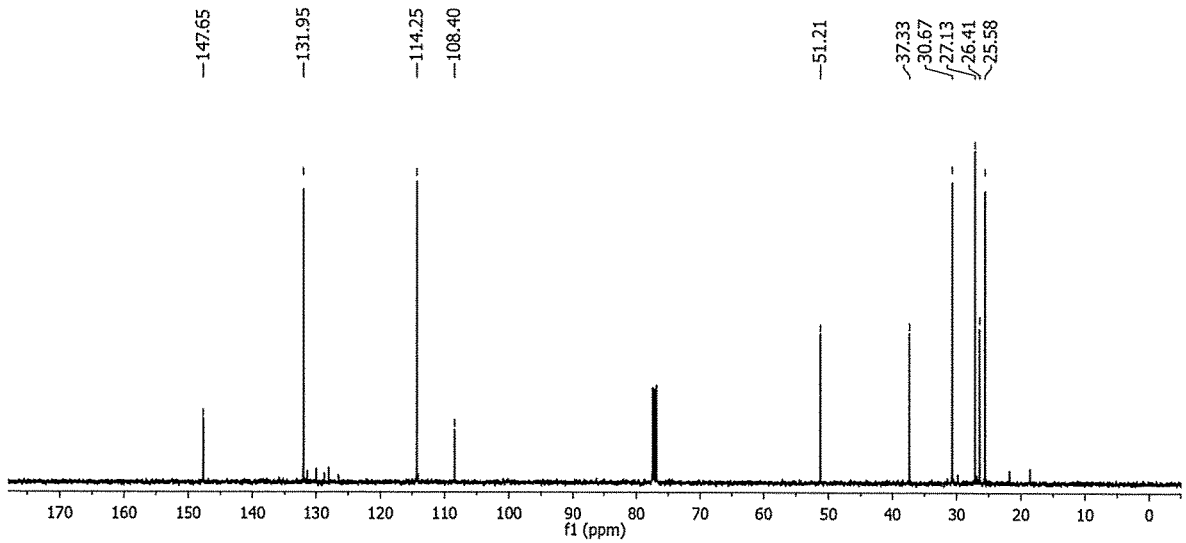
FIG. 8 is a $^{13}$C NMR spectrum (100 MHz, CDCl$_3$, 298 K) of 4-bromo-N-(cyclooctylmethyl)aniline.

FIG. 7 is a $^1$H NMR spectrum (300 MHz, CDCl$_3$, 298 K) of 4-bromo-N-(cyclooctylmethyl)aniline. FIG. 8 is a $^{13}$C NMR spectrum (100 MHz, CDCl$_3$, 298 K) of 4-bromo-N-(cyclooctylmethyl)aniline.

4-chloro-N-(2-methyloctyl)aniline

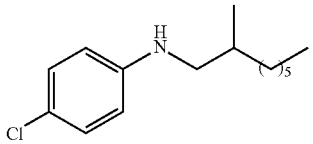

4-chloro-N-methylaniline (71 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 90%. $^1$H NMR (CDCl$_3$, 300 MHz, 298 K): δ 7.12 (d, J$_{H-H}$=8.8 Hz, 2H, m-C$_6$H$_5$), 6.52 (d, J$_{H-H}$=8.8 Hz, 2H, o-C$_6$H$_5$), 3.78 (br s, 1H, NH), 3.02 (dd, J$_{H-H}$=5.9, 12.2 Hz, 1H, NC(H)H), 2.86 (dd, J$_{H-H}$=7.2, 12.2 Hz, 1H, NC(H)H), 1.82-1.65 (m, 1H, CH), 1.51-1.09 (m, 10H, CH$_2$), 0.97 (d, J$_{H-H}$=6.6 Hz, 3H, CHCH$_3$), 0.91 (t, J$_{H-H}$=6.8 Hz, 3H, CH$_2$CH$_3$) ppm. The chemical shifts for the title compound match those previously reported in the literature.

4-chloro-N-(cyclooctylmethyl)aniline

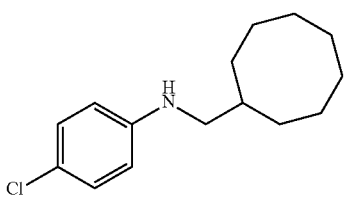 [SMILES: Clc1ccc(NCC2CCCCCCC2)cc1]

4-chloro-N-methylaniline (71 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 93%. $^1$H NMR (CDCl$_3$, 300 MHz, 298 K): δ 7.10 (d, J$_{H-H}$=8.8 Hz, m-C$_6$H$_4$), 6.51 (d, J$_{H-H}$=8.8 Hz, o-C$_6$H$_4$), 3.71 (br s, 1H, NH), 2.90 (d, J$_{H-H}$=6.8 Hz, NCH$_2$), 1.87-1.21 (overlapping m, 13H, CH and CH$_2$). ppm. $^{13}$C NMR (CDCl$_3$, 75 MHz, 298 K): δ 147.29 (i-C$_6$H$_4$), 129.10 (m-C$_6$H$_4$), 121.41 (p-C$_6$H$_4$), 113.73 (o-C$_6$H$_4$), 51.32 (NCH$_2$), 37.38 (CH$_2$), 30.70 (CH$_2$), 27.14 (CH$_2$), 26.43 (CH$_2$), 25.59 (CH$_2$) ppm.

Figure 9:
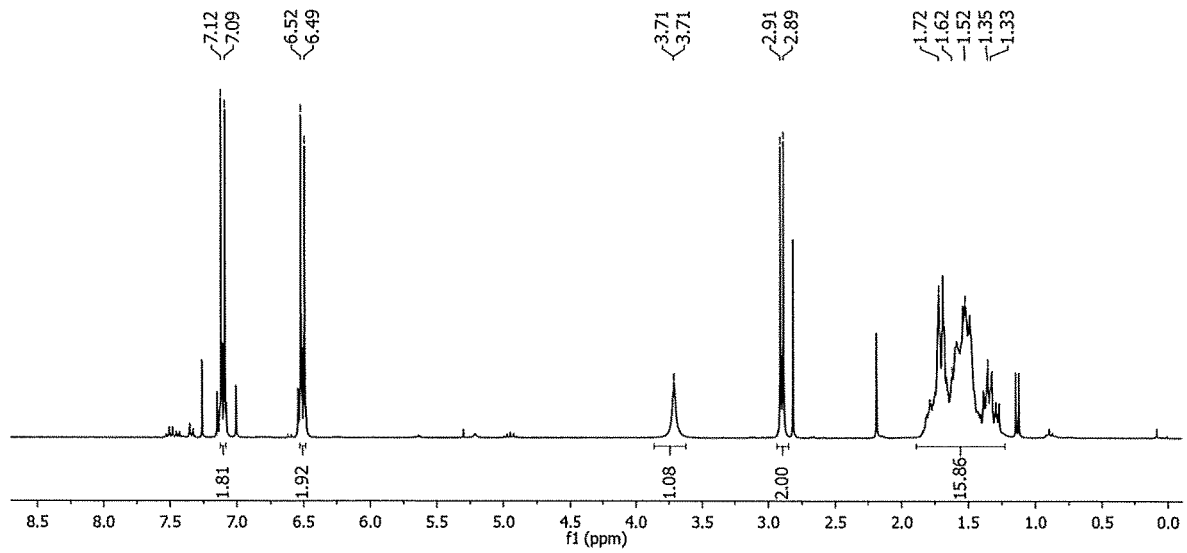
FIG. 9 is a $^1$H NMR spectrum (300 MHz, CDCl$_3$, 298 K) of 4-chloro-N-(cyclooctylmethyl)aniline.
Figure 10:
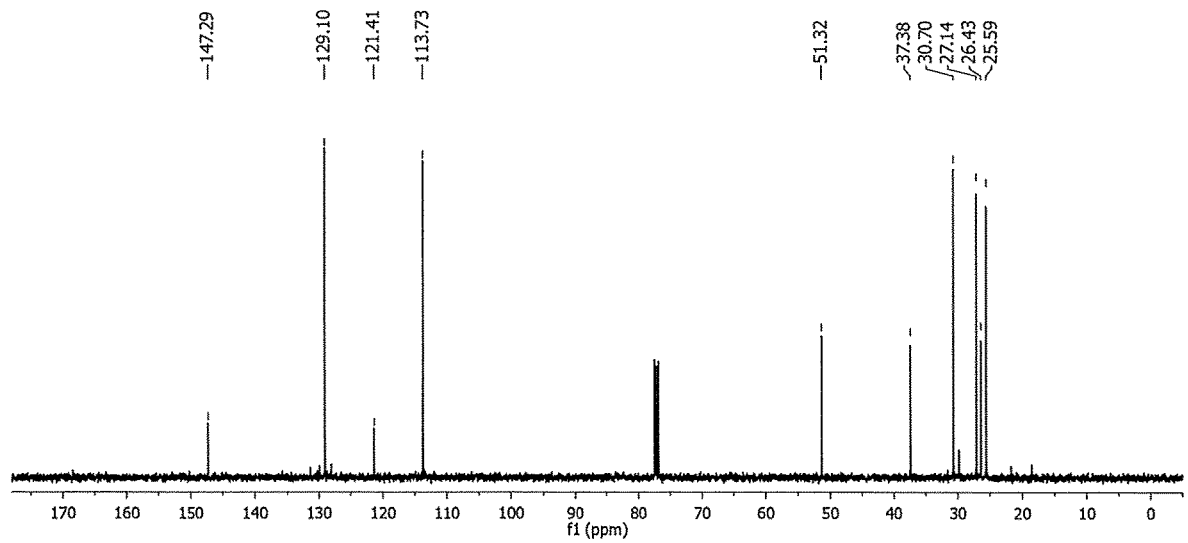
FIG. 10 is a $^{13}$C NMR spectrum (100 MHz, CDCl$_3$, 298 K) of 4-chloro-N-(cyclooctylmethyl)aniline.

FIG. 9 is a $^1$H NMR spectrum (300 MHz, CDCl$_3$, 298 K) of 4-chloro-N-(cyclooctylmethyl)aniline. FIG. 10 is a $^{13}$C NMR spectrum (100 MHz, CDCl$_3$, 298 K) of 4-chloro-N-(cyclooctylmethyl)aniline.

4-fluoro-N-(2-methyloctyl)aniline

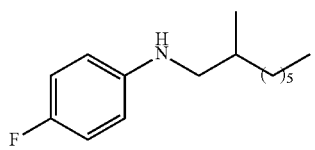

4-fluoro-N-methylaniline (63 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 88%. NMR (CDCl$_3$, 300 MHz, 298 K): δ 6.89 (t, J$_{H-H}$=8.8 Hz, 2H, m-C$_6$H$_5$), 6.59-6.50 (m, 2H, o-C$_6$H$_5$), 3.57 (br s, 1H, NH), 3.02 (dd, J$_{H-H}$=5.9, 12.1 Hz, 1H, NC(H)H), 2.85 (dd, J$_{H-H}$=7.2, 12.0 Hz, 1H, NC(H)H), 1.82-1.65 (m, 1H, CH), 1.51-1.11 (m, 10H, CH$_2$), 0.98 (d, J$_{H-H}$=6.7 Hz, 3H, CHCH$_3$), 0.91 (t, J$_{H-H}$=6.9 Hz, 3H, CH$_2$CH$_3$) ppm.

N-(cyclooctylmethyl)-4-fluoroaniline

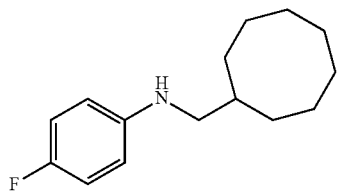 [SMILES: Fc1ccc(NCC2CCCCCCC2)cc1]

4-fluoro-N-methylaniline (63 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 88%. $^1$H NMR (CDCl$_3$, 300 MHz, 298 K): δ 6.89 (t, J$_{H-H}$=8.7 Hz, 2H, m-C$_6$H$_4$), 6.57-6.49 (m, 2H, o-C$_6$H$_4$), 3.58 (br s, 1H, NH), 2.90 (d, J$_{H-H}$=6.7 Hz, 2H, NCH$_2$), 1.88-1.22 (overlapping m, 13H, CH and CH$_2$) ppm. $^{13}$C NMR (CDCl$_3$, 100 MHz, 298 K): δ 155.68 (d, J$_{C-F}$=234.2 Hz, p-C$_6$H$_4$), 145.05 (i-C$_6$H$_4$), 115.66 (d, J$_{C-F}$=22.2 Hz, m-C$_6$H$_4$), 113.49 (d, J$_{C-F}$=7.3 Hz, o-C$_6$H$_4$), 51.99 (NCH$_2$), 37.41 (CH$_2$), 30.72 (CH$_2$), 27.15 (CH$_2$), 26.43 (CH$_2$), 25.60 (CH$_2$) ppm. $^{19}$F NMR (CDCl$_3$, 282.4 MHz, 298 K): δ−129.00 (tt, J$_{H-F}$=4.5 Hz, 1F, C$_6$H$_4$F) ppm.

Figure 11:
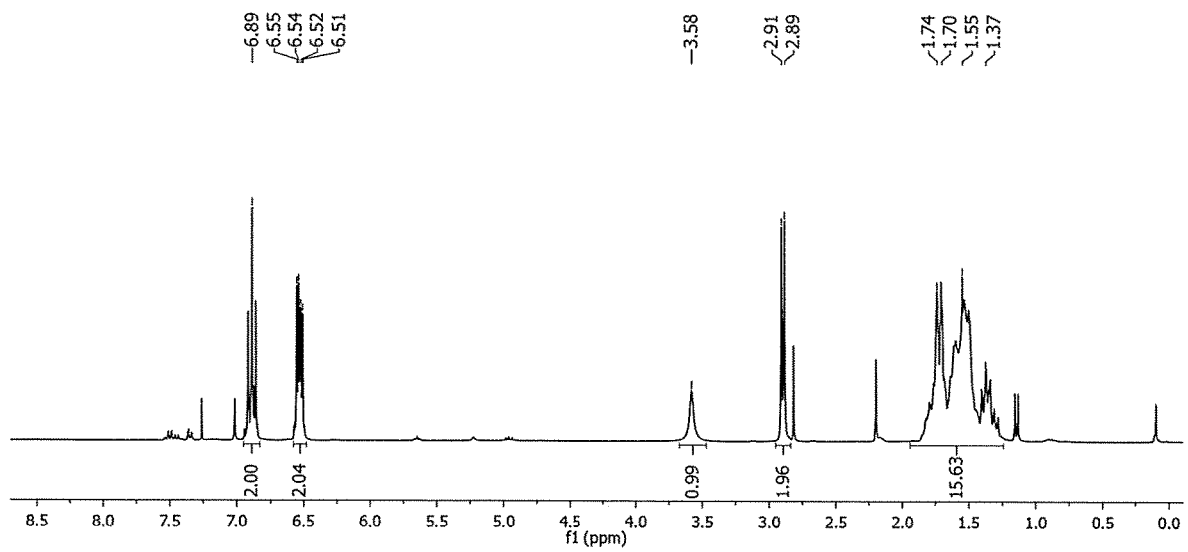
FIG. 11 is a $^1$H NMR spectrum (300 MHz, CDCl$_3$, 298 K) of N-(cyclooctylmethyl)-4-fluoroaniline.
Figure 12:
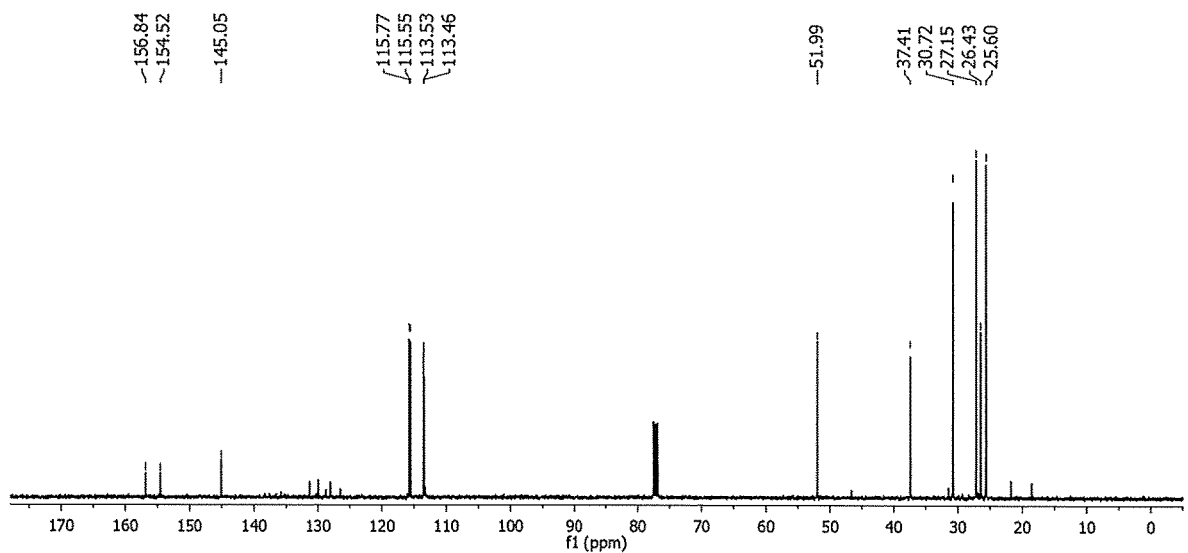
FIG. 12 is a $^{13}$C NMR spectrum (75 MHz, CDCl$_3$, 298 K) of N-(cyclooctylmethyl)-4-fluoroaniline.

FIG. 11 is a $^1$H NMR spectrum (300 MHz, CDCl$_3$, 298 K) of N-(cyclooctylmethyl)-4-fluoroaniline. FIG. 12 is a $^{13}$C NMR spectrum (75 MHz, CDCl$_3$, 298 K) of N-(cyclooctylmethyl)-4-fluoroaniline

N-(2-methyloctyl)-4-(trifluoromethoxy)aniline

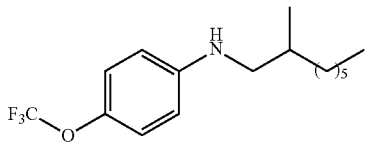

N-methyl-4-(trifluoromethoxy)aniline (96 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 3 h. Yield 92%. $^1$H NMR (CDCl$_3$, 300 MHz, 298 K): δ 7.03 (d, $J_{H-H}$=8.2 Hz, 2H, m-C$_6$H$_4$), 6.59-6.50 (m, 2H, o-C$_6$H$_4$), 3.80 (br s, 1H, NH), 3.03 (dd, $J_{H-H}$=5.9, 12.2 Hz, 1H, NC(H)H), 2.85 (dd, $J_{H-H}$=7.3, 12.2 Hz, 1H, NC(H)H), 1.82-1.64 (m, 1H, CH), 1.51-1.09 (m, 10H, CH$_2$), 0.97 (d, $J_{H-H}$=6.7 Hz, 3H, CHCH$_3$), 0.90 (t, $J_{H-H}$=6.9 Hz, 3H, CH$_2$CH$_3$) ppm. $^{13}$C NMR (CDCl$_3$, 300 MHz, 298 K): δ 147.51 (i-C$_6$H$_5$), 122.53 (C$_8$H$_5$), 112.89 (C$_6$H$_5$), 50.67 (NCH$_2$), 34.90, 33.02, 32.00, 29.73, 27.07, 22.81, 18.17 (CH$_3$), 14.23 (CH$_3$) ppm. $^{19}$F NMR (CDCl$_3$, 282.4 MHz, 298 K): δ−58.81 (s, 3F, CF$_3$) ppm.

Figure 13:
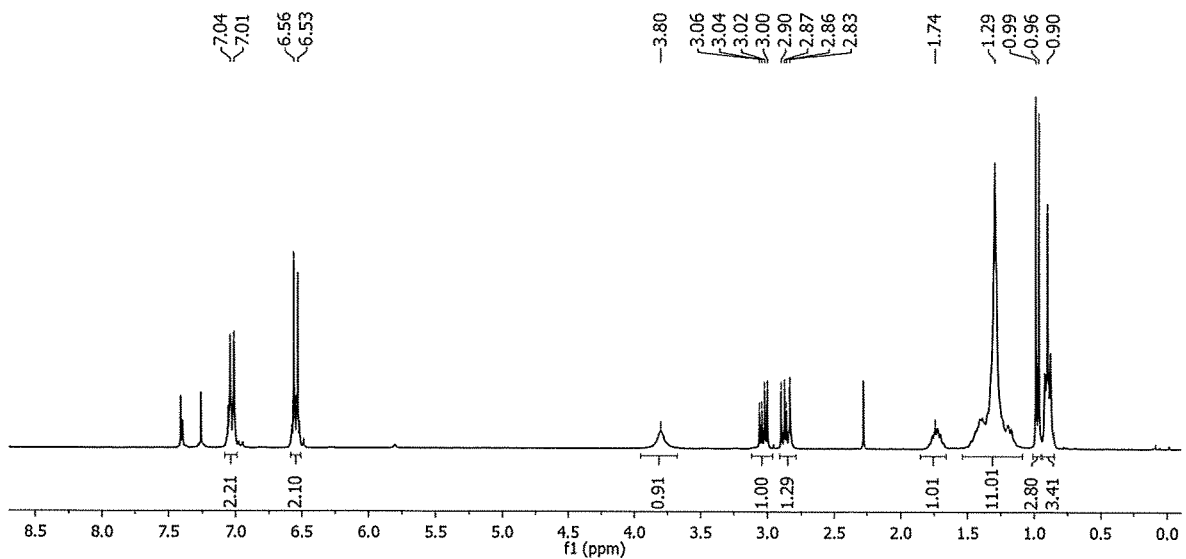
FIG. 13 is a $^1$H NMR spectrum (300 MHz, CDCl$_3$, 298 K) of N-(2-methyloctyl)-4-(trifluoromethoxy)aniline.
Figure 14:
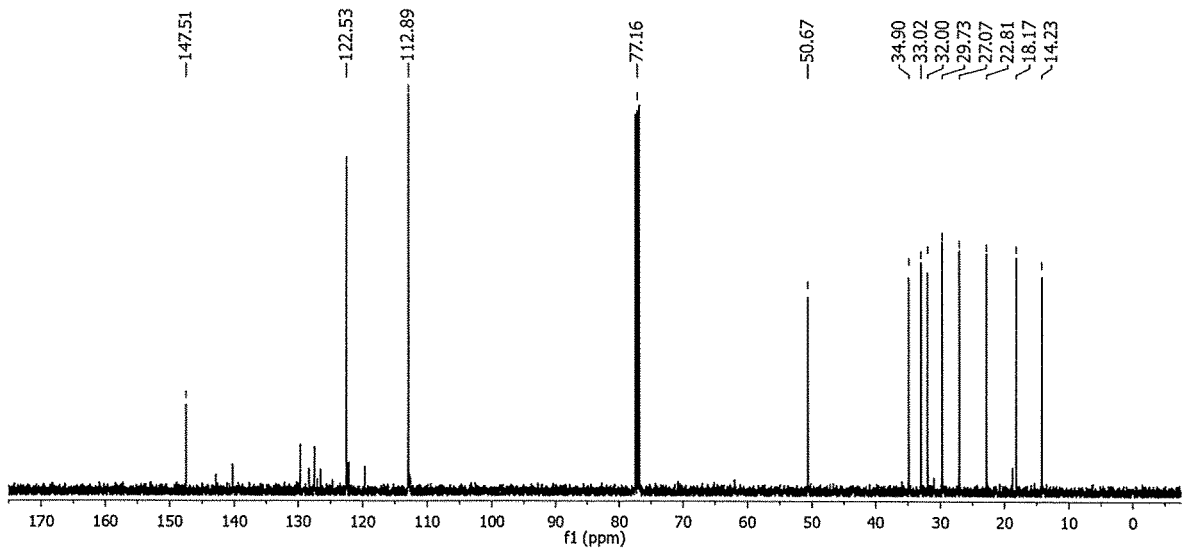
FIG. 14 is a $^{13}$C NMR spectrum (75 MHz, CDCl$_3$, 298 K) of N-(2-methyloctyl)-4-(trifluoromethoxy)aniline.

FIG. 13 is a $^1$H NMR spectrum (300 MHz, CDCl$_3$, 298 K) of N-(2-methyloctyl)-4-(trifluoromethoxy)aniline. FIG. 14 is a $^{13}$C NMR spectrum (75 MHz, CDCl$_3$, 298 K) of N-(2-methyloctyl)-4-(trifluoromethoxy)aniline.

N-(cyclooctylmethyl)-4-(trifluoromethoxy)aniline

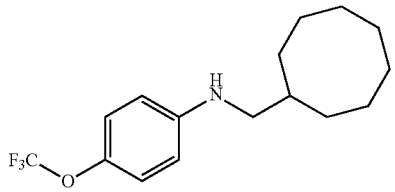 [SMILES: FC(F)(F)Oc1ccc(NCC2CCCCCCC2)cc1]

N-methyl-4-(trifluoromethoxy)aniline (96 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 85%. $^1$H NMR (CDCl$_3$, 300 MHz, 298 K): δ 7.03 (d, $J_{H-H}$=9.0 Hz, 2H, m-C$_6$H$_4$), 6.59-6.50 (m, 2H, o-C$_6$H$_4$), 3.77 (br s, 1H, NH), 2.92 (d, $J_{H-H}$=6.5 Hz, 1H, NCH$_2$), 1.89-1.21 (overlapping m, 13H, CH and CH$_2$) ppm. $^{13}$C NMR (CDCl$_3$, 75 MHz, 298 K): δ 147.55 (i-C$_6$H$_4$), 122.51 (C$_6$H$_4$), 112.81 (C$_6$H$_4$), 51.43 (NCH$_2$), 37.48, 30.73, 27.17, 26.44, 25.61 ppm. $^{19}$F NMR (CDCl$_3$, 282.4 MHz, 298 K): δ−58.79 (s, 3F, CF$_3$) ppm.

Figure 15:
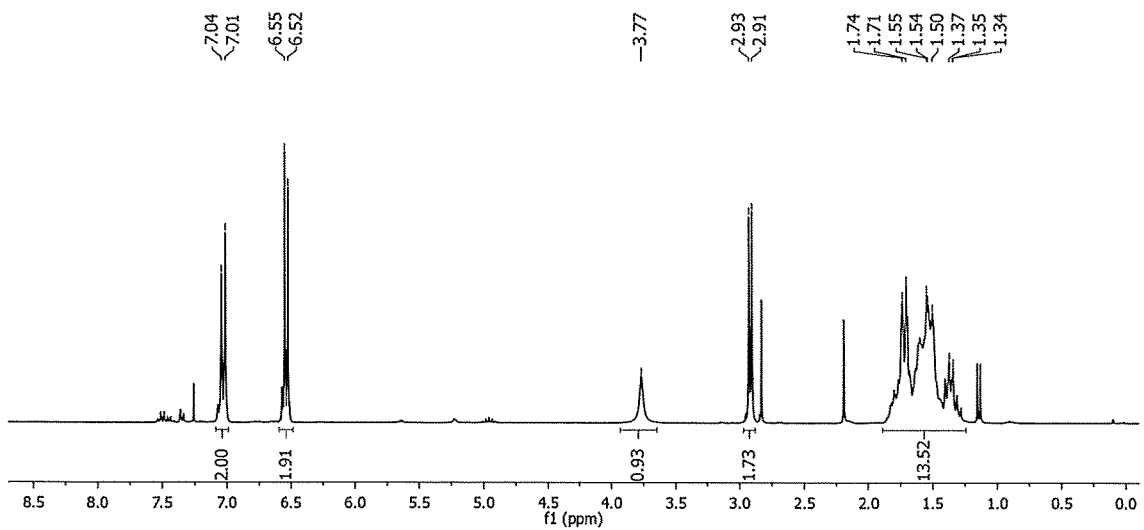
FIG. 15 is a $^1$H NMR spectrum (300 MHz, CDCl$_3$, 298 K) of N-(cyclooctylmethyl)-4-(trifluoromethoxy)aniline.
Figure 16:
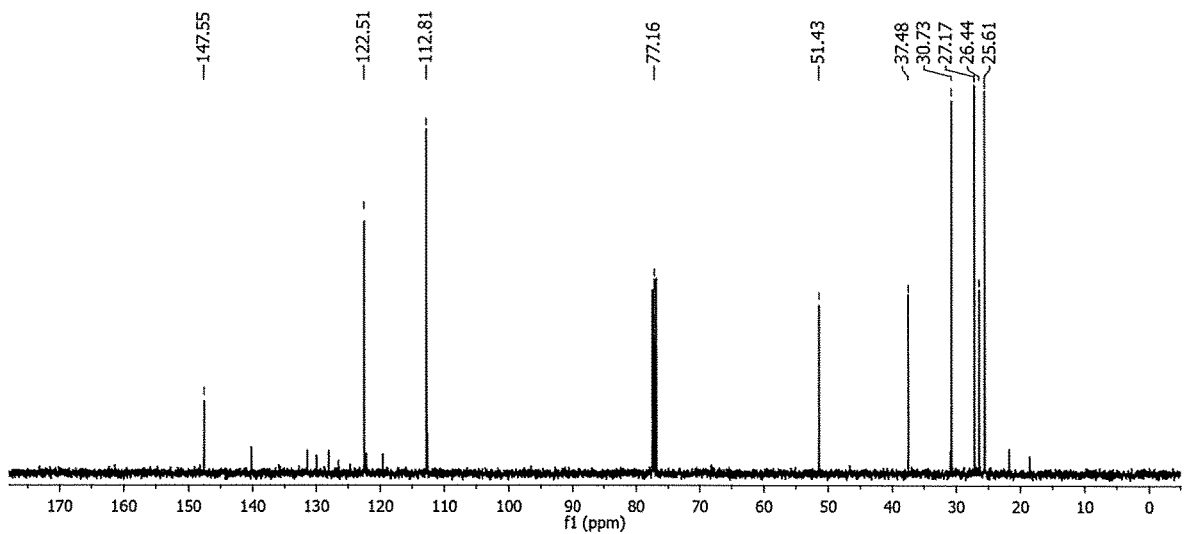
FIG. 16 is a $^{13}$C NMR spectrum (75 MHz, CDCl$_3$, 298 K) of N-(cyclooctylmethyl)-4-(trifluoromethoxy)aniline.

FIG. 15 is a $^1$H NMR spectrum (300 MHz, CDCl$_3$, 298 K) of N-(cyclooctylmethyl)-4-(trifluoromethoxy)aniline. FIG. 16 is a $^{13}$C NMR spectrum (75 MHz, CDCl$_3$, 298 K) of N-(cyclooctylmethyl)-4-(trifluoromethoxy)aniline.

N-(2-methyloctyl)benzo[d][1,3]dioxol-5-amine

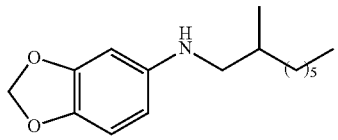

N-methylbenzo[d][1,3]dioxol-5-amine (76 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 85%. $^1$H NMR (CDCl$_3$, 300 MHz, 298 K): δ 6.66 (d, $J_{H-H}$=8.3 Hz, 2H, m-C$_6$H$_3$), 6.25 (d, $J_{H-H}$=8.3 Hz, 1H, o-C$_6$H$_3$), 6.04 (dd, $J_{H-H}$=2.3, 8.3 Hz, 1H, o-C$_6$H$_3$), 5.85 (s, 2H, OCH$_2$), 3.48 (br s, 1H, NH), 2.99 (dd, $J_{H-H}$=5.9, 12.0 Hz, 1H, NC(H)H), 2.84 (dd, $J_{H-H}$=5.0, 12.2 Hz, 1H, NC(H)H), 1.81-1.62 (m, 1H, CH), 1.50-1.08 (m, 10H, CH$_2$), 0.97 (d, $J_{H-H}$=6.7 Hz, 3H, CHCH$_3$), 0.91 (t, $J_{H-H}$=7.1 Hz, 3H, CH$_2$CH$_3$) ppm. $^{13}$C NMR (CDCl$_3$, 75 MHz, 298 K): δ 148.46 (i-C$_6$H$_3$), 144.64 (m-C$_6$H$_3$), 139.40 (p-C$_6$H$_3$), 108.75 (m-C$_6$H$_3$), 104.34 (OCH$_2$), 100.62 (o-C$_6$H$_3$), 95.90 (o-C$_6$H$_3$), 51.54, 34.94, 33.03, 32.00, 29.74, 27.06, 22.80, 18.20 (CH$_3$), 14.23 (CH$_3$) ppm.

Figure 17:
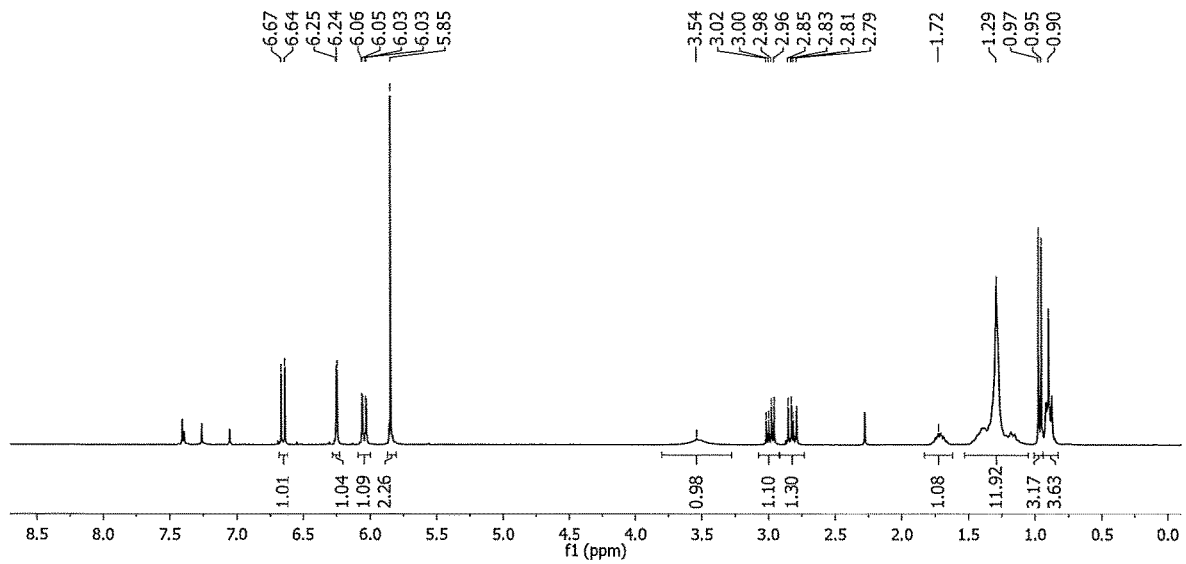
FIG. 17 is a $^1$H NMR spectrum (300 MHz, CDCl$_3$, 298 K) of N-(2-methyloctyl)benzo[d][1,3]dioxol-5-amine.
Figure 18:
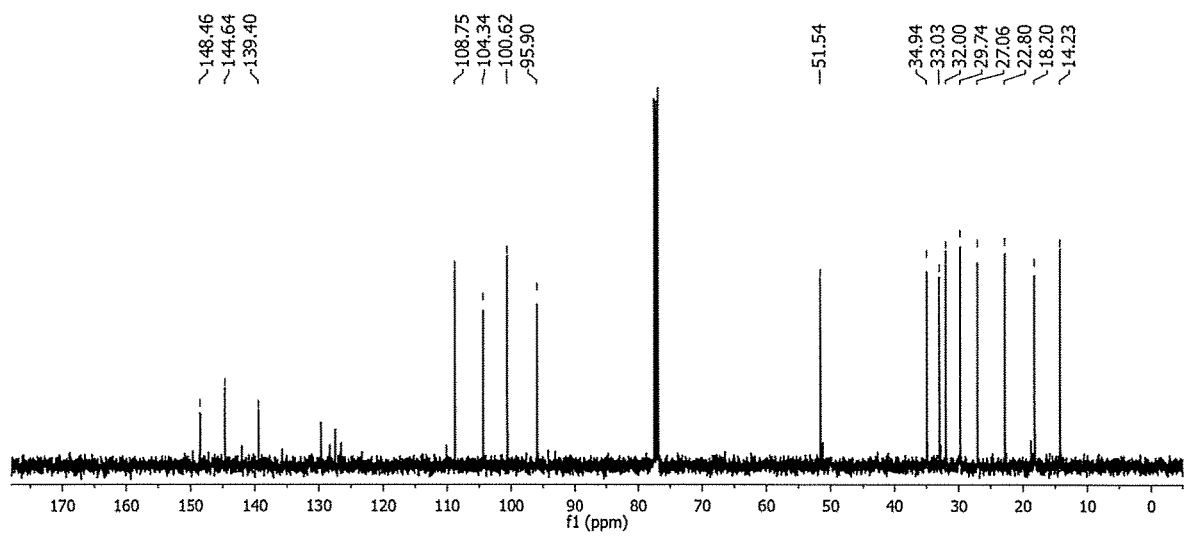
FIG. 18 is a $^{13}$C NMR spectrum (75 MHz, CDCl$_3$, 298 K) of N-(2-methyloctyl)benzo[d][1,3]dioxol-5-amine.

FIG. 17 is a $^1$H NMR spectrum (300 MHz, CDCl$_3$, 298 K) of N-(2-methyloctyl)benzo[d][1,3]dioxol-5-amine. FIG. 18 is a $^{13}$C NMR spectrum (75 MHz, CDCl$_3$, 298 K) of N-(2-methyloctyl)benzo[d][1,3]dioxol-5-amine.

N-(4-((tert-butyldimethylsilyl)oxy)-2-methylbutyl)aniline

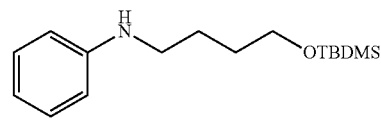 [SMILES: CC(C)(C)[Si](C)(C)OCCCCNc1ccccc1]

N-methylaniline (54 mg, 0.5 mmol), (but-3-en-1-yloxy)(tert-butyl)dimethylsilane (93 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 75%. $^1$H NMR (CDCl$_3$, 300 MHz, 298 K): δ 7.20 (t, $^3J_{H-H}$=7.8, 2H, m-C$_6$H$_4$), 6.70 (td, $^3J_{H-H}$=0.9, 7.3, 1H, p-C$_6$H$_4$), 6.63 (d, $^3J_{H-H}$=8.5, 2H, o-C$_6$H$_4$), 3.85 (br s, 1H, NH), 3.83-3.64 (m, 2H, OCH$_2$), 3.10 (dd, $J_{H-H}$=6.3, 12.2 Hz, 1H, NC(H)H), 2.97 (dd, $J_{H-H}$=6.9, 12.2 Hz, 1H, NC(H)H), 1.97 (oct, $J_{H-H}$=6.7 Hz, 1H, OCH$_2$C(H)H), 1.76-1.61 (m, 1H, CHCH$_3$), 1.53-1.39 (m, 1H, OCH$_2$C(H)H), 0.95 (d, $J_{H-H}$=1.3 Hz, 9H, SiC(CH$_3$)$_3$), 0.10 (d, $J_{H-H}$=1.1 Hz, 6H, SiCH$_3$) ppm. $^{13}$C NMR (CDCl$_3$, 75 MHz, 298 K): δ 148.71 (i-C$_6$H$_5$), 129.33 (m-C$_6$H$_5$), 117.00 (p-C$_6$H$_5$), 112.74 (o-C$_3$H$_5$), 77.16 (OCH$_2$), 61.20 (NCH$_2$), 50.43 (OCH$_2$CH$_2$), 37.94, 29.98, 26.10 (SiC(CH$_3$)$_3$), 18.44 (CHCH$_3$), −5.18 (SiCH$_3$) ppm.

Figure 19:
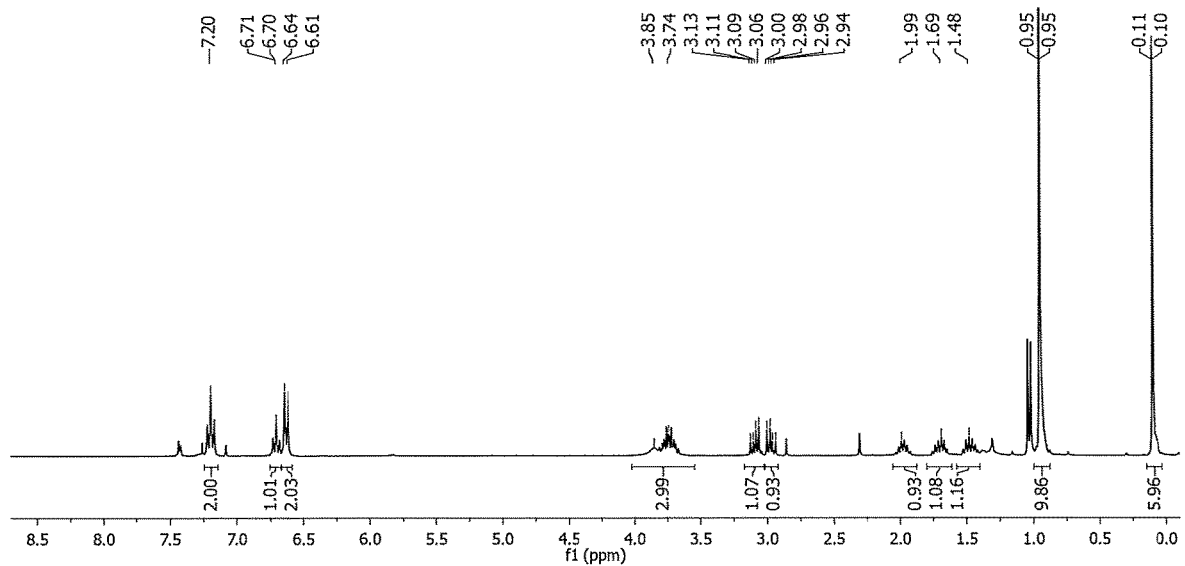
FIG. 19 is a $^1$H NMR spectrum (300 MHz, CDCl$_3$, 298 K) of 4-((tert-butyldimethylsilyl)oxy)-2-methylbutyl)aniline.
Figure 20:
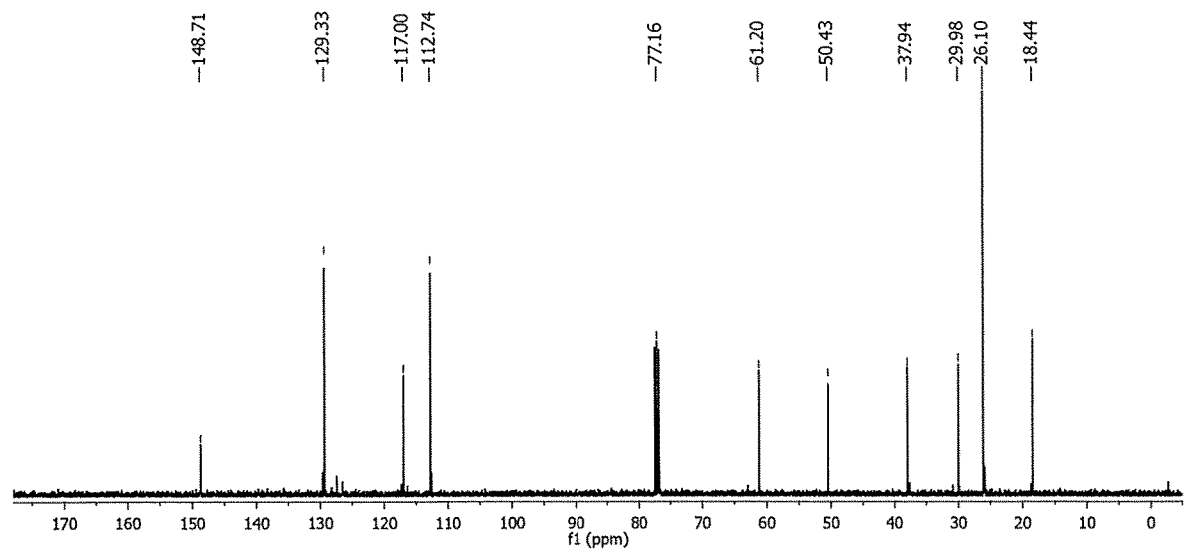
FIG. 20 is a $^{13}$C NMR spectrum (75 MHz, CDCl$_3$, 298 K) of 4-((tert-butyldimethylsilyl)oxy)-2-methylbutyl)aniline.

FIG. 19: $^1$H NMR spectrum (300 MHz, CDCl$_3$, 298 K) of 4-((tert-butyldimethylsilyl)oxy)-2-methylbutyl)aniline. FIG. 20 is a $^{13}$C NMR spectrum (75 MHz, CDCl$_3$, 298 K) of 4-((tert-butyldimethylsilyl)oxy)-2-methylbutyl)aniline.

N-(2-cyclohexylpropyl)aniline

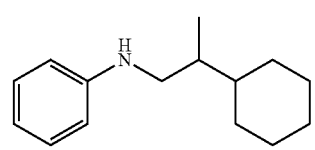 [SMILES: CC(CNc1ccccc1)C1CCCCC1]

N-methylaniline (54 mg, 0.5 mmol), vinylcyclohexane (55 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 86%. $^1$H NMR (CDCl$_3$, 300 MHz, 298 K): δ 7.25-7.17 (m, 2H, m-C$_6$H$_4$), 6.79-6.69 (m, 1H, p-C$_6$H$_4$), 6.69-6.63 (m, 2H, o-C$_6$H$_4$) 3.87 (br s, 1H, NH), 3.20 (dd, J$_{H-H}$=5.5, 12.1 Hz, 1H, NC(H)H), 2.93 (dd, J$_{H-H}$=7.9, 12.1 Hz, 1H, NC(H)H), 1.87-1.60 (overlapping m, 6H, CH and CH$_2^{Cy}$), 1.47-1.04 (m, 6H, CH$_2^{Cy}$), 0.99 (d, J$_{H-H}$=6.9 Hz, 3H, CHCH$_3$) ppm.

N-((1-methylcyclohexyl)methyl)aniline

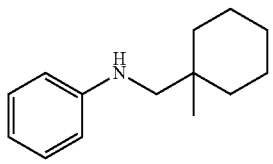

N-methylaniline (54 mg, 0.5 mmol), vinylcyclohexane (48 mg, 0.5 mmol), Ta(CH$_2$SiMe$_3$)$_3$Cl$_2$ (13 mg, 0.025 mmol), L4 (8 mg, 0.025 mmol). Reaction time: 3 h. Yield 99%. $^1$H NMR (CDCl$_3$, 300 MHz, 298 K): δ 7.30-7.21 (m, 2H, m-C$_6$H$_5$), 6.82-6.66 (overlapping m, 3H, o-C$_6$H$_3$ and p-C$_6$H$_3$), 3.68 (br s, 1H, NH), 3.03 (s, 2H, NCH$_2$), 1.69-1.33 (overlapping m, 10H, CH$_2^{Cy}$), 1.08 (s, 3H, CH$_3$) ppm.

N-(2-(cyclohex-3-en-1-yl)propyl)aniline

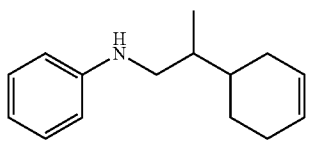 [SMILES: CC(CNc1ccccc1)C1CC=CCC1]

N-methylaniline (54 mg, 0.5 mmol), vinylcyclohexane (55 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 98%. $^1$H NMR (CDCl$_3$, 300 MHz, 298 K): δ 7.28-7.17 (m, 2H, m-C$_6$H$_5$), 6.75 (t, J$_{H-H}$=6.8 Hz, 1H, m-C$_6$H$_5$), 6.67 (d, J$_{H-H}$=7.8 Hz, 1H, o-C$_6$H$_5$), 5.75 (s, 2H, CH=CH$_2$), 3.89 (br s, 1H, NH), 3.30-3.18 (m, 1H, NC(H)H), 3.05-2.92 (m, 1H, NC(H)H), 2.25-1.24 (overlapping m, 8H, CHCH$_3$, CH$_2$CH, and CH$_2$), 1.07-0.98 (m, 3H, CH$_3$) ppm. The chemical shifts for the title compound match those reported in the literature.

N-(2-methyl-4-phenylbutyl)aniline

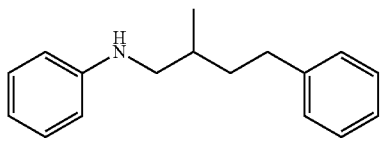 [SMILES: CC(CCc1ccccc1)CNc1ccccc1]

N-methylaniline (54 mg, 0.5 mmol), 4-phenyl-1-butene (66 mg, 0.5 mmol), Ta(CH$_2$SiMe$_3$)$_3$Cl$_2$ (13 mg, 0.025 mmol), L4 (8 mg, 0.025 mmol). Reaction time: 3 h. Yield 87%. $^1$H NMR (CDCl$_3$, 300 MHz, 298 K): δ 7.38-7.28 (m, 2H, m-C$_6$H$_5$), 7.27-7.15 (overlapping m, 5H, m-NC$_6$H$_5$, o-C$_6$H$_5$, and p-C$_6$H$_5$), 6.72 (t, J$_{H-H}$=7.1 Hz, 1H, p-NC$_6$H$_5$), 6.62 (d, J$_{H-H}$=7.9 Hz, 2H, o-NC$_6$H$_5$), 3.69 (br s, 1H, NH), 3.13 (dd, J$_{H-H}$=5.8, 12.3 Hz, 1H, NC(H)H), 2.97 (dd, J$_{H-H}$=6.9, 12.3 Hz, 1H, NC(H)H), 2.84-2.57 (m, 2H, C$_6$H$_5$CH$_2$), 1.92-1.75 (m, 2H, C$_6$H$_5$CH$_2$CH$_2$), 1.64-1.47 (m, 1H, CHCH$_3$), 1.08 (d, J$_{H-H}$=6.6 Hz, 2H, CHCH$_3$) ppm. The chemical shifts for the title compound match those reported in the literature.

N-(2-(4-chlorophenyl)propyl)aniline

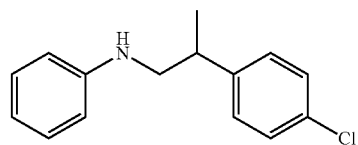 [SMILES: CC(CNc1ccccc1)c1ccc(Cl)cc1]

N-methylaniline (54 mg, 0.5 mmol), 4-chlorostyrene (70 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 98%. $^1$H NMR (CDCl$_3$, 300 MHz, 298 K): δ 7.31 (d, J$_{H-H}$=8.4 Hz, 2H, m-C$_6$H$_4$Cl), 7.23-7.14 (overlapping m, 4H, m-C$_6$H$_4$Cl and o-C$_6$H$_5$), 6.72 (t, J$_{H-H}$=7.2 Hz, 1H, p-C$_6$H$_5$), 6.59 (d, J$_{H-H}$=8.5 Hz, 2H, o-C$_6$H$_5$), 3.59 (br s, 1H, NH), 3.35 (dd, J$_{H-H}$=6.1, 12.5 Hz, 1H, NC(H)H), 3.22 (dd, J$_{H-H}$=8.2, 12.4 Hz, 1H, NC(H)H), 3.13-2.99 (m, 1H, CHCH$_3$), 1.33 (d, J$_{H-H}$=6.9 Hz, 3H, CHCH$_3$) ppm.

N-(2-(2-bromophenyl)propyl)aniline (A) and N-(3-(2-bromophenyl)propyl)aniline (B)

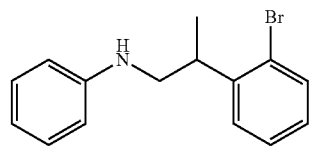

A

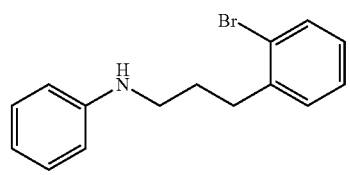

B

N-methylaniline (54 mg, 0.5 mmol), 2-bromostyrene (92 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 65%. $^1$H NMR (CDCl$_3$, 300 MHz, 298 K): Product is a combination of linear and branched HAA products (~9:1), additional spectra are required for full peak assignments.

Figure 21:
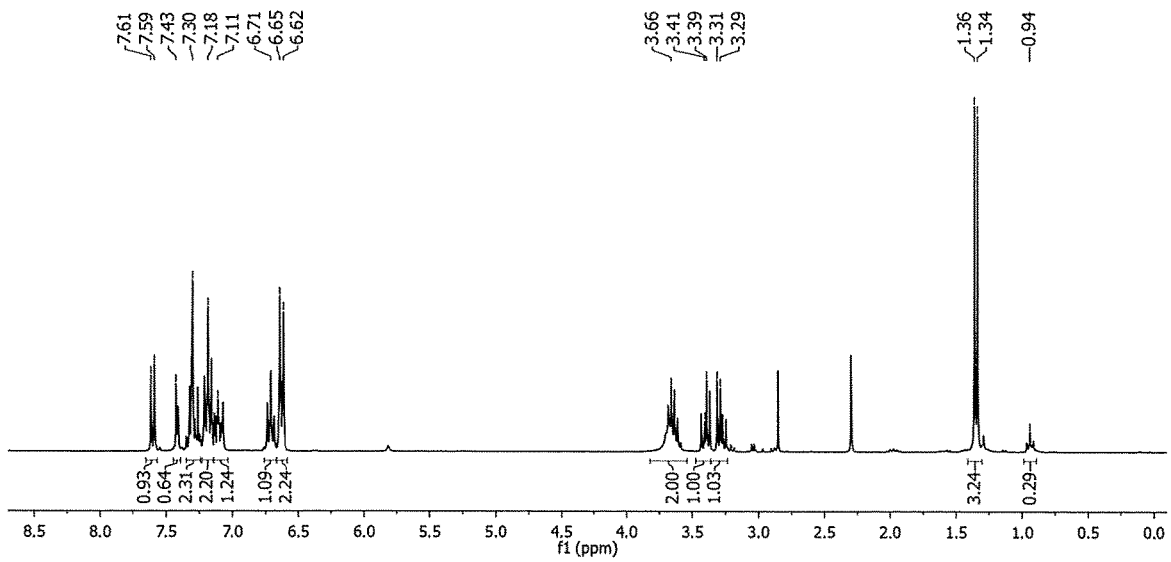
FIG. 21 is a $^1$H NMR spectrum (300 MHz, CDCl$_3$, 298 K) of a mixture between N-(2-(2-bromophenyl)propyl)aniline and N-(3-(2-bromophenyl)propyl)aniline.

FIG. 21 is a $^1$H NMR spectrum (300 MHz, CDCl$_3$, 298 K) of a mixture between N-(2-(2-bromophenyl)propyl)aniline and N-(3-(2-bromophenyl)propyl)aniline.

N-(2-methyl-3-phenylpropyl)aniline (A) and N-(2-phenylbutyl)aniline (B)

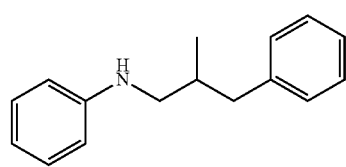

A

-continued

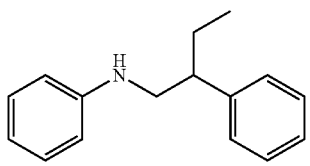

B

N-methylaniline (54 mg, 0.5 mmol), cis/trans-β-methylstyrene (60 mg, 0.5 mmol), Ta(CH$_2$SiMe$_3$)$_3$Cl$_2$ (13 mg, 0.025 mmol), L5 (8 mg, 0.025 mmol). Reaction time: 48 h. Yield 78%. $^1$H NMR (CDCl$_3$, 300 MHz, 298 K): δ 7.42-7.12 (overlapping m, 14H, m-C$_6$H$_5$$^A$, m-NC$_6$H$_5$$^A$, o,p-C$_6$H$_5$$^A$, o,m,p-C$_6$H$_5$$^B$, and m-NC$_6$H$_5$$^B$), 6.79-6.52 (overlapping m, 6H, p-NC$_6$H$_5$$^A$, o-NC$_6$H$_5$$^A$, p-NC$_6$H$_5$$^B$, and o-NC$_6$H$_5$B), 3.69 (br s, 1H, NH$^A$), 3.60-3.38 (overlapping m, 2H, NH$^B$ and NC(H)H$^B$), 3.30-3.19 (m, 1H, NC(H)H$^B$), 3.13 (dd, J$_{H-H}$=6.0, 12.4 Hz, 1H, NC(H)H$^A$), 2.98 (dd, J$_{H-H}$=6.9, 12.3 Hz, 1H, NC(H)H$^A$), 2.87-2.75 (m, 1H, C$_6$H$_5$CH$^B$), 2.79 (dd, J$_{H-H}$=6.3, 13.4 Hz, 1H, C$_6$H$_5$C(H)H$^A$), 2.53 (dd, J$_{H-H}$=6.3, 13.4 Hz, 1H, C$_6$H$_5$C(H)H$^A$), 2.18-2.03 (m, 1H, CHCH$_3$$^A$), 1.92-1.77 (m, 1H, C(H)HCH$_3$$^B$), 1.77-1.60 (m, 1H, C(H)HCH$_3$$^B$) 1.01 (d, J$_{H-H}$=6.7 Hz, CHCH$_3$$^A$) ppm.

N-(cyclohexylmethyl)aniline

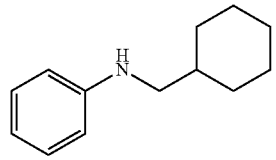 [SMILES: c1ccc(NCC2CCCCC2)cc1]

N-methylaniline (54 mg, 0.5 mmol), cyclohexene (41 mg, 0.5 mmol), Ta(CH$_2$SiMe$_3$)$_3$Cl$_2$ (13 mg, 0.025 mmol), L5 (8 mg, 0.025 mmol). Reaction time: 20 h. Yield 70%. $^1$H NMR (CDCl$_3$, 300 MHz, 298 K): δ 7.23-7.11 (m, 1H, m-C$_6$H$_5$), 6.68 (t, J$_{H-H}$=7.2 Hz, 1H, p-C$_6$H$_5$), 6.60 (d, J$_{H-H}$=8.9 Hz, 2H, o-C$_6$H$_5$), 3.70 (br s, 1H, NH), 2.96 (d, J$_{H-H}$=6.7 Hz, NCH$_2$), 1.93-1.67 (m, 5H, CH$_2$), 1.68-1.52 (m, 1H, CH), 1.39-1.21 (m, 3H, CH$_2$), 1.11-0.93 (m, 1H, CH$_2$) ppm. The chemical shifts for the title compound match those previously reported in the literature.

N-(cyclopentylmethyl)aniline

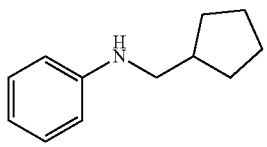 [SMILES: c1ccc(NCC2CCCC2)cc1]

N-methylaniline (54 mg, 0.5 mmol), cyclopentene (34 mg, 0.5 mmol), Ta(CH$_2$SiMe$_3$)$_3$Cl$_2$ (13 mg, 0.025 mmol), L5 (8 mg, 0.025 mmol). Reaction time: 20 h. Yield 74%. $^1$H NMR (CDCl$_3$, 300 MHz, 298 K): δ 7.21 (t, J$_{H-H}$=7.5 Hz, 2H, m-C$_6$H$_5$), 6.72 (t, J$_{H-H}$=7.3 Hz, 1H, p-C$_6$H$_5$), 6.65 (d, J$_{H-H}$=7.7 Hz, 2H, o-C$_6$H$_5$), 3.69 (br s, 1H, NH), 3.06 (d, J$_{H-H}$=7.3 Hz, 2H, NCH$_2$), 2.19 (hept, J$_{H-H}$=7.6 Hz, 1H, NCH$_2$CH), 1.94-1.80 (m, 2H, CH$_2$), 1.77-1.52 (m, 4H, CH$_2$), 1.40-1.23 (m, 2H, CH$_2$) ppm.

N-(cycloheptylmethyl)aniline

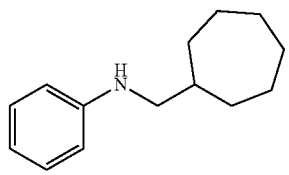 [SMILES: c1ccc(NCC2CCCCCC2)cc1]

N-methylaniline (54 mg, 0.5 mmol), cycloheptene (49 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 88%. $^1$H NMR (400 MHz, CDCl$_3$): δ 7.17 (t, J=7.4 Hz, 2H), 6.70 (t, J=7.2 Hz, 1H), 6.62 (d, J=8.0 Hz, 2H), 3.76 (br s, 1H), 2.97 (d, J=6.3 Hz, 2H), 1.90-1.40 (m, 11H), 1.35-1.20 (m, 2H).

EXAMPLES

Various alternative embodiments and examples are described herein. These embodiments and examples are illustrative and should not be construed as limiting the scope of the invention. In particular, while tantalum was used as the representative group 5 metal for these studies, the skilled person will expect other group 5 metals, and especially niobium, to perform similarly.

Example 1: Group 5 Metal-Based Precursors as Catalysts

In order to identify potentially promising group 5 metal/ligand salt combinations, the most common Ta precursors were screened in the absence of any ligand salt (Table 1). For this step, the standard benchmark reaction between N-methylaniline and 1-octene was chosen. It has previously been demonstrated that TaMe$_3$Cl$_2$ can catalyse this reaction, reaching a conversion of 91%, after 30 hours at 110° C. using a 10 mol % catalyst loading, but full conversion could never be achieved due to catalyst decay. Hence, optimization of the benchmark reaction was started by reducing the reaction time from 24 h to only 1 h. Under these conditions TaMe$_3$Cl$_2$ could afford a 28% conversion. Further catalytic screening confirmed that Ta-alkyl precursors can competently catalyse the addition of N-methylaniline to 1-octene, with Ta(CH$_2$SiMe$_3$)$_3$Cl$_2$ showing the most promising activity, achieving 39% conversion in only 1 h, when stoichiometric amounts of substrates were used. On the other hand, complexes bearing a Ta—NMe$_2$ moiety were far less reactive, at best showing a 15% conversion after 24 hours of reaction. These data illustrated the promising catalytic activity of Ta(CH$_2$SiMe$_3$)$_3$Cl$_2$. For this reason, Ta(CH$_2$SiMe$_3$)$_3$Cl$_2$ was chosen as the tantalum precursor for all subsequent catalytic experiments.

TABLE 1

Screening of Ta precursors for intermolecular hydroaminoalkylation reactions.[a]

PhNH(Me) + CH₂=CH(CH₂)₅CH₃ → (5 mol % [Ta], 110° C., d₆-toluene) → PhNH-CH₂-CH(Me)-(CH₂)₅CH₃

| Ta(CH₂SiMe₃)₃Cl₂ | Ta(CH₂CMe₃)₃Cl₂ | TaMe₃Cl₂ | Ta(NMe₂)₅ | [Ta(NMe₂)₃Cl₂]₂ |
|---|---|---|---|---|
| 1 h, 39% | 25 h, 15% | 1 h, 28% | 24 h, n.r. | 1h, n.r.; 24 h, 15% |

[a]Reaction conditions: amine (0.5 mmol), 1-octene (0.5 mmol), [Ta] precatalyst (0.025 mmol), d₈ toluene (0.6 mL). Conversion determined by ¹H NMR spectroscopy, n.r. = no reaction.

Example 2: Ligand Salt Screening Using In-Situ Experiments

Further catalytic experiments were performed by generating in situ the catalytic species by reacting Ta(CH₂SiMe₃)₃Cl₂ with a variety N,O-chelate type ligand salts.

This study was extended to internal alkenes, adding the more challenging cyclohexene to the pool of substrates. In an effort to perform the catalytic screening under milder conditions, the reaction temperature for reactions using cyclohexene as a substrate were lowered from 145° C. to 130° C. For this step, attention was focussed on amidate (Table 2, L1), phosphoramidate (Table 2, L2), and pyridonate (Table 2, L3) sodium salts. In addition, a variety of ureate type ligand salts were also investigated. The latter type of ligands have previously been studied with group 4 metals for hydroamination and alkyne dimerization catalysis. Catalytic screening of in situ mixtures containing L1 and L2 resulted in no or poor conversion, regardless of the alkene substrate or the chosen reaction time. This behaviour is somewhat surprising considering that in the case of 1-octene, the related amidate-Ta(NMe₂)₄ complex gave a 96% conversion of the addition product after 63 h of reaction time. Moreover, the in situ mixture between the ligand salt L2 and TaMe₃Cl₂ afforded 52% conversion after 20 h, at room temperature. On the other hand, using the less sterically encumbered pyridonate ligand salt L3 proved to be more successful as 31% and 33% conversions were observed for terminal and internal alkene substrates, respectively.

TABLE 2

Screening of ligand salts in hydroaminoalkylation reactions.[a]

PhNH(Me) + R₁CH=CHR₂ → (Ta(CH₂SiME₃)₂Cl₂ + L⁻Na⁺, 5 mol %, 110-130° C., d₆-toluene) → PhNH-CH₂-CH(R₂)-CH₂R₁

| Ligand Salt | Alkene: 1-octene | Alkene: cyclohexene |
|---|---|---|
| L1 (2,6-iPr-C₆H₃-N(Na)-C(O)-tBu) | 1 h, n.r. | 20 h, n.r. |

TABLE 2-continued
Screening of ligand salts in hydroaminoalkylation reactions.[a]
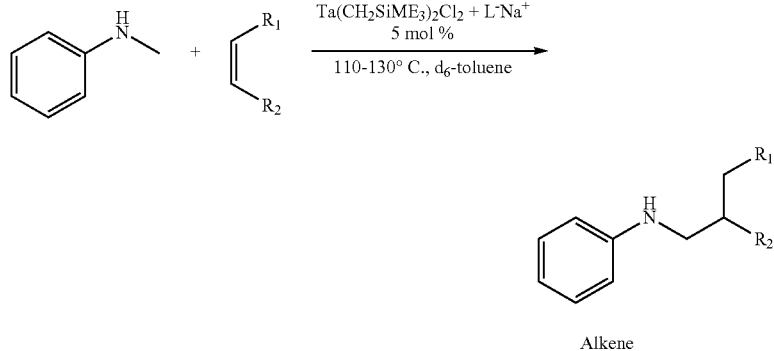
| Ligand Salt | | Alkene | |
| --- | --- | --- | --- |
| | | 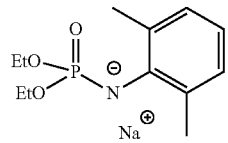 | 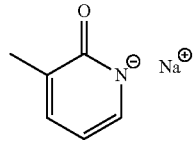 |
| 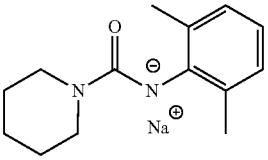 [SMILES: Cc1cccc(C)c1[N-]C(=O)N1CCCCC1 ; [Na+]] | L2 | 1 h, n.r. | 20 h, n.r. |
| 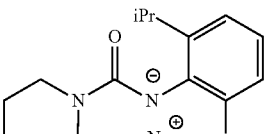 | L3 | 1 h, 31% | 20 h, 33% |
| 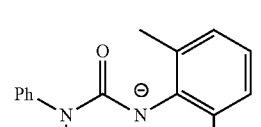 | L4 | 1 h, 55% | 24 h, 58%[d] |
| 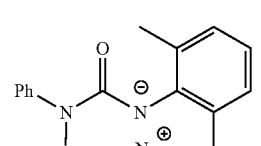 | L5 | 1 h, 37% | 20 h, 34% |
| 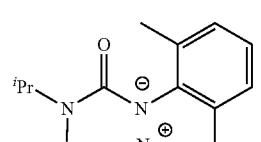 | L6 | 1 h, 83% | 20 h, 19% |
|  | L7 | 1 h, 12% | 20 h, 83% |
|  | L8 | 1 h, 5% | 20 h, 6% |

TABLE 2-continued

Screening of ligand salts in hydroaminoalkylation reactions.[a]

$$\text{PhNHMe} + \text{alkene} \xrightarrow[\text{110-130° C., } d_6\text{-toluene}]{\text{Ta(CH}_2\text{SiME}_3)_2\text{Cl}_2 + \text{L}^-\text{Na}^+ \quad 5 \text{ mol \%}} \text{PhNHCH}_2\text{CHR}_2\text{R}_1$$

| Ligand Salt | | Alkene: 1-octene | Alkene: cyclohexene |
|---|---|---|---|
| L9 (Ph-N(Me)-C(O)-N(2,6-Me₂C₆H₃)⁻ Na⁺) | | 1 h, 48% | 20 h, 45% |
| L10 (Cy-N(Me)-C(O)-N(2,6-Me₂C₆H₃)⁻ Na⁺) | | 1 h, 45% | n/a |
| L11 (Cy-N(Cy)-C(O)-N(2,6-Me₂C₆H₃)⁻ Na⁺) | | 1 h, traces | n/a |
| L12 (N-Cy, iPr-substituted imidazolidinonate Na⁺) | | 1 h, 93% | n/a |
| L13 (N-tBu, iPr-substituted imidazolidinonate Na⁺) | | 1 h, 92% | n/a |

[a]Reaction conditions: amine (0.5 mmol), alkene (0.5 mmol), Ta(CH₂SiMe₃)₃Cl₂ (0.025 mmol), ligand salt (0.025 mmol), $d_8$-toluene (0.5 g). Conversion was determined by $^1$H NMR spectroscopy. n.r. = no reaction. All reactions with 1-octene were performed at 110° C., while those with cyclohexene were performed at 130° C.

Next, ureate salts were tested. In situ catalyst system with L6 was excellent, affording 83% conversion in only 1 h for the reaction between 1-octene and N-methylaniline with a TOF of more than 16 h$^{-1}$. However, when the more challenging cyclohexene substrate was evaluated, only a modest 19% conversion was observed after 20 h. Remarkably, the mixed aryl/alkyl-substituted ureate ligand L7 resulted in a reversed trend; this system provided higher conversion of the internal alkene substrate (20 h, 83%), but was less effective for the terminal alkene substrate (1 h, 12%). These results are surprising considering that the only change is the N-Ph group of L6 to the N-iPr moiety in L7. Exchanging the remaining Ph group of L7 with an iPr group (L8) did not improve the catalytic system and poor conversions were obtained for both alkenes. Without wishing to be bound by an particular theory, the inventors propose that that the known hemilability of N,O-chelating ligands coupled with the variable coordination modes of ureate ligands results in a flexible coordination environment about the reactive metal center, thereby promoting reactivity.

Table 3 provides additional data with respect to the effect of various ureate ligand salts on the addition of N-methylaniline to 1-octene.

TABLE 3

Screening of ligand salts in hydroaminoalkylation reactions in which N-methylaniline is added to 1-octene.

| Ligand | Temperature (° C.) | Time (h) | Conversion (%) |
|---|---|---|---|
| piperidine-ureate (2,6-dimethylphenyl), Na⁺ | 110 | 1 | 55 |
| Ph,Ph-ureate (2,6-dimethylphenyl), Na⁺ | 110 | 2 | 95 |
| Ph,iPr-ureate (2,6-dimethylphenyl), Na⁺ | 110 | 1 | 23 |
| iPr,iPr-ureate (2,6-dimethylphenyl), Na⁺ | 110 | 1 | 5 |
| piperidine-ureate (2,6-diisopropylphenyl), Na⁺ | 110 | 1 | 37 |
| Ph,Me-ureate (2,6-dimethylphenyl), Na⁺ | 110 | 1 | 48 |

TABLE 3-continued
Screening of ligand salts in hydroaminoalkylation reactions in which N-methylaniline is added to 1-octene.
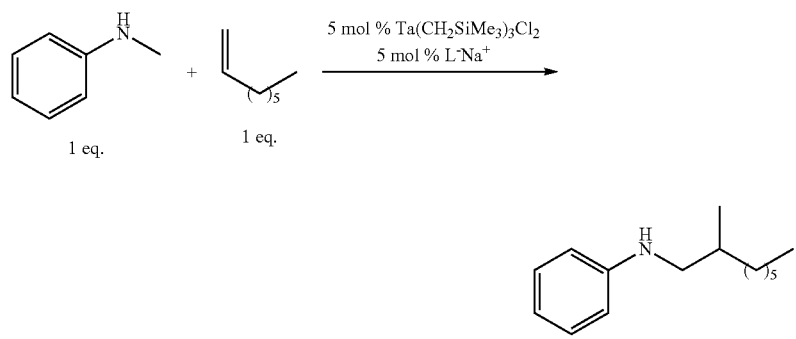
| Ligand | Temperature (° C.) | Time (h) | Conversion (%) |
|---|---|---|---|
| Cy-N(Me)C(O)N(Na)-(2,6-Me₂C₆H₃) | 110 | 1 | 45 |
| Cy-N(Cy)C(O)N(Na)-(2,6-Me₂C₆H₃) | 110 | 1 | 0 |
| MeN(CH(Me)Ph)C(O)N(Na)-(2,6-Me₂C₆H₃) | 110 | 1 | 99 |
| MeN(iPr)C(O)N(Na)-(2,6-Me₂C₆H₃) | 110 | 1 | 40 |
| MeN(CHPh₂)C(O)N(Na)-(2,6-Me₂C₆H₃) | 110 | 1 | 20 |
| MeN(CH(Me)Ph)C(O)N(Na)-(2,6-iPr₂C₆H₃) | 110 | 1 | 30 |

TABLE 3-continued
Screening of ligand salts in hydroaminoalkylation reactions in which N-methylaniline is added to 1-octene.
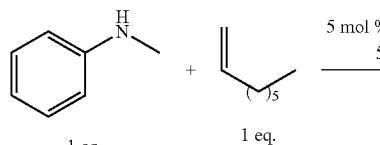
| Ligand | Temperature (° C.) | Time (h) | Conversion (%) |
|---|---|---|---|
| 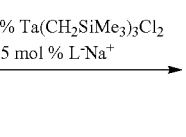 | 110 | 24 | 100 |
|  | 110 | 1 | 31 |
|  | 110 | 0.25 | 67 |
|  | 110 | 0.5 | 87 |
|  | 100 | 1 | 93 |
|  | 110 | 0.5 | 36 |
Table 4 provides additional data with respect to the effect of various ureate ligand salts on the addition of N-methylaniline to cyclohexene.

TABLE 4

Screening of ligand salts in hydroaminoalkylation reactions in which N-methylaniline is reacted with cyclohexene.

| Ligand | Temperature (° C.) | Time (h) | Conversion (%) |
|---|---|---|---|
| piperidine-C(=O)-N(Na)-(2,6-dimethylphenyl) | 145 | 24 | 58 |
| Ph₂N-C(=O)-N(Na)-(2,6-dimethylphenyl) | 130 | 20 | 35 |
| Ph(iPr)N-C(=O)-N(Na)-(2,6-dimethylphenyl) | 130 | 20 | 83 |
| (iPr)₂N-C(=O)-N(Na)-(2,6-dimethylphenyl) | 145 | 20 | 6 |
| piperidine-C(=O)-N(Na)-(2,6-diisopropylphenyl) | 145 | 20 | 34 |
| Ph(Me)N-C(=O)-N(Na)-(2,6-dimethylphenyl) | 130 | 20 | 45 |
| Cy(Me)N-C(=O)-N(Na)-(2,6-dimethylphenyl) | 130 | 20 | 0 |

TABLE 4-continued

Screening of ligand salts in hydroaminoalkylation reactions in which N-methylaniline is reacted with cyclohexene.

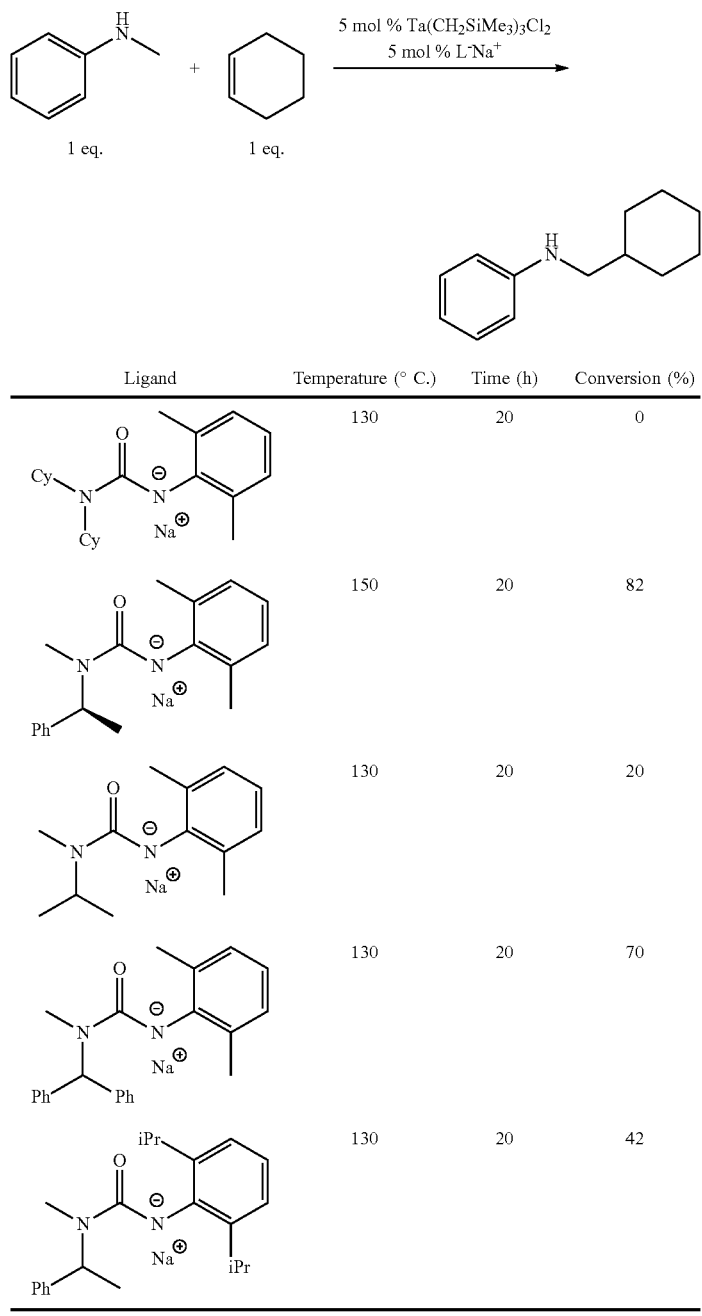

| Ligand | Temperature (° C.) | Time (h) | Conversion (%) |
|---|---|---|---|
| (Cy,Cy-urea ligand) | 130 | 20 | 0 |
| (Ph-CH(Me)-, Me-urea ligand) | 150 | 20 | 82 |
| (iPr, Me-urea ligand) | 130 | 20 | 20 |
| (Ph2CH-, Me-urea ligand) | 130 | 20 | 70 |
| (Ph-CH(Me)-, Me-urea ligand with 2,6-iPr aryl) | 130 | 20 | 42 |

Example 3: Amine Substrate Scope

The study referred to in Tables 2 and 3 was extended by broadening the substrate scope in amine substrates. 1-Octene was kept as the preferred substrate for the terminal alkenes, whereas cyclohexene was swapped with cyclooctene, due to higher reactivity caused by the ring strain. As indicated in Table 5, catalytic mixtures including L6 were used to convert the terminal alkene, while ligand salt L7 was used exclusively for the internal alkene. Another objective was to purify the final products in an easy manner, by avoiding separation on the chromatographic column. For this reason, reaction times were adapted in order to favour full substrate conversion i.e. 2 h for 1-octene and 6 h for cyclooctene. As expected, the reaction between N-methylaniline and 1-octene (Table 5, Entry 1), resulted in a nearly complete conversion of the substrates with a TOF value of 9.5 $h^{-1}$. Likewise, cyclooctene was fully converted within 6 hours, with an average of 3.3 turnovers per hour and an excellent 83% isolated yield (Table 5, Entry 1 b). The pyridonate-Ta(NMe$_2$)$_3$Cl$_2$ complex can also catalyse this reaction, but in this case longer reaction times are needed (20 h), with a TOF value limited to 1 $h^{-1}$. Consistently with results reported in the literature, para-substituted N-methylanilines are well tolerated and good TOF values were recorded for both 1-octene (3-3.3 h$^{-1}$) and cyclooctene (8.8-10 h$^{-1}$) substrates. On the same note, the presence of halide substituents on the aromatic ring (Table 5, Entries 3-5) does not inhibit the reaction rates, opening the way for further functionalization via cross-coupling or nucleophilic aromatic substitution reactions. Perhaps more importantly, the potential pharmaceutically relevant aniline N-methyl-4-(trifluoromethoxy)aniline (Table 5, Entry 6) proved to be highly reactive under the specified catalytic conditions. Impressively, the presence of a dioxole unit was also well tolerated, as the corresponding addition product was easily obtained with an 85% yield.

TABLE 5

Substrate scope in amine$^a$

| Entry | Amine | Alkene | Isolated Yield (%) |
|---|---|---|---|
| 1 | N-methylaniline | a | 88 |
| 2 | | b | 83 |
| 3 | 4-methoxy-N-methylaniline | a | 77 |
| 4 | | b | 70 |
| 5 | 4-bromo-N-methylaniline | a | 86 |
| 6 | | b | 95 |
| 7 | 4-chloro-N-methylaniline | a | 90 |
| 8 | | b | 93 |
| 9 | 4-fluoro-N-methylaniline | a | 85 |
| 10 | | b | 88 |
| 11 | N-methyl-4-(trifluoromethoxy)aniline | a | 92 |
| 12 | | b | 85 |
| 13 | N-methyl-1,3-benzodioxol-5-amine | a | 85 |

$^a$Reaction conditions: amine (0.5 mmol), alkene (0.5 mmol), Ta(CH$_2$SiMe$_3$)$_3$Cl$_2$ (0.025 mmol), ligand salt (0.025 mmol), d$_8$-toluene (0.5 g). L4 was used for all terminal alkene substrates at 110° C. over 2 h and L5 was used for internal alkene substrates at 130° C. over 6 h.

Table 6 provides additional data with respect to the addition of various amines to 1-octene in the presence of tantalum metal complexes.

TABLE 6

Amine scope for hydroaminoalkylation reactions.

| Entry | Amine | Alkene | Temperature (° C.) | Time (h) | Conversion (%) | dr |
|---|---|---|---|---|---|---|
| 1 | tetrahydroisoquinoline | 1-octene | 150 | 20 | 100 | 16:1 |

TABLE 6-continued

Amine scope for hydroaminoalkylation reactions.

| Entry | Amine | Alkene | Temperature (° C.) | Time (h) | Conversion (%) | dr |
|---|---|---|---|---|---|---|
| 2 | 1-phenylpiperazine | 1-heptene | 150 | 20 | 65 | >20:1 |
| 3 | 1,2,3,4-tetrahydroquinoline | 1-heptene | 150 | 20 | | >20:1 |
| 4 | 4-benzylpiperidine | 1-heptene | 150 | 20 | 100 | 10:1 |
| 5 | 3-methylpiperidine | 1-heptene | 150 | 20 | 100 | >20:1 |
| 6 | 4-methylpiperidine | 1-heptene | 150 | 20 | 100 | 8:1 |
| 7 | azepane | 1-heptene | 150 | 20 | 100 | >20:1 |
| 8 | Ph,Ph-substituted N-methyl amine with allyl | n/a | 150 | 20 | 100 | n/a |
| 9 | N-methylbenzylamine | 1-heptene | 150 | 20 | 100 | 1:1 regioisomers dr >20:1 |
| 10 | piperidine | 4-vinylcyclohexene | 150 | 20 | 100 | >20:1 |

TABLE 6-continued

Amine scope for hydroaminoalkylation reactions.

| Entry | Amine | Alkene | Temperature (° C.) | Time (h) | Conversion (%) | dr |
|---|---|---|---|---|---|---|
| 11 | piperidine | 2-bromostyrene | 110 | 20 | 90 | TBD |
| 12 | piperidine | CH$_2$=CHCH$_2$CH$_2$OTBDMS | 150 | 20 | 100 | dr TBD |
| 13 | piperidine | trans-2-hexene | 150 | 20 | 50 | drTBD |
| 14 | piperidine | norbornene | 150 | 2 | 100 | >20:1 Mostly bis-alkylated product obtained |
| 15 | piperidine | styrene | 150 | 20 | 100 | 1.79:1 (Branched:Linear regioisomers) dr 17:1 |
| 16 | piperidine | 4-chlorostyrene | 150 | 20 | 100 | 1.2:1 (Branched:Linear regioisomers) dr 19:1 |

Reaction scheme: R$_1$R$_2$NH-CH$_2$ + CH$_2$=CHR$_3$ (1 eq. each), 5 mol% Ta(CH$_2$SiMe$_3$)$_3$Cl$_2$, 5 mol% urea-based sodium salt co-catalyst → R$_1$NH-CH(R$_2$)-CH(CH$_3$)-R$_3$ type product.

Example 4: Alkene Substrate Scope

Having tested the capability of the Ta(CH$_2$SiMe$_3$)$_3$Cl$_2$ containing catalytic system in broadening the substrate scope in amines, attention was switched to the alkene class of substituents (Table 7). In this respect, a variety of terminal, di-substituted alkenes and dienes were chosen as candidates. As before, L6 was used exclusively for terminal alkenes, while L7 was used in the case of the internal ones. Alkenes containing silyl protected OH moieties were easily reacted with N-methylaniline in less than 2 h to give the addition product in a 75% yield, and with an average of 8.6 turnovers per hour. Further catalytic screenings involved trimethyl(vinyl)silane, which upon reaction with N-methylaniline gives a 1:1 mixture (TOF=9.0 h$^{-1}$) between the branched and linear product, perhaps as a consequence of the β-silicon effect. Even sterically hindered alkenes such as vinylcyclohexene and methylenecyclohexane are accommodated giving the corresponding addition products in excellent yields and TOF values of 9.1 h$^{-1}$ and 6.6 h$^{-1}$, respectively. Remarkably, 4-vinylcyclohex-1-ene was highly reactive under catalytic conditions (99% yield, TOF=10 h$^{-1}$), when only the terminal C=C bond was selectively activated. This result is impressive as isolated dienes are particularly difficult to convert. Styrenes are no exception to the active class of substituents as 4-chlorostyrene and 2-bromo-styrene reacted quantitatively (TOF=10 and 10 h$^{-1}$) with the amine, with no signs of polymerized product being observed. In the case of 2-bromo-styrene, the presence of the halide atom in the ortho position on the aryl ring notably does not sterically affect the outcome of the reaction. This observation is counterintuitive considering that under identical conditions, 2-methylstyrene was found to be completely inert.

The substrate scope containing the more challenging internal alkenes was investigated next. First, α-methylstyrene required long reaction times (48 h) to ensure an almost complete conversion. α-methylstyrene can be fully converted in 24 h when the catalyst is supported by the smaller pyridonate type of ligands. The reactivity of cyclic internal alkenes was found to be directly proportional to the size of the ring, and therefore dependent on the ring strain. Hence, cyclooctene was found to be the most reactive (TOF=3.2 h$^{-1}$), followed by cycloheptene (TOF=3 h$^{-1}$), while cyclopentene (TOF=0.79 h$^{-1}$) and cyclohexene (TOF=0.80 h$^{-1}$) displayed a similar reactivity. Absence of the ring strain, as observed for the internal linear alkenes had a clear impact on the reactivity of these substrates. Indeed, compared to the cyclic alkenes, only moderate yields were obtained after 20 h i.e. 4-octene (55%), cis-3-hexene (55%), trans-3-hexene (32%).

TABLE 7

Substrate scope in alkene.$^{a,b}$ Turnover frequency values (h) are given in brackets. Ratio of branched:linear regioisomers are given in square brackets

75% (8.6)

51% (9.0) [1:1]$^b$

86% (9.1)

99% (6.6)

99% (10)

86% (9.1)

98% (10)

65% (10)

78% (0.4) [2.3:1]

75% (0.79)

TABLE 7-continued

Substrate scope in alkene.[a,b] Turnover frequency values (h) are given in brackets. Ratio of branched:linear regioisomers are given in square brackets

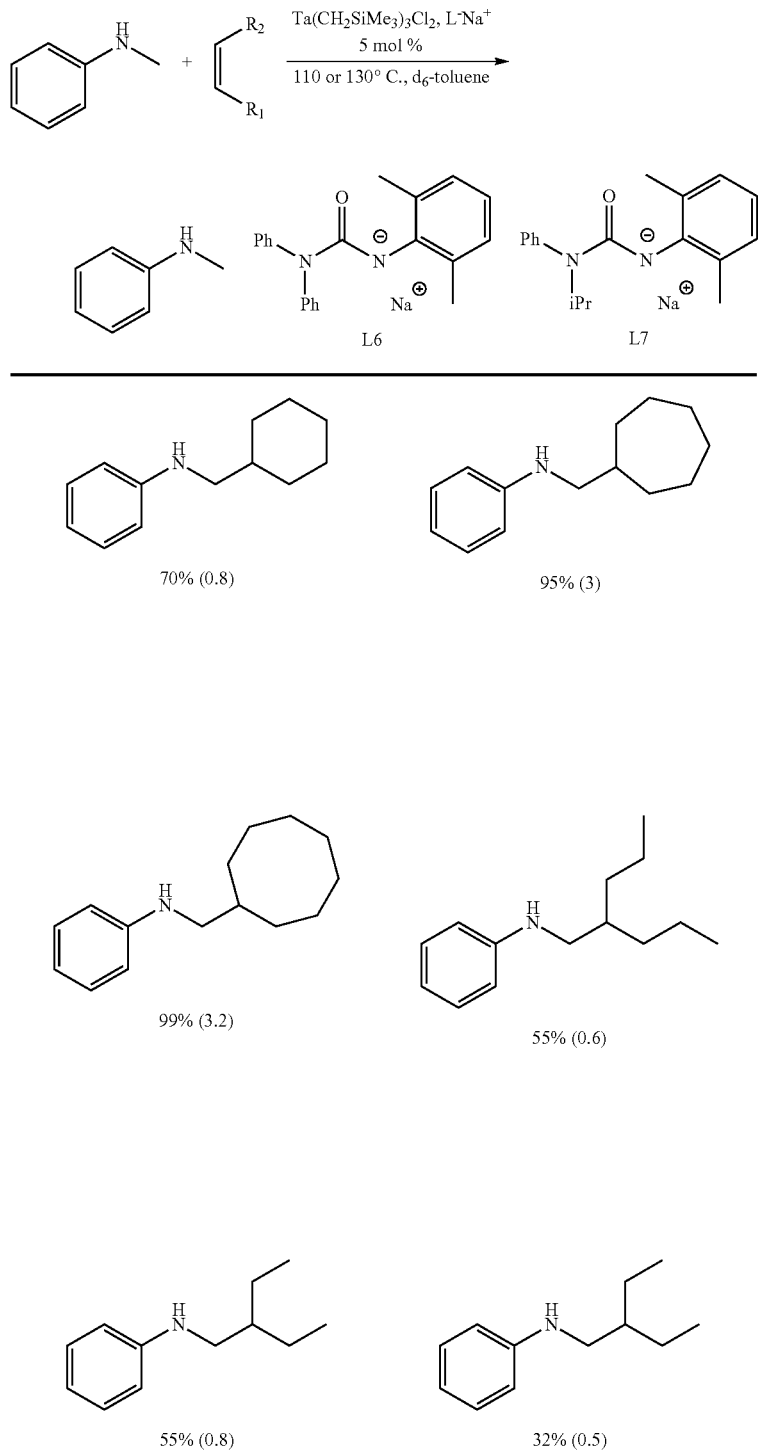

a) Reaction conditions: amine (0.5 mmol), alkene (0.5 mmol), Ta(CH$_2$SiMe$_3$)$_3$Cl$_2$ (0.025 mmol), ligand salt (0.025 mmol), d$_8$-toluene (0.5 g). Conversion determined by $^1$H NMR spectroscopy. All reactions with terminal alkene substrates we're performed with L6 at 110° C. Reactions with internal alkene substrates were performed with L7 at 130° C.

b). Major isomer presented, yield refers to combined regioisomers.

Table 8 provides additional data with respect to the addition of N-methyl butylamine to various alkenes.

TABLE 8

Addition of various alkenes to N-methyl butylamine.

| Entry | Alkene | Temperature (° C.) | Time (h) | Conversion (%) |
|---|---|---|---|---|
| 1 | SiMe₃ (vinyl) | 110 | 24 | 94 |
| 2 | vinylcyclohexane | 145 | 24 | 94 |
| 3 | styrene | 110 | 24 | 50 |
| 4 | allyl-OTBDMS | 145 | 24 | 0 |
| 5 | allylbenzene | 145 | 1 | 0 |
| 6 | 1,5-hexadiene | 145 | 24 | 78 |

Table 9 provides additional data with respect to the effect of various ureate ligand salts and metal complexes on the addition of piperidine to styrene.

TABLE 9

Screening of ligand salts in hydroaminoalkylation reactions in which piperidine is reacted with styrene.

| Entry | Ligand | Temperature (° C.) | Time (h) | Percent Conversion | A:B | dr |
|---|---|---|---|---|---|---|

TABLE 9-continued

| # | Ligand | Temp | Time | Conv | Ratio | Sel |
|---|---|---|---|---|---|---|
| 1 | Ph-N(Ph)-C(O)-N(⊖)(2,6-Me₂C₆H₃), Na⊕ | 150 | 20 | 100 | 1.71:1 | 16:1 |
| 2 | Piperidinyl-C(O)-N(⊖)(2,6-iPr₂C₆H₃), Na⊕ | 150 | 20 | 100 | 2:1 | 20:1 |
| 3 | Me(iPr)N-C(O)-N(⊖)(2,6-Me₂C₆H₃), Na⊕ | 150 | 20 | 100 | 2.2:1 | 18:1 |
| 4 | Me(CHPh₂)N-C(O)-N(⊖)(2,6-Me₂C₆H₃), Na⊕ | 150 | 20 | 100 | 1.7:1 | 15:1 |
| 5 | Me(CH(Ph)Me)N-C(O)-N(⊖)(2,6-iPr₂C₆H₃), Na⊕ | 150 | 20 | 100 | 1.4:1 | 18:1 |

Example 5: Hydroamination Reaction Between Piperidine and 1-Octene

Tables 10 and 11 provides data with respect to the effect of various ureate ligand salts and metal complexes on the addition of piperidine to 1-octene.

TABLE 10

Hydroaminoalkylation data using cyclic ureate salts and Ta(CH₂SiMe₃)₃Cl₂ for the reaction between piperidine and 1-octene.

piperidine + 1-octene →[Ta(CH₂SiMe₃)₃Cl₂, 5 mol %, L⁻Na⁺, 165° C., d₆-toluene] 2-(octan-2-yl)piperidine

| Ligand salt | Time (h) | Conversion (%) |
|---|---|---|
| Cyclohexyl-isopropyl cyclic ureate Na⊕ | 144 | 100 |
| tert-Butyl-isopropyl cyclic ureate Na⊕ | 144 | 100 |

TABLE 11

| Ligand | Temperature (° C.) | Time (h) | Conversion (%) |
|---|---|---|---|
| [structure: piperidine-C(=O)-N⁻(Na⁺)-2,6-dimethylphenyl] | 150 | 6 | 0 |
| [structure: Ph,Ph-N-C(=O)-N⁻(Na⁺)-2,6-dimethylphenyl] | 150 | 6 | 100 |
| [structure: Ph,iPr-N-C(=O)-N⁻(Na⁺)-2,6-dimethylphenyl] | 150 | 6 | 100 |
| [structure: piperidine-C(=O)-N⁻(Na⁺)-2,6-diisopropylphenyl] | 150 | 6 | 100 |
| [structure: Me,CH(Ph)(Me)-N-C(=O)-N⁻(Na⁺)-2,6-dimethylphenyl] | 150 | 6 | 100 |
| [structure: Me,iPr-N-C(=O)-N⁻(Na⁺)-2,6-dimethylphenyl] | 150 | 6 | 37 |

Example 6. Effect of Temperature on Hydroaminoalkylation

Figure 43:
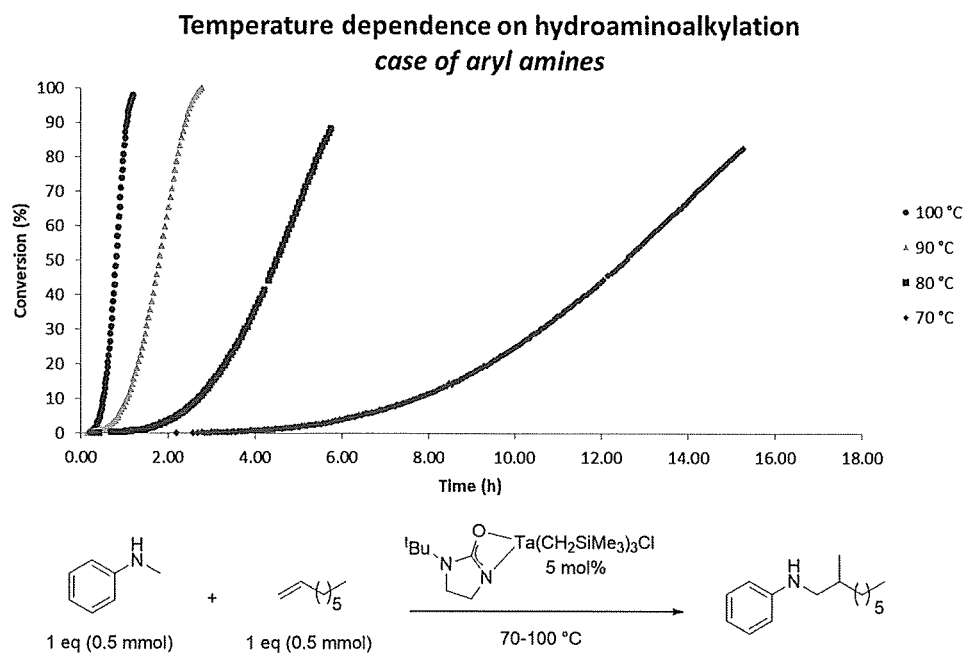
FIG. 43 is a graph showing the effect of reaction temperature on hydroaminoalkylation for an aryl amine.
Figure 44:
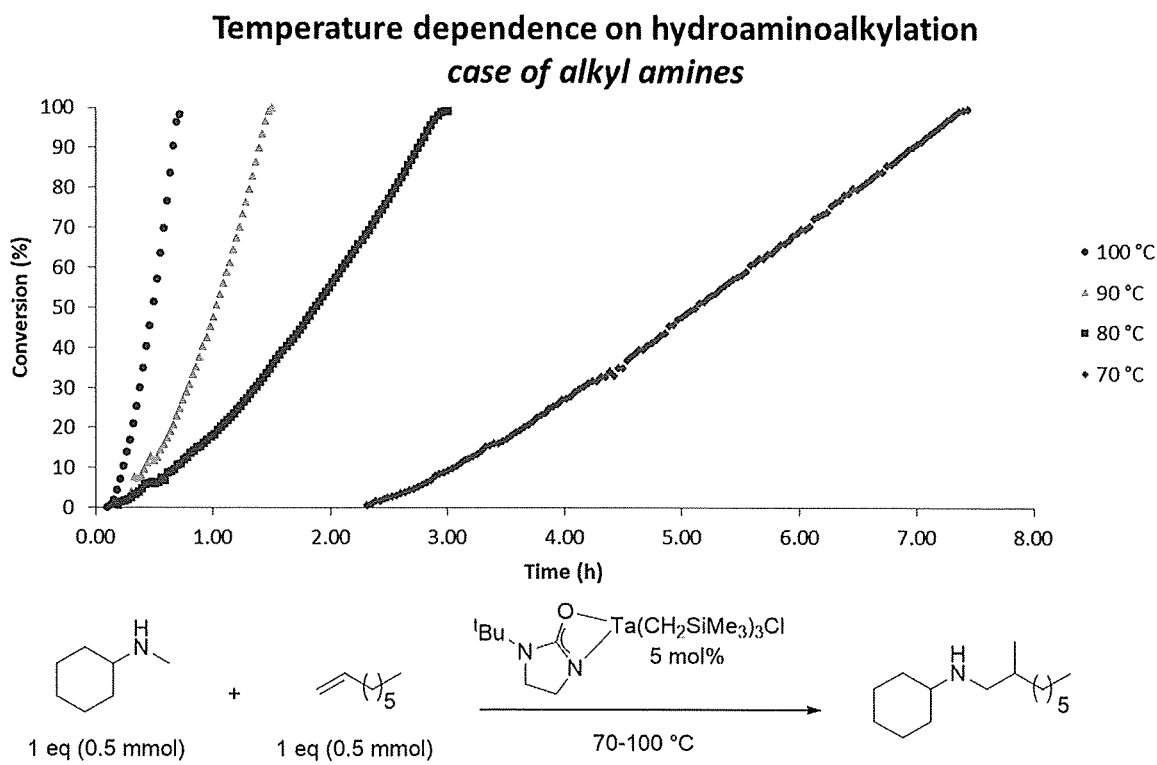
FIG. 44 is a graph showing the effect of reaction temperature on hydroaminoalkylation for an alkyl amine.

FIGS. 43 and 44 illustrate that the rate of the hydroaminoalkylation reaction for aryl and alkyl amines with 1-octene in the presence of metal complexes disclosed herein is temperature dependent and increases with temperature from 70° C. to 100° C.

Example 8. Effect of Catalyst Concentration on Hydroaminoalkylation

Figure 45:
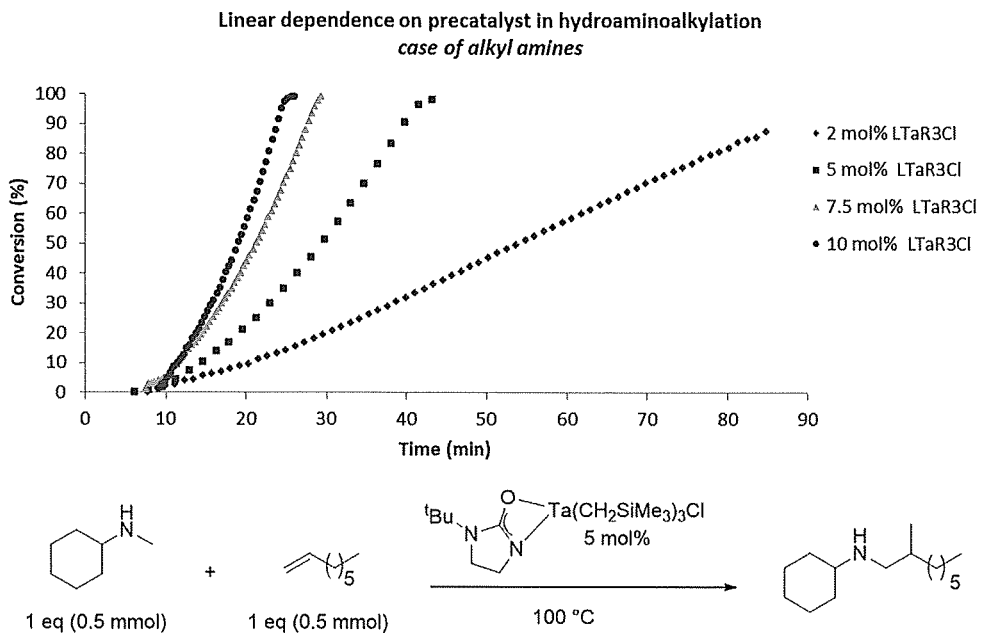
FIG. 45 is a graph showing the effect of precatalyst concentration on hydroaminoalkylation for an alkyl amine.

FIG. 45 illustrates that the rate of the hydroaminoalkylation reaction for alkyl amines with 1-octene in the presence of metal complexes disclosed herein is concentration dependent and increases with concentration 2 mol % to 10 mol %.

Example 7. Effect of Halide Salts on Hydroaminoalkylation

Figure 46:
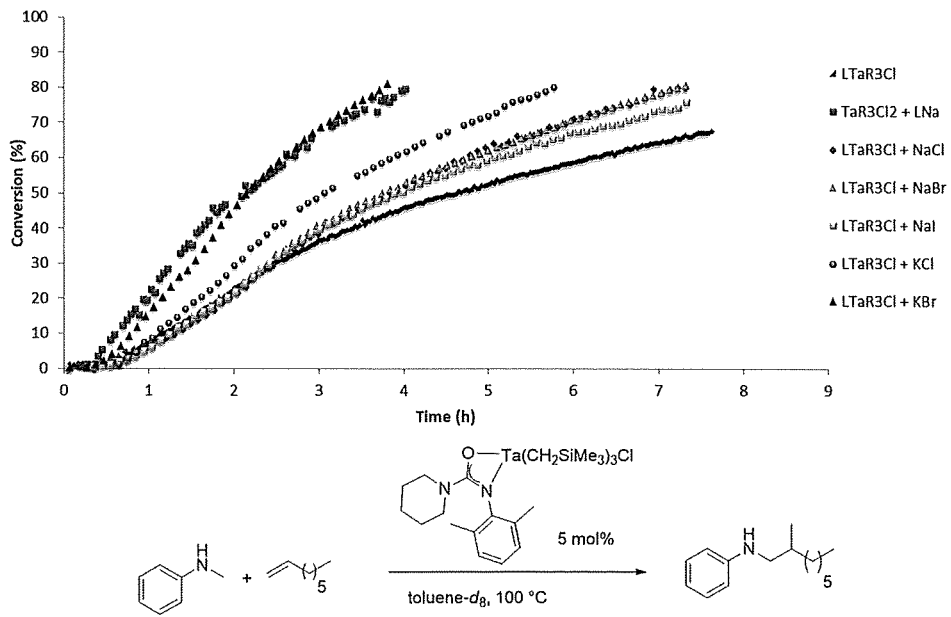
FIG. 46 is a graph showing the effect of Lewis acid salts on hydroaminoalkylation for an aryl amine.
Figure 47:
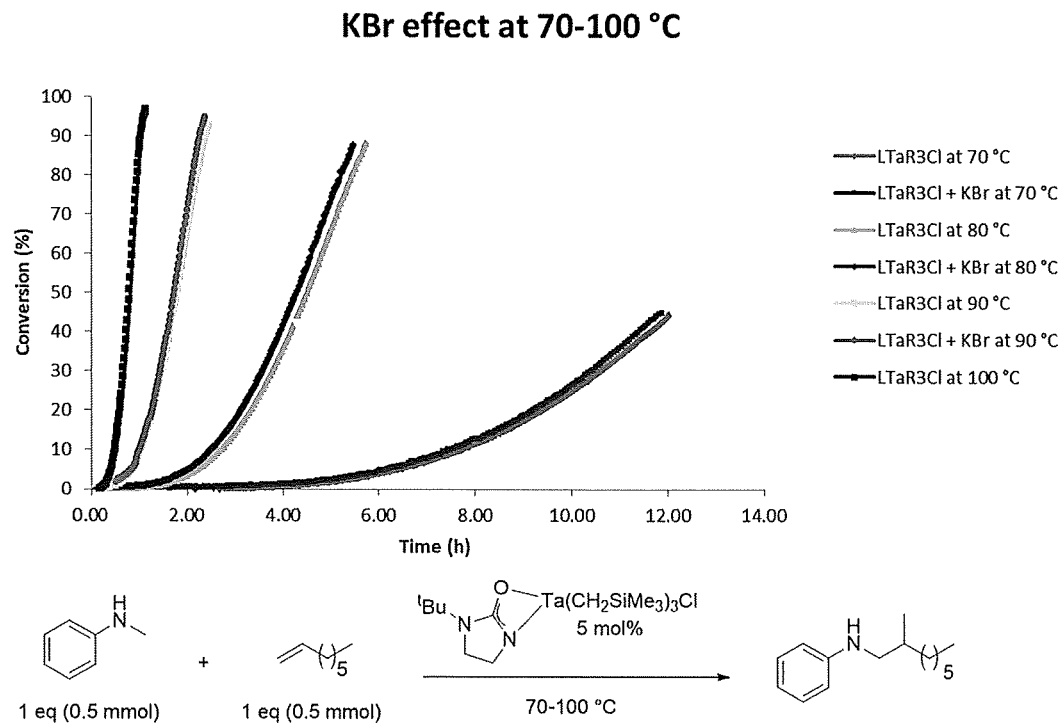
FIG. 47 is a graph showing the effect of KBr on hydroaminoalkylation for an aryl amine at different temperatures.
Figure 48:
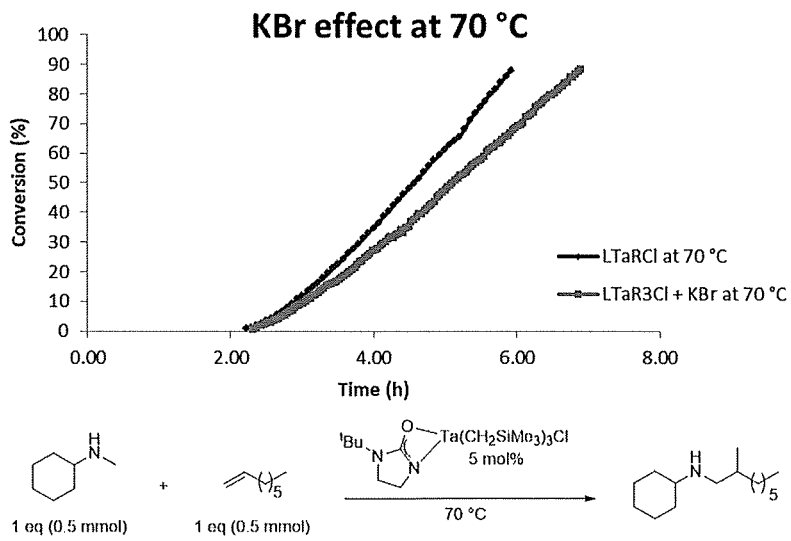
FIG. 48 is a graph showing the effect of KBr on hydroaminoalkylation for an alkyl amine.

FIG. 46 illustrates that the rate of the hydroaminoalkylation reaction for aryl amines with 1-octene in the presence of metal complexes disclosed herein increases with the addition of halide salts. FIGS. 47 and 48 demonstrate that the rate of the hydroaminoalkylation reaction for aryl amines with 1-octene in the presence of metal complexes disclosed herein increases with the addition of KBr at temperatures from 70° C. to 100° C.

The experiments which were performed in the presence of an internal standard (1,3,5-trimethoxybenzene) show that all employed vinyl terminated polyolefins can be successfully aminated with aromatic and alkylamines in as little as 2 hours. Recorded data shows that when N-methylaniline and N-methylcyclohexylamine are used as amine substrates, the temperature can be as low as 110° C. On the other hand, reactions employing N-methylbutylamine require 145° C. to reach full conversion.

Example 8. Amination of Polyolefins

Figure 49:
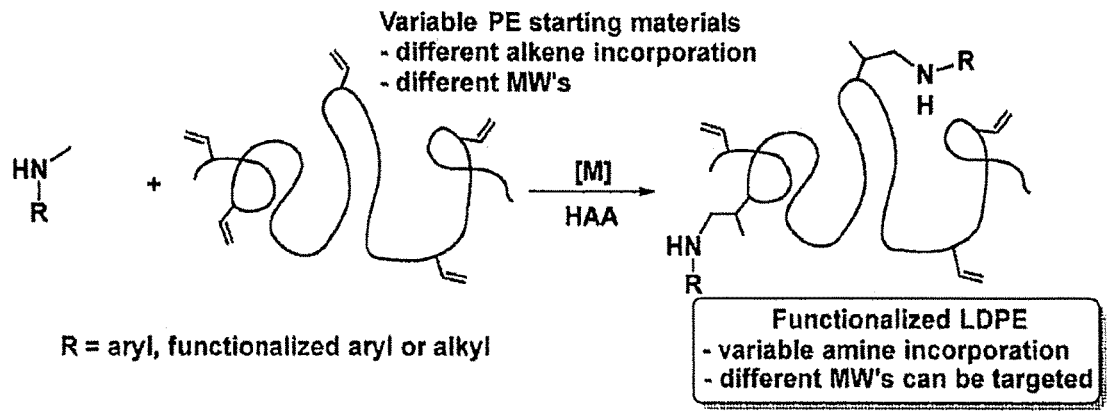
FIG. 49 is a schematic diagram depicting hydroaminoalkylation of polyolefins comprising alkene groups

FIG. 49 depicts a hydroaminoalkylation reaction of a polyolefin comprising alkene groups according to the methods disclosed herein. While FIG. 49 depicts hydroaminoalkylation of a polyolefin comprising pendant alkene groups, and pendent vinyl groups in particular, the skilled person will understand that the reaction could be generally applicable to polyolefins having an alkene group, whether pendent alkene groups or Table 12 summarizes the results of amination of representative polyolefins, i.e vinyl-terminated polypropylene and a vinyl-terminated ethylene polypropylene copolymer, with three representative amines (N-methylaniline, N-methylcyclohexylamine, or N-methylbutylamine) using $^{tBu}$LTa(CH$_2$SiMe$_3$)$_3$Cl as a representative catalyst.

TABLE 12

Postpolymerization modification of polyolefins [a]

polyolefin = aPP, EP
R = Ph, Cy, nBu
[Ta] 5 mol %, 110-145° C.
toluene, 1-1.5 h

[Ta] = tBu-N-C(=O)-N-Ta(CH$_2$SiMe$_3$)$_3$Cl (1)

isolated or in situ

| Entry | Polyolefin | R | Temp. (° C.) | Time (h) | Conv. (%) | TOF (h$^{-1}$) |
|---|---|---|---|---|---|---|
| 1 | Sample 1 | Ph | 110 | 0.5 | 63 | 25 |
| 2 | vt aPP[b] | | | 1 | 100 | 20 |
| 3 | | Cy | | 0.5 | 63 | 25 |
| 4 | | | | 1 | 100 | 20 |
| 5 | | nBu | 145 | 0.5 | 17 | 7 |
| 6 | | | | 1 | 29 | 6 |
| 7 | Sample 2 | Ph | | 0.5 | 40 | 16 |
| 8 | vt aPP[c] | | 110 | 1.5 | 100 | 13 |
| 9 | | Cy | | 0.5 | 57 | 23 |
| 10 | | | | 1.5 | 100 | 13 |
| 11 | | nBu | 145 | 0.5 | 25 | 10 |
| 12 | Sample 3 | Ph | 110 | 0.5 | 28 | 11 |
| 13 | vt EP[c] | Cy | | 0.5 | 61 | 24 |
| 14 | | nBu | 145 | 0.5 | 35 | 14 |

[a]Determined by $^1$H NMR spectroscopy using 1,3,5-trimethoxybenzene as standard.
[b]Polymer employed as neat.
[c]Polymer employed as a stock solution in toluene-d$_8$ (25% wt).

Figure 50:
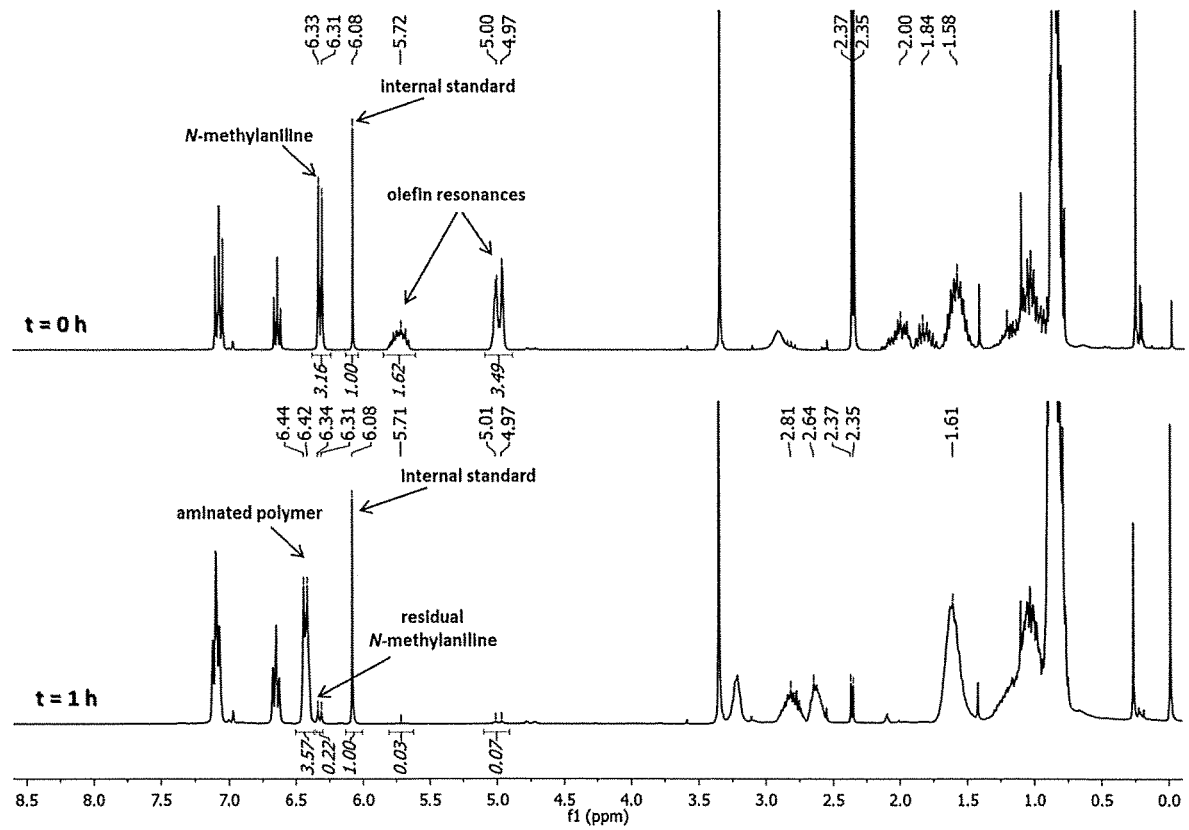
FIG. 50 is $^1$H NMR spectra (toluene-d$_8$, 300 MHz, 298 K) of a mixture between 25691-151-005 vt aPP, N-methylaniline and 1,3,5-trimethoxybenzene (top) and the resulting polymer (bottom).

FIG. 50 shows $^1$H NMR spectra (toluene-d$_8$, 300 MHz, 298 K) of a mixture between Sample 1, N-methylaniline and 1,3,5-trimethoxybenzene (top) and the resulting polymer (bottom). The resultant animated material was isolated as a pale yellow gooey oil. The aminated material is soluble in common solvents (e.g. hexanes EtOAc, MeOH etc.).

Figure 51:
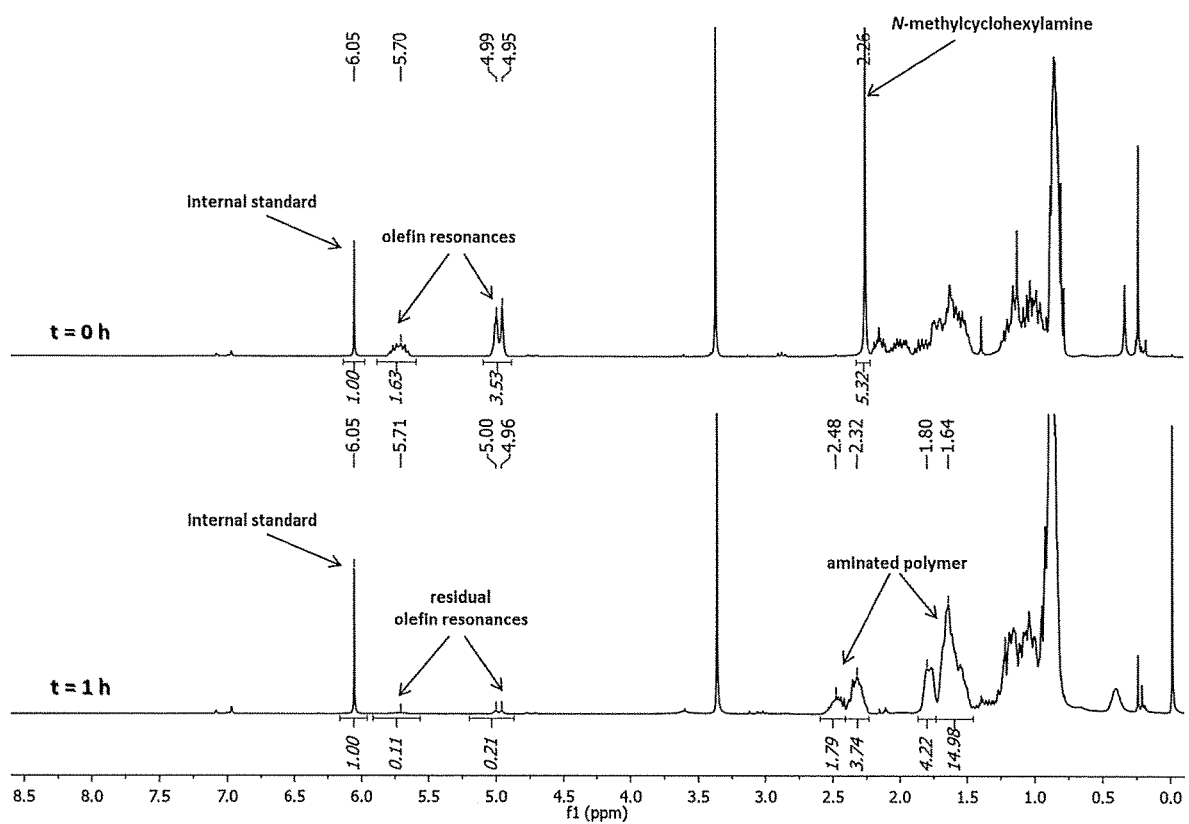
FIG. 51 is $^1$H NMR spectra (toluene-d$_8$, 300 MHz, 298 K) of a mixture between 25691-151-005 vt aPP, N-methylcyclohexylamine and 1,3,5-trimethoxybenzene (top) and the resulting polymer (bottom).

FIG. 51 shows $^1$H NMR spectra (toluene-d$_8$, 300 MHz, 298 K) of a mixture between Sample 1, N-methylcyclohexylamine and 1,3,5-trimethoxybenzene (top) and the resulting polymer (bottom). The resultant aminated material was isolated as a pale yellow gooey oil. The aminated material is soluble in common solvents (e.g. hexanes EtOAc, MeOH etc.).

Figure 52:
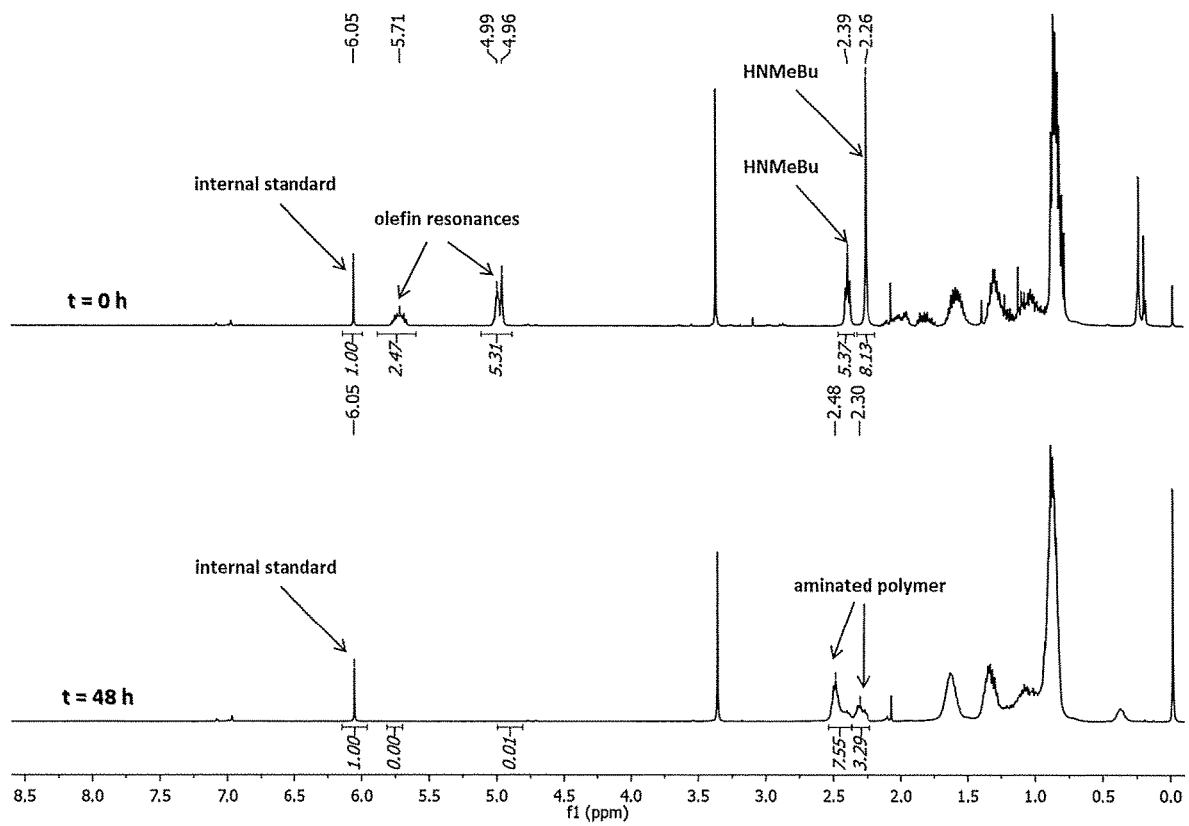
FIG. 52 is $^1$H NMR spectra (toluene-d$_8$, 300 MHz, 298 K) of a mixture between 25691-151-005 vt aPP, N-methylbutylamine and 1,3,5-trimethoxybenzene (top) and the resulting polymer (bottom).

FIG. 52 shows $^1$H NMR spectra (toluene-d$_8$, 300 MHz, 298 K) of a mixture between 25691-151-005 vt aPP, N-methylbutylamine and 1,3,5-trimethoxybenzene (top) and the resulting polymer (bottom). The resultant aminated material was isolated as a pale yellow gooey oil. The aminated material is soluble in common solvents (e.g. hexanes, EtOAc, MeOH etc.)

Figure 53:
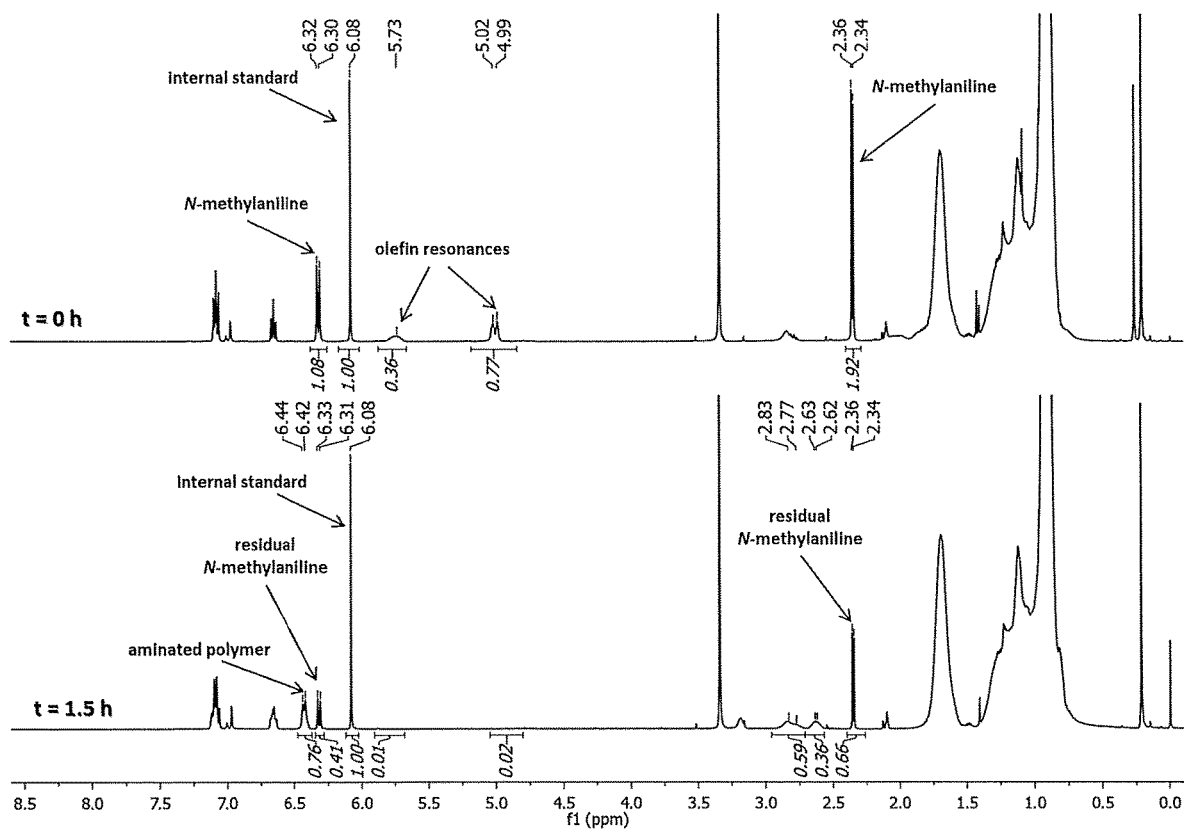
FIG. 53 is $^1$H NMR spectra (toluene-d$_8$, 400 MHz, 298 K) of a mixture between 26352-052-001 vt aPP, N-methylaniline and 1,3,5-trimethoxybenzene (top) and the resulting polymer (bottom).

FIG. 53 shows $^1$H NMR spectra (toluene-d$_8$, 400 MHz, 298 K) of a mixture between Sample 2, N-methylaniline and 1,3,5-trimethoxybenzene (top) and the resulting polymer (bottom). The resultant aminated material was isolated as a white very dense oil. The aminated material is very soluble in dichloromethane and insoluble in hexanes, EtOAc, and MeOH.

Figure 54:
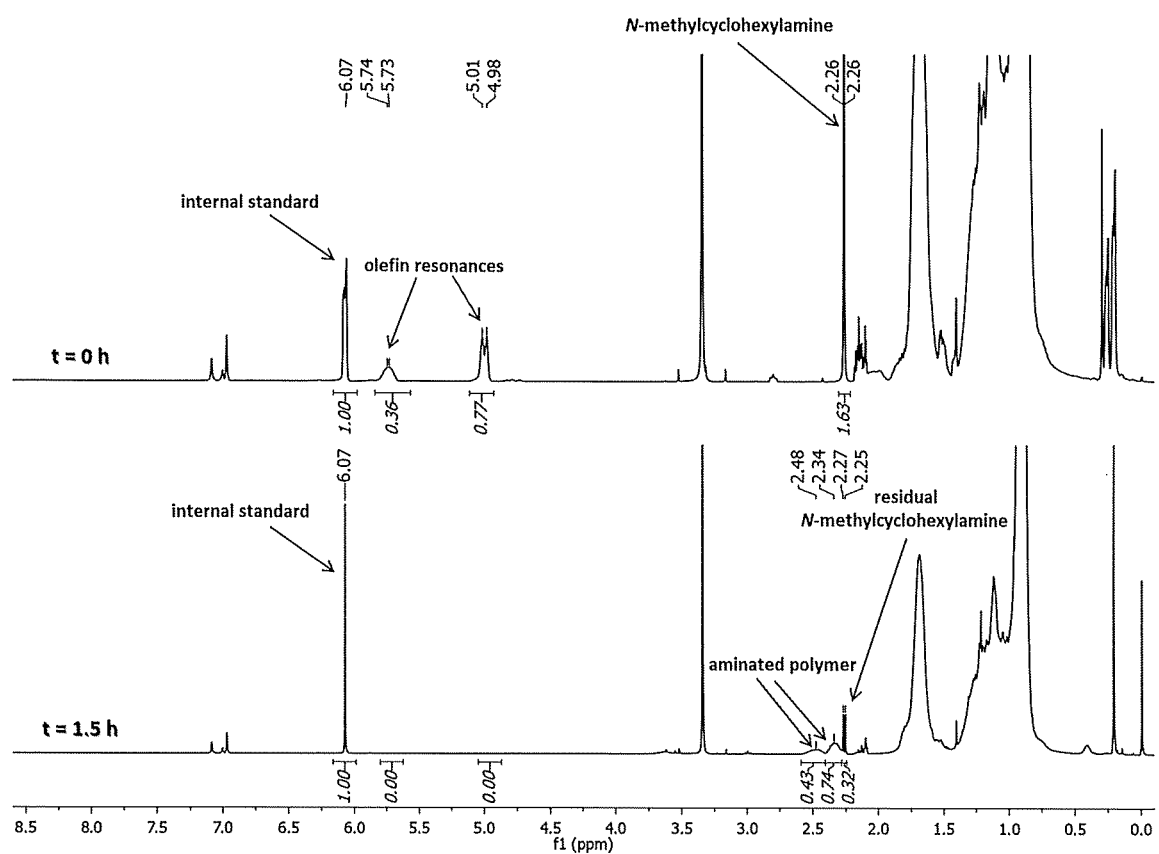
FIG. 54 is $^1$H NMR spectra (toluene-d$_8$, 400 MHz, 298 K) of a mixture between 26352-052-001 vt aPP, N-methylcyclohexylamine and 1,3,5-trimethoxybenzene (top) and the resulting polymer (bottom).

FIG. 54 shows $^1$H NMR spectra (toluene-d$_8$, 400 MHz, 298 K) of a mixture between Sample 2, N-methylcyclohexylamine and 1,3,5-trimethoxybenzene (top) and the resulting polymer (bottom). The resultant aminated material was isolated as a white very dense oil. The aminated material is very soluble in dichloromethane and insoluble in hexanes, EtOAc, and MeOH.

Figure 55:
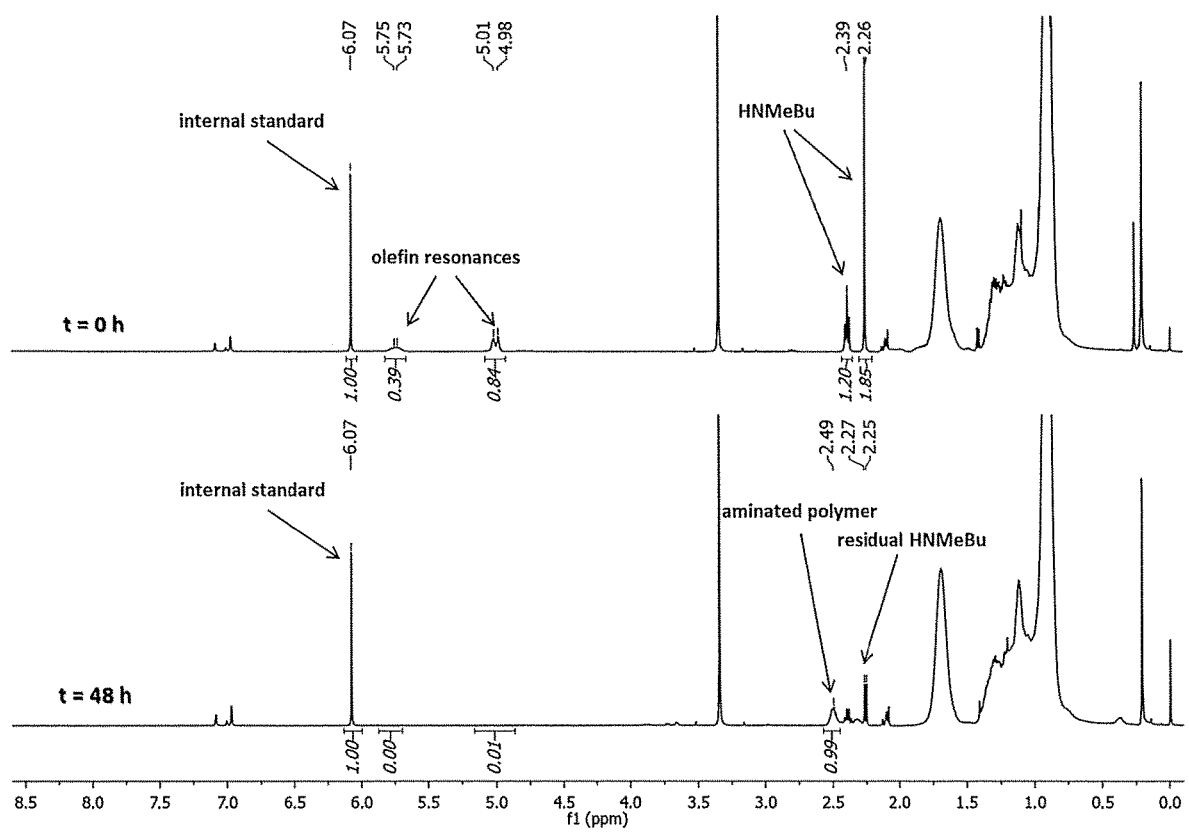
FIG. 55 is $^1$H NMR spectra (toluene-d$_8$, 400 MHz, 298 K) of a mixture between 26352-052-001 vt aPP, N-methylbutylamine and 1,3,5-trimethoxybenzene (top) and the resulting polymer (bottom).

FIG. 55 shows $^1$H NMR spectra (toluene-d$_8$, 400 MHz, 298 K) of a mixture between Sample 2, N-methylbutylamine and 1,3,5-trimethoxybenzene (top) and the resulting polymer (bottom). The resultant aminated material was isolated as a white very dense oil. The aminated material is very soluble in dichloromethane and insoluble in hexanes, EtOAc, and MeOH.

Figure 56:
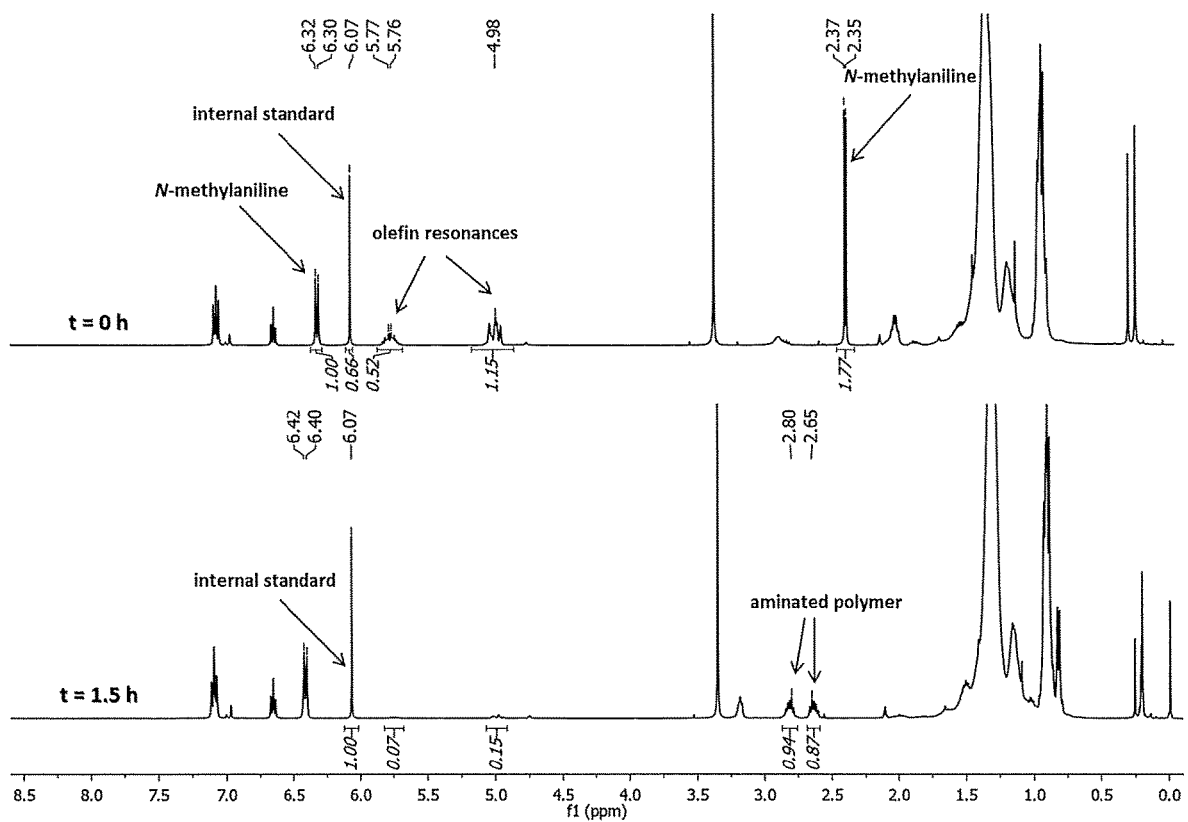
FIG. 56 is $^1$H NMR spectra (toluene-d$_8$, 400 MHz, 298 K) of a mixture between 25333-151-004 vt EP, N-methylaniline and 1,3,5-trimethoxybenzene (top) and the resulting polymer (bottom).

FIG. 56 shows $^1$H NMR spectra (toluene-d$_8$, 400 MHz, 298 K) of a mixture between Sample 3, N-methylaniline and 1,3,5-trimethoxybenzene (top) and the resulting polymer (bottom). The resultant aminated material was isolated as white very dense oil. The aminated material is very soluble in dichloromethane and insoluble in hexanes, EtOAc, and MeOH.

Figure 57:
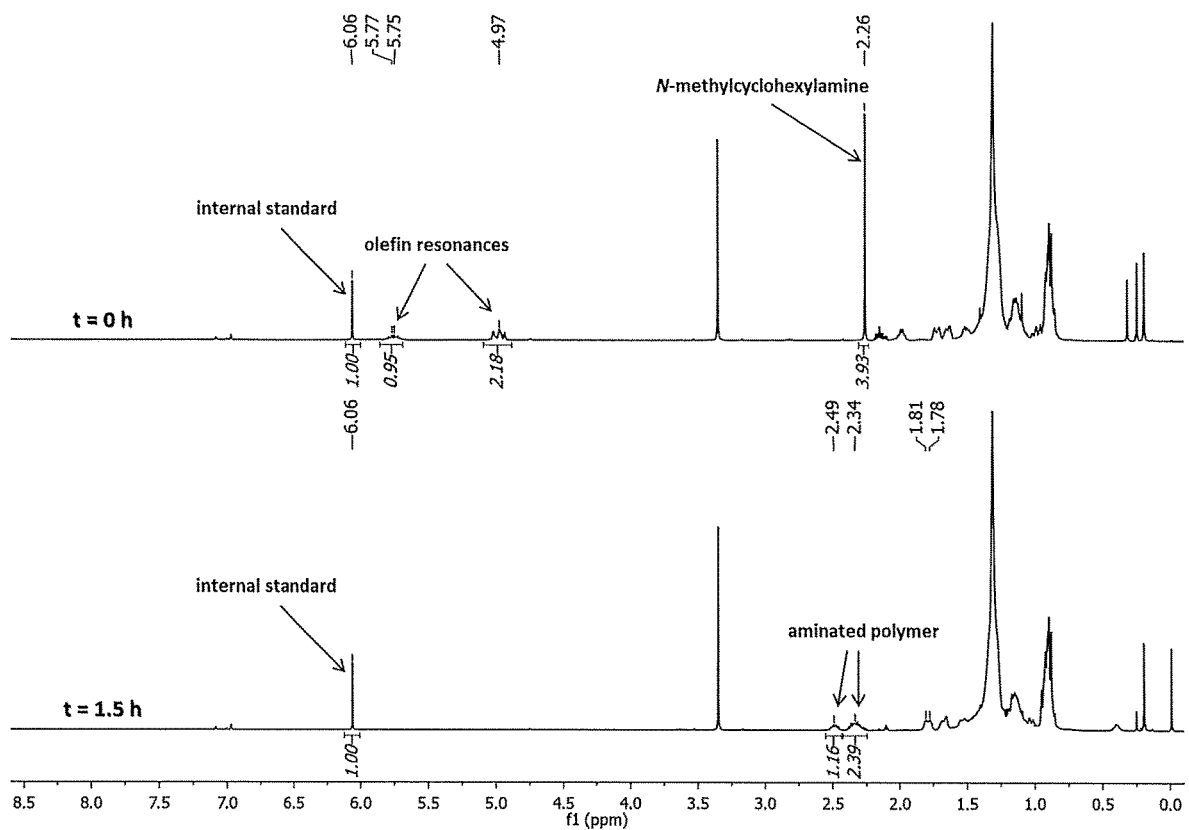
FIG. 57 is $^1$H NMR spectra (toluene-d$_8$, 400 MHz, 298 K) of a mixture between 25333-151-004 vt EP, N-methylcyclohexylamine and 1,3,5-trimethoxybenzene (top) and the resulting polymer (bottom).

FIG. 57 shows $^1$H NMR spectra (toluene-$d_8$, 400 MHz, 298 K) of a mixture between Sample 3, N-methylcyclohexylamine and 1,3,5-trimethoxybenzene (top) and the resulting polymer (bottom). The resultant aminated material was isolated as white very dense oil. The aminated material is very soluble in dichloromethane and insoluble in hexanes, EtOAc, and MeOH.

Figure 58:
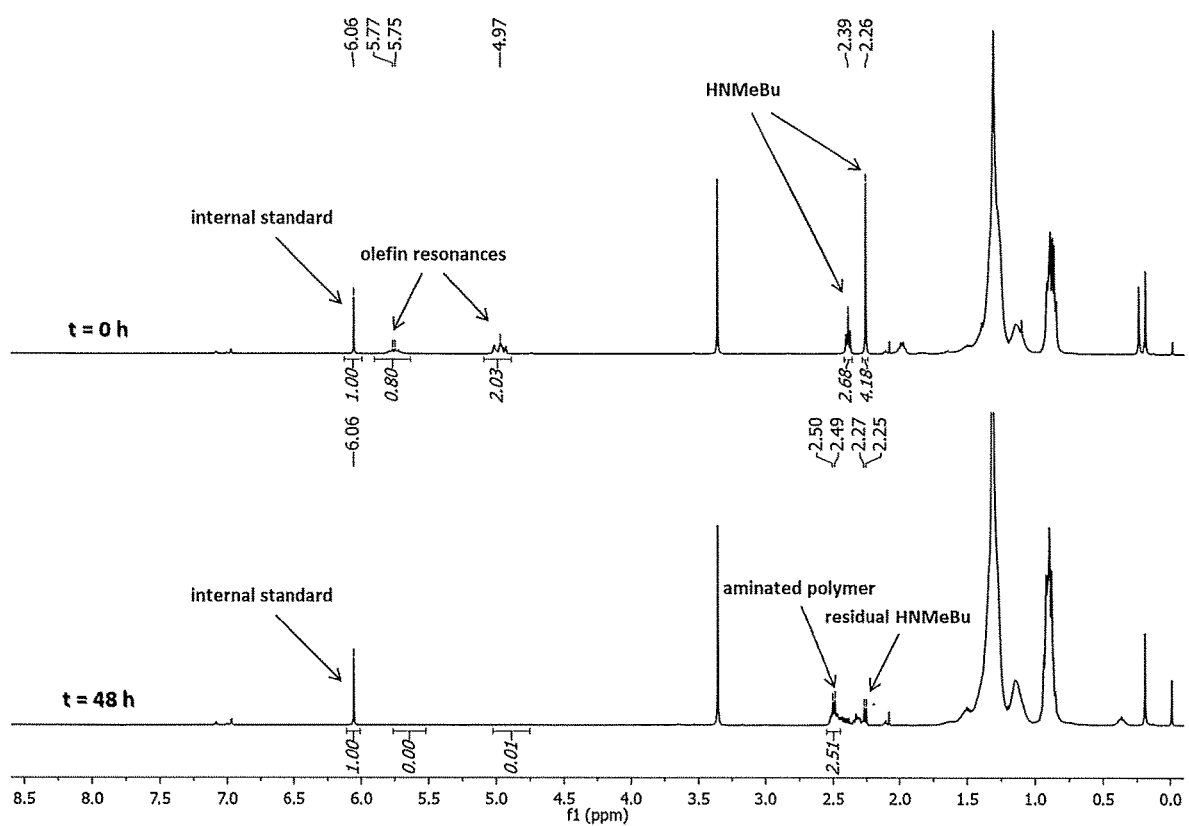
FIG. 58 is $^1$H NMR spectra (toluene-d$_8$, 400 MHz, 298 K) of a mixture between 25333-151-004 vt EP, N-methylbutylamine and 1,3,5-trimethoxybenzene (top) and the resulting polymer (bottom).

FIG. 58 shows $^1$H NMR spectra (toluene-$d_8$, 400 MHz, 298 K) of a mixture between Sample 3, N-methylbutylamine and 1,3,5-trimethoxybenzene (top) and the resulting polymer (bottom). The resultant aminated material was isolated as white very dense oil. The aminated material is very soluble in dichloromethane and insoluble in hexanes, EtOAc, and MeOH.

The experiments which were performed in the presence of an internal standard (1,3,5-trimethoxybenzene) show that each of the employed polyolefins can be successfully aminated with aromatic and alkylamines in as little as 2 hours. When N-methylaniline and N-methylcyclohexylamine are used as amine substrates, the temperature can be as low as 110° C. Based on NMR experiments the initial both the initial polymers and the resulting ones have a molecular weight range between 350-3500 g/mol.

Operation

While specific embodiments of the invention have been described and illustrated, such embodiments should be considered illustrative of the invention only and not as limiting the invention as construed in accordance with the accompanying claims.

What is claimed is:

1. A method for amination of a polyolefin having at least one alkene group, the method comprising: (i) reacting a secondary amine-containing moiety with the polyolefin in the presence of a metal complex, the metal complex having the structure of Formula I:

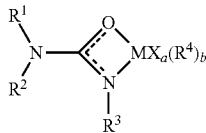

(Formula I)

wherein:
(i) $R^1$ and $R^2$ are each independently H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or $R^1$ and $R^2$ are bonded together thereby forming, together with the nitrogen atom they are both bound to, a heterocycle; and
$R^3$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or
(ii) $R^1$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; and
$R^3$ is bonded together with $R^2$ to form a heterocycle;
M is a group 5 metal;

a=0 to 4 and b=0 to 4, wherein the sum of a and b is 4;
each X is a halogen substituent; and
each $R^4$ is independently H; or a $C_1$-$C_{20}$ substituted or unsubstituted, linear, branched or cyclic alkyl, optionally comprising heteroatoms.

2. The method of claim 1, wherein each X is independently Cl or Br, a=1 or 2 and b=2 or 3.

3. The method of claim 2, wherein a=1.

4. The method of claim 1, wherein $R^3$ is bonded together with $R^2$ to form, together with each of the nitrogen atoms they are bound to, a 5-membered ring, which optionally may be substituted.

5. The method of claim 4, having the structure:

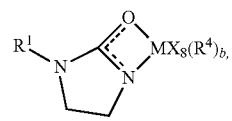

wherein
$R^1$ is methyl, tert-butyl, phenyl, cyclohexyl or adamantyl.

6. The method of claim 1, wherein $R^4$ is —$CH_2Si(CH_3)_3$.

7. The method of claim 1, wherein M is tantalum (Ta).

8. The method of claim 1, wherein the metal complex is:

9. The method of claim 1, wherein the at least one alkene group comprises at least one vinyl group.

10. The method of claim 1, wherein the at least one alkene group comprises at least one pendant alkene group.

11. The method of claim 1, wherein the polyolefin is a vinyl-terminated polyolefin.

12. The method of claim 1, wherein the polyolefin comprises a polypropylene.

13. The method of claim 1, wherein the polyolefin comprises a poly(ethylene-co-propylene) copolymer.

14. The method of claim 1, wherein the molecular weight of the polyolefin is in the range of about 100 g/mol to about 10,000 g/mol.

15. The method of claim 1, wherein the reaction conditions comprise a reaction temperature in the range from 110° C. to 165° C.

16. The method of claim 1, wherein the reaction conditions comprise a solvent.

17. The method of claim 16, wherein the solvent comprises toluene.

18. The method of claim 1, wherein the metal complex is generated in situ from a group 5 metal salt of Formula VII $MX_c(R^4)_d$   (Formula VII)

wherein:
M is a group 5 metal;
c=1 to 5 and d=0 to 4, wherein the sum of c and d is 5; and
each $R^4$ is independently H; or a $C_1$-$C_{20}$ substituted or unsubstituted, linear, branched or cyclic alkyl, optionally comprising heteroatoms, in combination with an amide of Formula VIII

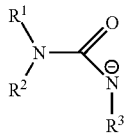
(Formula VIII)

(i) $R^1$ and $R^2$ are each independently H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or
$R^1$ and $R^2$ are bonded together thereby forming, together with the nitrogen atom they are both bound to, a heterocycle; and
$R^3$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or (ii) $R^1$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; and
$R^3$ is bonded together with $R^2$ to form a heterocycle.

19. The method of claim 1, wherein the secondary amine-containing moiety is:

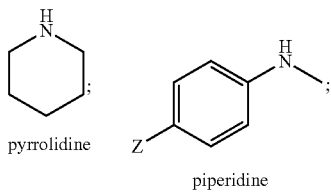

pyrrolidine     piperidine

-continued

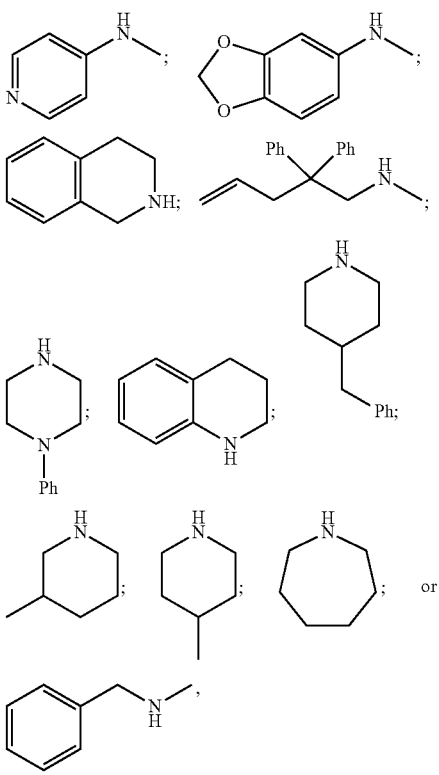

wherein Z is H, $OCF_3$, F, Cl, Br, I, or $OCH_3$.

20. The method of claim 1, wherein the secondary amine-containing moiety is N-methylaniline, N-methylcyclohexylamine, or N-methylbutylamine.

* * * * *